United States Patent [19]
Ahmad et al.

[11] Patent Number: 6,011,059
[45] Date of Patent: Jan. 4, 2000

[54] ACYL GUANIDINE SODIUM/PROTON EXCHANGE INHIBITORS AND METHOD

[75] Inventors: Saleem Ahmad, Wall; Shung C. Wu, Lawrenceville, both of N.J.; Karnail S. Atwal, Newtown, Pa.; Sundeep Dugar, Bridgewater, N.J.

[73] Assignee: Bristol-Myers Squibb Company, Princeton, N.J.

[21] Appl. No.: 09/198,159

[22] Filed: Nov. 23, 1998

Related U.S. Application Data

[60] Provisional application No. 60/068,790, Dec. 24, 1997, and provisional application No. 60/073,740, Feb. 5, 1998.

[51] Int. Cl.⁷ .......................... A61K 31/34; A61K 31/44; A61K 31/165; C07D 307/79; C07C 233/62

[52] U.S. Cl. .......................... 514/469; 514/351; 514/364; 514/399; 514/403; 514/423; 514/454; 514/617; 514/619; 514/634; 546/332; 548/125; 548/336.5; 548/375.1; 548/537; 549/433; 549/441; 549/467; 564/161; 564/166; 564/230; 564/237

[58] Field of Search .......................... 564/230, 237, 564/161, 166; 514/634, 469, 464, 399, 403, 364, 454, 423, 617, 619, 351; 549/467, 441, 433; 548/336.5, 375.1, 125, 537; 546/332

[56] References Cited

U.S. PATENT DOCUMENTS

| | | | |
|---|---|---|---|
| 3,728,332 | 4/1973 | Tessler | 260/233.5 |
| 5,336,689 | 8/1994 | Weber et al. | 514/634 |
| 5,733,934 | 3/1998 | Ramakrishna | 514/634 |
| 5,756,535 | 5/1998 | Schwark et al. | 514/445 |
| 5,814,654 | 9/1998 | Kitano | 514/411 |
| 5,852,046 | 12/1998 | Lang | 514/419 |

FOREIGN PATENT DOCUMENTS

| | | |
|---|---|---|
| 0639573A1 | 2/1995 | European Pat. Off. . |
| 0738712A1 | 10/1996 | European Pat. Off. . |
| 744397A2 | 11/1996 | European Pat. Off. . |
| 790245A1 | 8/1997 | European Pat. Off. . |
| 0803501A1 | 10/1997 | European Pat. Off. . |
| 08053336 | 2/1996 | Japan . |
| 959245 | 4/1997 | Japan . |
| 967340 | 11/1997 | Japan . |
| 10316647 | 12/1998 | Japan . |
| WO97/46226 | 12/1997 | WIPO . |

*Primary Examiner*—Evelyn Mei Huang
*Attorney, Agent, or Firm*—Burton Rodney

[57] ABSTRACT

Acyl guanidines are provided which are sodium/proton exchange (NHE) inhibitors which have the structure

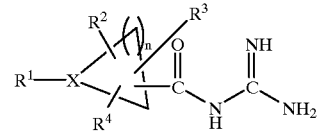

wherein n is 1 to 5; X is N or C—$R^5$ wherein $R^5$ is H, halo, alkenyl, alkynyl, alkoxy, alkyl, aryl or heteroaryl; and $R^1$, $R^2$, $R^3$ and $R^4$ are as defined herein, and where X is N, $R^1$ is preferably aryl or heteroaryl, and are useful as antianginal and cardioprotective agents. In addition, a method is provided for preventing or treating angina pectoris, cardiac dysfunction, myocardial necrosis, and arrhythmia employing the above acyl guanidines.

23 Claims, No Drawings

ACYL GUANIDINE SODIUM/PROTON EXCHANGE INHIBITORS AND METHOD

This application claims the benefit of provisional application Ser. No. 60/068,790, filed Dec. 24, 1997 and Ser. No. 60/073,740, filed on Feb. 5, 1998.

FIELD OF THE INVENTION

The present invention relates to acyl guanidine compounds which are sodium/proton exchange (NHE) inhibitors and are useful as antianginal agents and cardioprotective agents.

BRIEF DESCRIPTION OF THE INVENTION

In accordance with the present invention, novel acyl guanidines are provided which are sodium/proton exchange (NHE) inhibitors and have the structure I

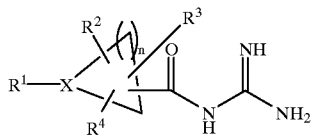

including pharmaceutically acceptable salts thereof and all stereoisomers thereof, and prodrug ester thereof, wherein n is an integer from 1 to 5;

wherein X is N or C—$R^5$ wherein $R^5$ is H, halo, alkenyl, alkynyl, alkoxy, alkyl, aryl or heteroaryl;

$R^1$ is H, alkyl, alkenyl, alkynyl, alkoxy, alkenyloxy, alkynyloxy, (alkyl or aryl)$_3$Si (where each alkyl or aryl group is independent), cycloalkyl, cycloalkenyl, amino, alkylamino, alkenylamino, alkynylamino, arylalkylamino, aryl, arylalkyl, arylamino, aryloxy, cycloheteroalkyl, cycloheteroalkylalkyl, heteroaryl, heteroarylamino, heteroaryloxy, arylthio, arylsulfinyl, arylsulfonyl, thio, alkylthio, alkylsulfinyl, alkylsulfonyl, heteroarylthio, heteroarylsulfinyl, heteroarylsulfonyl, halogen, haloalkyl, polyhaloalkyl such as $CF_3$ and $CF_3CH_2$, polyhaloalkyloxy such as $CF_3O$ and $CF_3CH_2O$, aminothio, aminosulfinyl, aminosulfonyl, alkylsulfonylamino, alkenylsulfonylamino, alkynylsulfonylamino, arylsulfonylamino, heteroarylsulfonylamino, alkylaminocarbonyl, arylaminocarbonyl, heteroarylaminocarbonyl, hydroxy, acyl, carboxy, aminocarbonyl, alkylcarbonyl, alkoxycarbonyl, alkylcarbonyloxy, alkylcarbonylamino, arylcarbonyl, arylcarbonyloxy, arylcarbonylamino, heteroarylcarbonyl, heteroarylcarbonyloxy, heteroarylcarbonylamino, cyano, nitro, alkenylcarbonylamino, alkynylcarbonylamino, alkylaminocarbonylamino, alkenylaminocarbonylamino, alkynylaminocarbonylamino, arylaminocarbonylamino, heteroarylaminocarbonylamino, alkoxycarbonylamino, alkenyloxycarbonylamino, alkynyloxycarbonylamino, aryloxycarbonylamino, heteroaryloxycarbonylamino, aminocarbonylamino, alkylaminocarbonyloxy, 1,1-(alkoxyl or aryloxy)$_2$alkyl (where the two aryl or alkyl substituents can be independently defined, or linked to one another to form a ring, such as 1,3-dioxane or 1,3-dioxolane), $S(O)_2R^6R^7$—$NR^6(C=NR^7)$alkyl, —$NR^6(C=NR^7)$alkenyl, —$NR^6(C=NR^7)$alkynyl, —$NR^6(C=NR^7)$heteroaryl, —$NR^8(C=NCN)$—

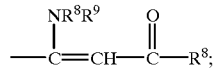

amino, pyridine-N-oxide,

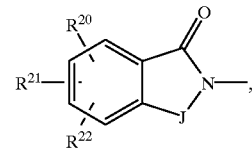

(where Z is O or $H_2$ and n' is 0, 1, 2 or 3) or

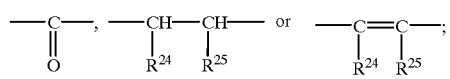

tetrazolyl, imidazole, oxazole or triazole; —$PO(R^{13})(R^{14})$, (where $R^{13}$ and $R^{14}$ are independently alkyl, aryl, alkoxy, aryloxy, heteroaryl, heteroarylalkyl, heteroaryloxy, heteroarylalkoxy, cycloheteroalkyl, cycloheteroalkylalkyl, cycloheteroalkoxy, or cycloheteroalkylalkoxy);

$R^6$, $R^7$, $R^8$ and $R^9$ are independently hydrogen, alkyl, haloalkyl, aryl, heteroaryl, arylalkyl, cycloalkyl, (cycloalkyl)alkyl or cycloheteroalkyl.

The $R^1$ group may have from one to five substituents, which can be any of the $R^1$ groups set out above, and any of the preferred $R^1$ substituents set out below.

$R^1$ may be substituted with the following preferred substituents: alkylcarbonylamino, cycloalkylcarbonylamino, arylcarbonylamino, heteroarylcarbonylamino, alkoxycarbonylamino, aryloxycarbonylamino, heteroaryloxylcarbonylamino, uriedo (where the uriedo nitrogens may be substituted with alkyl, aryl or heteroaryl), heterocyclylcarbonylamino (where the heterocycle is connected to the carbonyl group via a nitrogen or carbon atom), alkylsulfonylamino, arylsulfonylamino, heteroarylsulfonylamino, where J is: $CHR^{23}$, $$-\underset{O}{\overset{}{C}}-, \quad -\underset{R^{24}}{\overset{}{CH}}-\underset{R^{25}}{\overset{}{CH}}- \quad \text{or} \quad -\underset{R^{24}}{\overset{}{C}}=\underset{R^{25}}{\overset{}{C}}-;$$

$R^{23}$, $R^{24}$ and $R^{25}$ are independently hydrogen, alkyl, alkenyl, alkynyl, aryl, arylalkyl, heteroaryl, heteroarylalkyl, cycloalkyl, or cycloalkylalkyl;

$R^{20}$, $R^{21}$, $R^{22}$ are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl; and these preferred substituents may either be directly attached to $R^1$, or attached via an alkylene chain at an open position.

$R^2$, $R^3$ and $R^4$ are the same or different and are independently any of the groups set out for $R^1$ (and may be the same or different from $R^1$) and may optionally include one to five substituents which include any of the substituents set out for $R^1$.

The $R^2$, $R^3$ and/or $R^4$ groups can be attached to any of the carbons and/or to X which form the ring shown in formula I and, if desired, two of $R^2$, $R^3$ and/or $R^4$ may be attached to a single carbon atom.

The $R^1$, $R^2$, $R^3$ and/or $R^4$ may be joined together with the N atom and/or carbons to which they are attached to form a non-aromatic carbocyclic ring (namely, a cycloalkyl or cycloalkenyl ring), a cycloheteroalkyl ring or a heteroaryl ring, which contains 5 to 10 ring members, preferably 5 to 7 ring members. In addition, one of $R^2$, $R^3$ and $R^4$ can make a fused non-aromatic carbocyclic ring, namely a cycloalkyl ring or cycloalkenyl ring, with $R^1$ via linkage at the position adjacent to the linkage of X and $R^1$.

The group A

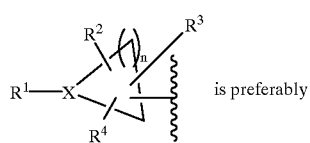

A is preferably

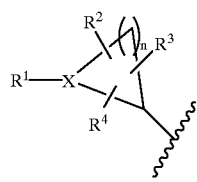

B thus may preferably include, but is not limited to, the following structures

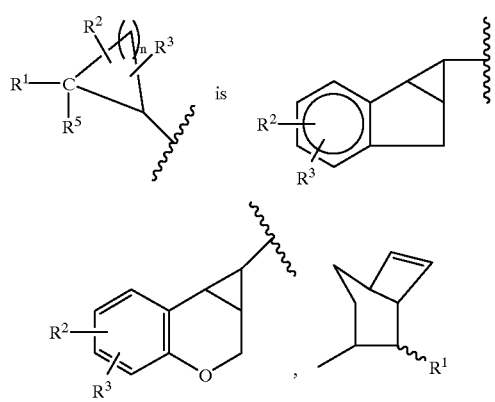

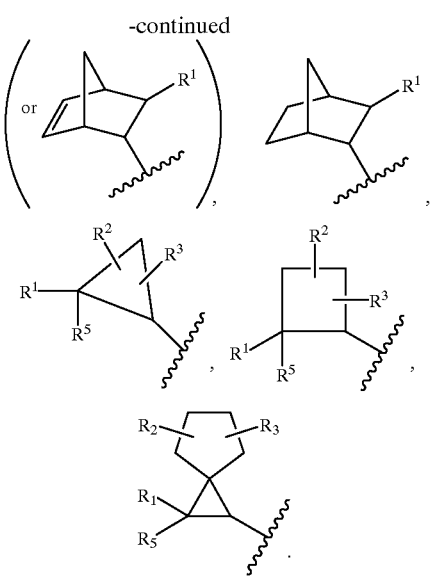

Thus, the compounds of formula I of the invention can have the following structural formulae:

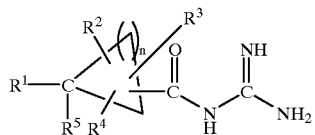

IA

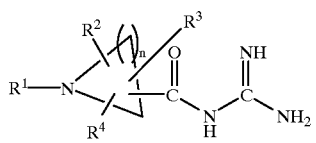

IB

It is preferred that at least one of $R^1$, $R^2$, $R^3$ and $R^4$ is aryl or heteroaryl.

It is also preferred that in IB (where X is N), $R^1$ is aryl or heteroaryl.

Preferred are compounds of formula I of the invention wherein n is 1, 2, 3 or 4, more preferably 1; preferably X is CH or N; more preferably, X is CH; preferably $R^2$ and $R^3$ are independently H, lower alkyl, lower alkoxy, or aryl; more preferably $R^2$ and $R^3$ are independently lower alkyl; and $R^4$ and $R^5$ are each H; and $R^1$ is aryl or heteroaryl such as phenyl, halophenyl, dihalophenyl, alkylphenyl, nitrophenyl, dialkoxyphenyl, trifluoromethylphenyl, biphenyl, alkylthiophenyl, trialkoxyphenyl, halo(dialkoxy)phenyl, phenylalkyl such as benzyl, 2,3-dihydrobenzofuran

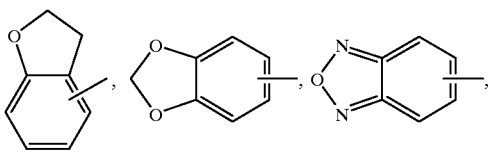

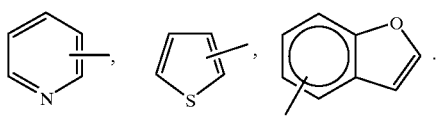

Specific preferred examples of $R^1$ groups include phenyl, substituted phenyl such as 4-bromophenyl, 4-chlorophenyl, 3-bromophenyl, 3,5-dimethoxyphenyl, 4-methylphenyl, 2,4-dichlorophenyl, 3-nitrophenyl, 2-chlorophenyl, 3-chlorophenyl, 2,5-dimethylphenyl, 2-methylphenyl, 3-mthylphenyl, 4-methylphenyl, 2,3-dimethoxy phenyl, 4-trifluoromethylphenyl, 3-trifluoromethoxyphenyl, 4-biphenyl, 2-bromo-4,5-dimethoxyphenyl, 4-methylthiophenyl, 3,4,5-trimethoxyphenyl, 4-fluorophenyl, 2-chloro-3,4-dimethoxyphenyl, 4-nitrophenyl, benzyl, 3-methoxyphenyl, 4-methoxyphenyl, 2-methoxyphenyl, 3-bromo-4-fluorophenyl, 3-ethoxyphenyl, 3-trifluoromethylphenyl, 3,5-difluorophenyl, 3,5-dichlorophenyl, 3,5-ditrifluoromethylphenyl, 4-fluorophenyl, 3-trifluorophenyl, 3-(N-pyrrolyl)-phenyl, 3-(N-pyrrolidinyl)phenyl, and 3-(N-pyrazolinyl)phenyl 3-(N-imidazolyl)phenyl. Other $R^1$ groups include

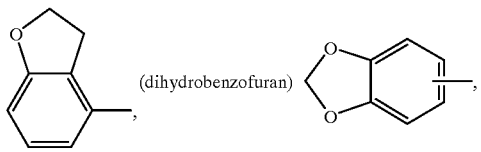

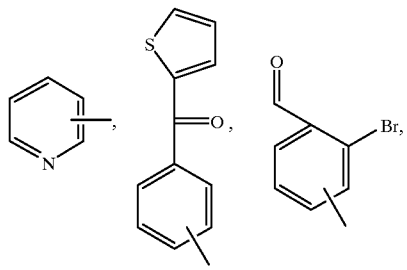

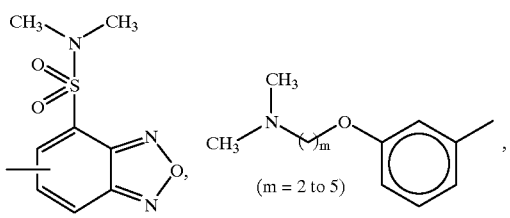

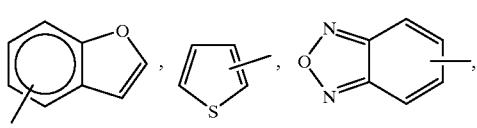

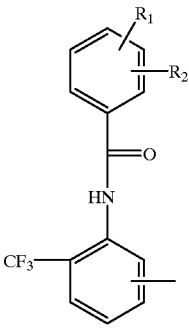

where $R_1$ and $R_2$ are independently H or Cl,

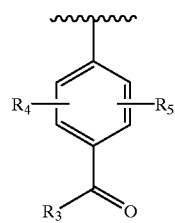

where $R_3$ is $NH_2$, $CH_3$, $CF_3$ and $R_4$ and $R_5$ are independently H, 2-F, 2,5-diF, 2-$CF_3$, 3-$CF_3$,

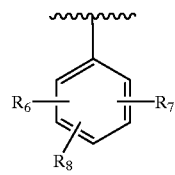

where $R_6$, $R_7$ and $R_8$ are independently H, 2-nitro, 2-$CF_3$, 3-$CF_3$, 3-CN—, 5-$CF_3$, 4-nitro, 4-O=CH—,

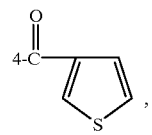

2-$CH_3O$—, 3-$CH_3O$—, 4-$CH_3O$—, 5-$CH_3O$—, 6-$CH_3O$—, 3-OH, 4-$(CH_3)_2N$—, 4-OH, 2-F, 3-F, 4-F, 5-F, 6-F, 4-isopropyl, 2-Br, 5-Br, 3-Br, 4-$CH_3SO_2$, 4-benzyloxy, 3-$CH_3CH_2$—, 2-$CH_3$—, 3-$CH_3$—, 6-$CH_3$—, 4-t-butyl, 4-$CH_3CH_2O$— 4-cyclohexyl, 4-phenoxy, 4-$CH_3$—$SO_2$—NH—,

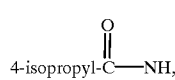

more preferably $R^1$ is dihydrobenzofuran.

In addition, in accordance with the present invention, a method for preventing, inhibiting or treating angina (stable or unstable), cardiac dysfunction, myocardial necrosis, and arrhythmia is provided, wherein a compound of formula I is administered in a therapeutically effective amount which inhibits sodium/proton exchange.

DETAILED DESCRIPTION OF THE INVENTION

The following definitions apply to the terms as used throughout this specification, unless otherwise limited in specific instances.

Unless otherwise indicated, the term "lower alkyl", "alkyl" or "alk" as employed herein alone or as part of another group includes both straight and branched chain hydrocarbons, containing 1 to 40 carbons, preferably 1 to 20 carbons, more preferably 1 to 12 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various additional branched chain isomers thereof, and the like as well as such groups including 1 to 4 substituents which may be any of the $R^1$ or the $R^1$ substituents set out herein.

Unless otherwise indicated, the term "cycloalkyl", as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 4 to 12 carbons, forming the ring and which may be fused to one aromatic ring as described for aryl, which include cyclopropyl, cyclobutyl, cyclopentyl, cyclohexyl, cycloheptyl, cyclooctyl, cyclodecyl and cyclododecyl, cyclohexenyl,

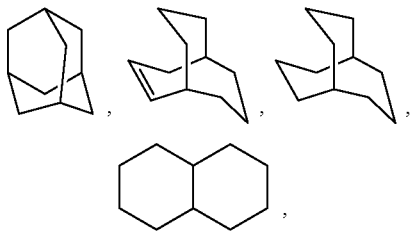

any of which groups may be optionally substituted with 1 to 4 substituents which may be any of the $R^1$ groups, or the $R^1$ substituents set out herein.

The term "cycloalkenyl" as employed herein alone or as part of another group refers to cyclic hydrocarbons containing 5 to 20 carbons, preferably 6 to 12 carbons and 1 or 2 double bonds. Exemplary cycloalkenyl groups include cyclopentenyl, cyclohexenyl, cycloheptenyl, cyclooctenyl, cyclohexadienyl, and cycloheptadienyl, which may be optionally substituted as defined for cycloalkyl.

The term "aryl" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings) and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkylalkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl or any of the $R^1$ groups or the $R^1$ substituents set out herein.

The term "aralkyl", "aryl-alkyl" or "aryllower alkyl" as used herein alone or as part of another group refers to alkyl groups as discussed above having an aryl substituent, such as benzyl or phenethyl, or naphthylpropyl, or an aryl as defined above.

The term "lower alkoxy", "alkoxy", "aryloxy" or "aralkoxy" as employed herein alone or as part of another group includes any of the above alkyl, aralkyl or aryl groups linked to an oxygen atom.

The term "amino" as employed herein alone or as part of another group may optionally be independently substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl or thioalkyl. These substituents may be further substituted with a carboxylic acid or any of the $R^1$ groups or $R^1$ substituents thereof as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl or hydroxy.

The term "lower alkylthio", alkylthio", "arylthio" or "aralkylthio" as employed herein alone or as part of another group includes any of the above alkyl, aralkyl or aryl groups linked to a sulfur atom.

The term "lower alkylamino", "alkylamino", "arylamino", or "arylalkylamino" as employed herein alone or as part of another group includes any of the above alkyl, aryl or arylalkyl groups linked to a nitrogen atom.

The term "acyl" as employed herein by itself or part of another group, as defined herein, refers to an organic radical linked to a carbonyl

group; examples of acyl groups include any of the $R^1$ groups attached to a carbonyl, such as alkanoyl, alkenoyl, aroyl, aralkanoyl, heteroaroyl, cycloalkanoyl, cycloheteroalkanoyl and the like.

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 20 carbons, preferably 3 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio or any of the $R^1$ groups, or the $R^1$ substituents set out herein.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, or any of the $R^1$ groups, or the $R^1$ substituents set out herein.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

Suitable alkylene, alkenylene or alkynylene groups $(CH_2)_p$ (where p is 1 to 8, preferably 1 to 5) (which may include alkylene, alkenylene or alkynylene groups) as defined herein, may optionally include 1, 2, or 3 substituents which include any of the $R^1$ groups, or the $R^1$ substituents set out herein.

Examples of alkylene, alkenylene and alkynylene include

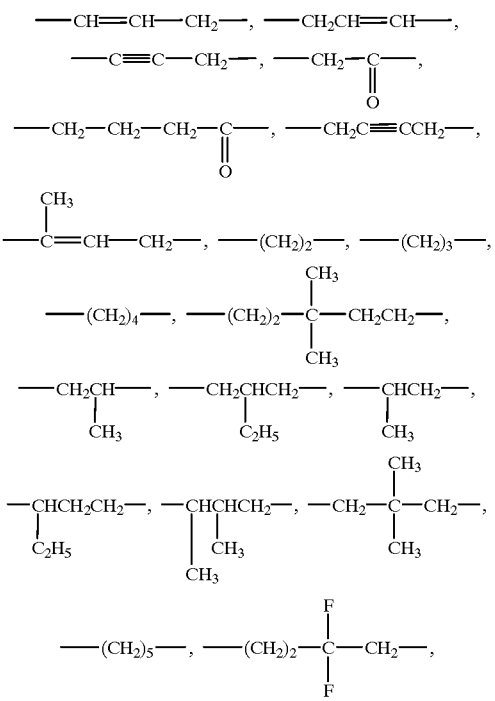

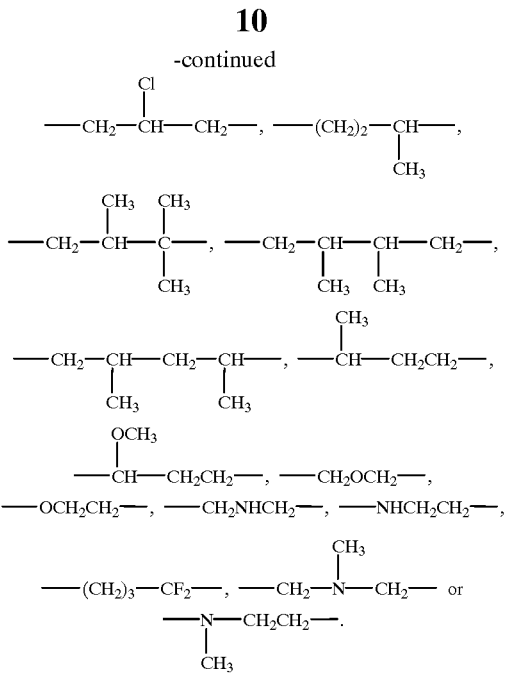

The term "halogen" or "halo" as used herein alone or as part of another group refers to chlorine, bromine, fluorine, and iodine as well as $CF_3$, with chlorine or fluorine being preferred.

The term "metal ion" refers to alkali metal ions such as sodium, potassium or lithium and alkaline earth metal ions such as magnesium and calcium, as well as zinc and aluminum.

The term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_p$ (which is defined above), such as

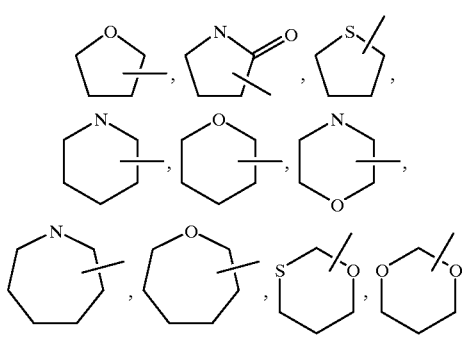

and the like. The above groups may include 1 to 4 substituents such as alkyl, halo, oxo and/or any of of the $R^1$ groups, or the $R^1$ substituents set out herein. In addition, any of the above rings can be fused to a cycloalkyl, aryl, heteroaryl or cycloheteroalkyl ring.

The term "heteroaryl" as used herein alone or as part of another group refers to a 5- or 6-membered aromatic ring which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), and includes possible N-oxides. The heteroaryl group may optionally include 1 to 4 substituents such as any of the R¹ groups or the R¹ substituents set out above. Examples of heteroaryl groups include the following:

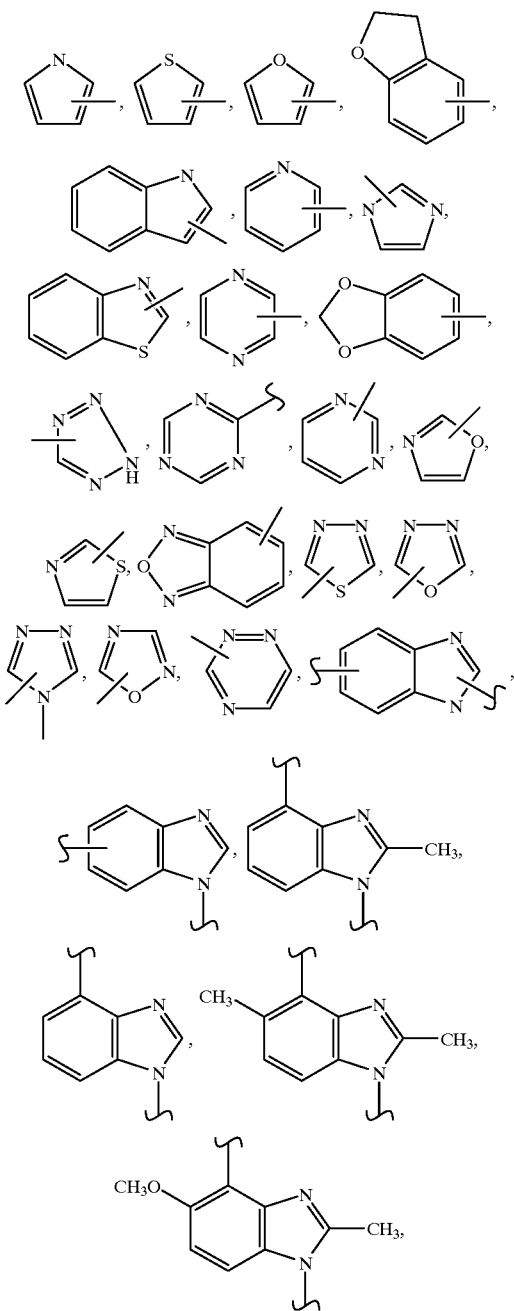

and the like.

The term "cycloheteroalkylalkyl" as used herein alone or as part of another gorup refers to cycloheteroalkyl groups as defined above linked through a C atom or heteroatom to a $(CH_2)_p$ chain.

The term "heteroarylalkyl" or "heteroarylalkenyl" as used herein alone or as part of another group refers to a heteroaryl group as defined above linked through a C atom or heteroatom to a —$(CH_2)_p$— chain, alkylene or alkenylene as defined above.

The term "polyhaloalkyl" as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "polyhaloalkyloxy" as used herein refers to an "alkoxy" or "alkyloxy" group as defined above which includes from 2 to 9, preferably from 2 to 5, halo substituents, such as F or Cl, preferably F, such as $CF_3CH_2O$, $CF_3O$ or $CF_3CF_2CH_2O$.

The compounds of formula I can be present as salts, in particular pharmaceutically acceptable salts. If the compounds of formula I have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as $(C_1–C_4)$-alkyl- or aryl-sulfonic acids which are unsubstituted or substituted, for example by halogen, for example methane- or p-toluenesulfonic acid. Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethyl-propylamine, or a mono-, di- or trihydroxy lower alkylamine, for example mono-, di- or triethanolamine. Corresponding internal salts may furthermore be formed. Salts which are unsuitable for pharmaceutical uses but which can be employed, for example, for the isolation or purification of free compounds I or their pharmaceutically acceptable salts, are also included.

Preferred salts of the compounds of formula I include monohydrochloride, hydrogensulfate, methanesulfonate, phosphate, nitrate or maleate.

All stereoisomers of the compounds of the instant invention are contemplated, either in admixture or in pure or substantially pure form. The compounds of the present invention can have asymmetric centers at any of the carbon atoms including any one of the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

It should be understood that the present invention includes prodrug forms of the compounds of formula I such as alkylesters of acids or any of the prodrugs for guanidines disclosed in U.S. application Ser. No. 08/641,718, filed May 2, 1996, and in U.S. Pat. No. 5,561,146 which are incorporated herein by reference.

The compounds of the instant invention may, for example, be in the free or hydrate form, and may be obtained by methods exemplified by the following descriptions.

The compounds of formula I may be prepared by the preferred processes described in the following reaction schemes. Exemplary reagents and procedures for these reactions appear hereinafter and in the working Examples.

Compounds of formula I of the invention can be prepared from the corresponding carboxylic acids by using the sequence of steps outlined in Scheme 1 set out below. Activation of carboxylic acid 1 with various activating reagents (e.g. 1,1'-carbonyldiimidazole (CDI), thionyl chloride, oxalyl chloride, and the like) (employing a molar ratio of activating agent:acid 1 within the range from about 1:1 to about 10:1) in an organic solvent such as THF or methylene chloride, convert acids 1 to 2. Subsequent treatment of compounds of formula 2 with guanidine in DMF or THF (employing a molar ratio of guanidine:2 within the range from about 1:1 to about 20:1) gives compounds of the formula I.

The carboxylic acids of formula 1 can either be commercially available or they can be prepared by methods known in the art.

Scheme 1

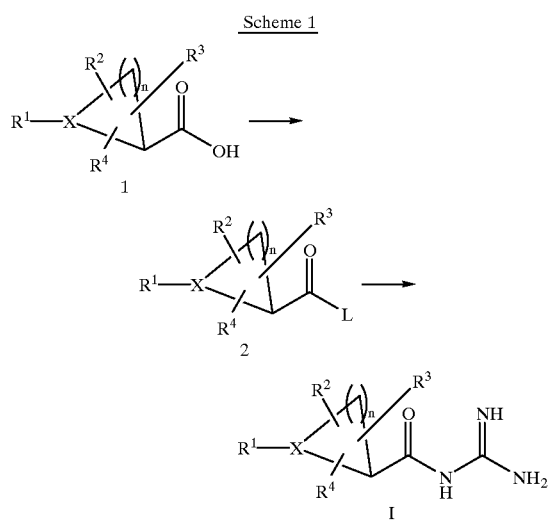

(L=a leaving group such as halide, alkoxy, aryloxy or imidazolyl).

Compounds of formula IA of the invention where n=1 and X is other than nitrogen (e.g., arylcyclopropanecarboxyl guanidines) can also be prepared from the corresponding α,β-unsaturated carboxylic acids or esters by using the sequence of steps outlined in Scheme 2 (employing a molar ratio of $CH_2N_2$:3 within the range from about 1:1 to about 20:1, and a molar ratio of guanidine:4 within the range from about 1:1 to about 20:1.

Scheme 2

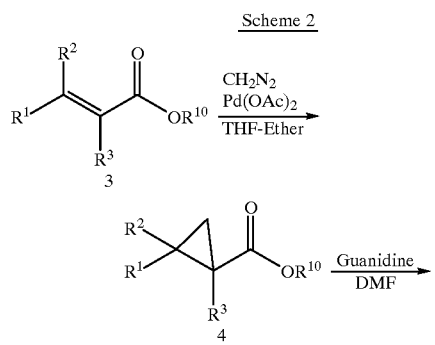

-continued

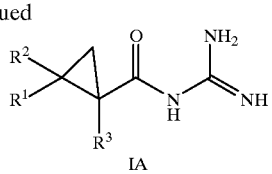

IA $R^{10}$=H, Me, Et, Pr, Bu, etc.

The acids or esters 3 used in this preparation are either commercially available or they can be prepared by methods known in the art. For example, 3-aryl-propenoic acids (6, $R^1$=aryl) can be prepared as outlined below. Condensation of malonic acid with the aldehydes in solvents such as pyridine with catalysts such as piperidine or pyrrolidine, gives the corresponding 4-aryl-propenoic acids. The starting aldehydes are either commercially available or they can be prepared by methods well known to those skilled in the art.

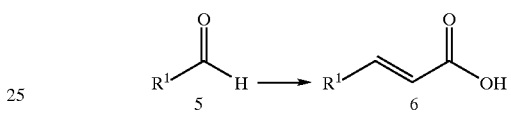

The compounds of formula IB of the invention where X is nitrogen can be prepared as in Scheme 3. Compound of formula 8 wherein L is a leaving group (halide, triflate, etc.) is treated with an amine of formula 7 (employing a molar ratio of 8:7 within the range from about 20:1 to about 1:20) in the presence of a base (e.g., triethylamine, and ethyldiisopropylamine) in an organic solvent (such as DMSO) to provide a compound of formula 9. Compound 9 is converted to the desired product IB by deprotection of the acid under appropriate conditions followed by coupling of the resulting acid 10 with guanidine (employing a molar ratio of guanidine:10 within the range from about 1:1 to about 20:1) utilizing a coupling agent such as 1,1'-carbonyldi-imidazole. The coupling of 7 and 8 to provide compounds of formula 9 can also be carried out in the presence of palladium catalysts by methods described in the literature (Wagaw, S. et al, J. Amer. Chem. Soc. 1997, Vol. 119, 8458 and references therein).

Compounds of formulae 7 and 8 are commercially available or they can be prepared by methods described in the literature.

Scheme 3

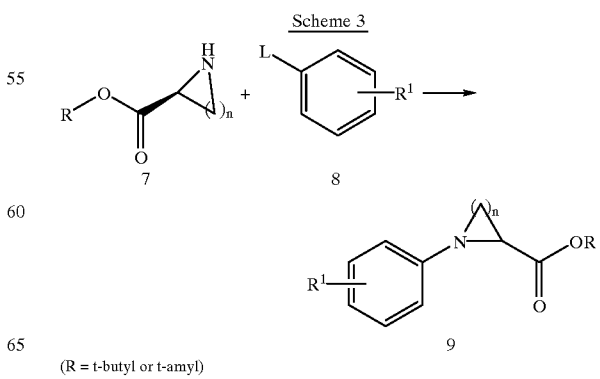

(R = t-butyl or t-amyl)

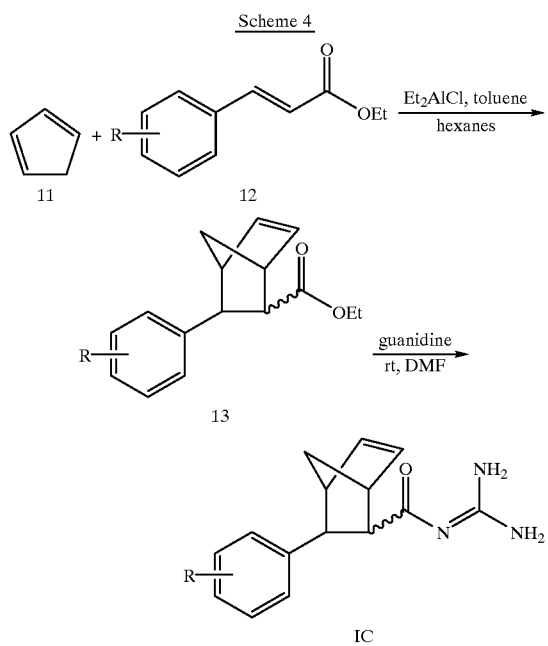

IB

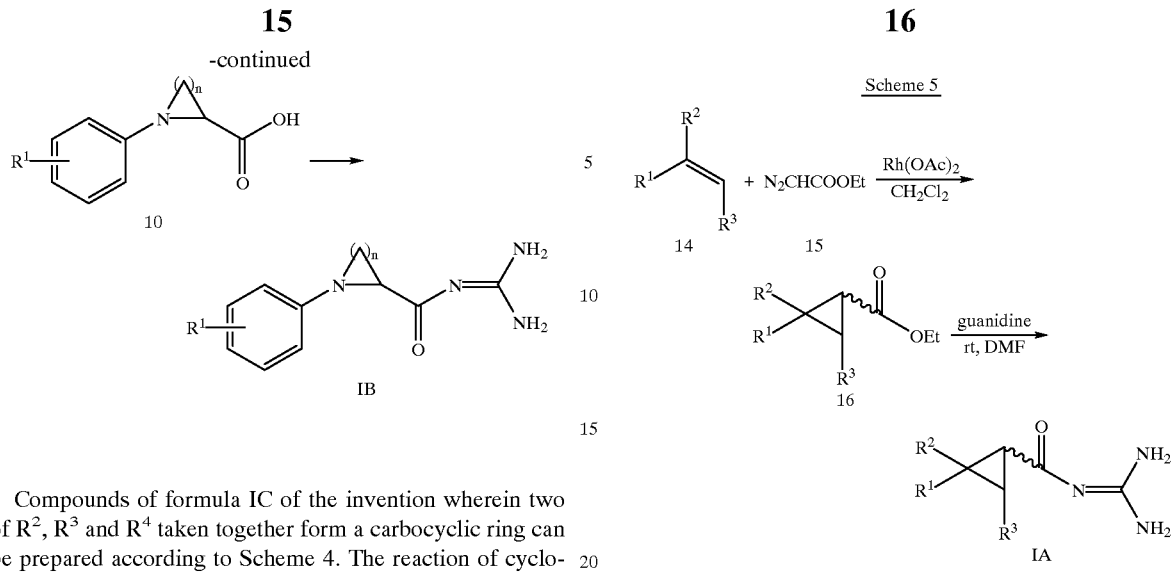

IA

Compounds of formula IC of the invention wherein two of $R^2$, $R^3$ and $R^4$ taken together form a carbocyclic ring can be prepared according to Scheme 4. The reaction of cyclopentadiene 11 with an unsaturated ester of formula 12 in the presence of a Lewis acid (diethylaluminum chloride, tin chloride etc.) gives compound of formula 13 which can be converted to the desired compounds of formula 1C by reacting with guanidine as described in Scheme 2. Compounds of formula 11 and 12 are commercially available or they can be prepared by methods described in the literature.

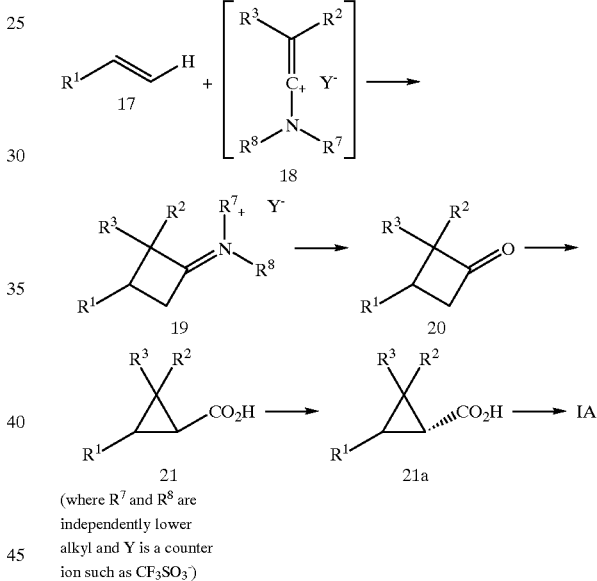

(where $R^7$ and $R^8$ are independently lower alkyl and Y is a counter ion such as $CF_3SO_3^-$)

IC

Compounds of formula IA of the invention wherein n=1 and X is other than nitrogen (e.g., arylcyclopropanecarboxy guanidines) can also be prepared according to Scheme 5. An olefin of formula 14 is reacted with ethyl diazoacetate (15) in the presence of a transition metal catalyst such as rhodium acetate, palladium acetate etc. to provide compounds of formula 16. Condensation of 16 with guanidine provides compounds of formula IA. Compounds of formulas 14 and 15 are commercially available or they can be prepared by standard methods described in the literature.

As set forth in Scheme 6, the process for the preparation of 2-(2',3'-dihydrobenzofuran-4'-yl)cyclopropane carboxylate (used as starting materials) involves the above chemical reactions.

The preparation of iminium salt 19 from olefin 17 and N,N-disubstituted ketene iminium salt 18 is carried out in a suitable solvent or solvent mixtures such as hydrocarbons, halogenated hydrocarbons, ethers, esters, ketones, amides and nitrites. The preferred solvent is dichloromethane. N,N-disubstituted ketene iminium salt 18 may be generated in situ by the reaction of an N,N-disubstituted amide with an acylating reagent such as acyl halides or anhydrides in the presence of a base choosing from aromatic or aliphatic bases. The preferred acylation reagent is trifluoromethanesulfonic anhydride and the preferred base is collidine. The N,N-disubstituted ketene iminium salt 18 may alternatively be generated in situ from an α-halo-N,N-disubstituted enamine such as α-chloro-N,N-disubstituted enamine with a Lewis acid such as zinc chloride. The reaction temperatures range from 0–150° C., with 30–100° C. being preferred. The preferred starting material is 4-vinyl-2,3-dihydrobenzofuran and the preferred ketene iminium salt precusors are N,N-dimethylacetamide and N,N-dimethylisobutyramide.

The preparation of cyclobutanone 20 from the corresponding iminium salt 19 by hydrolysis under aqueous conditions is carried out with the optional use of acid such as HCl or other conventional acid.

The preparation of acid 21 is carried out by generating the enolate of 20 using a base in a suitable solvent or solvent mixture followed by halogenation with a halogenating reagent to form the corresponding α-haloketone. The base used in this step includes LiHMDS, NaHMDS, KHMDS or any other base capable of enolyzing cyclobutanones. The preferred base is LiHMDS. A suitable solvent or solvent mixture includes ethers, hydrocarbons, or amides with the preferred solvent being THF. The temperature for the enolate formation may range from −110° to 50° C. with −80° to 25° C. being preferred. The halogenating reagent includes N-bromosuccinimide (NBS), N-chlorosuccinimide (NCS), N-iodosuccinimide (NIS), bromine, chlorine, iodine, dihalohydantoin or other electrophilic halogenating reagents with NBS being preferred.

Subsequent treatment of the α-haloketone with a base in a suitable solvent or solvent mixture forms 21. The base used in this step includes metal hydroxide or alkyloxide or aryloxide with metal hydroxide such as sodium hydroxide being preferred. The suitable solvent or solvent mixture may be any conventional solvent with the mixture of THF and water being preferred. The reaction temperature may range from −80° to 60° C. with −20° to 40° C. being preferred.

The resolution of 21 to form 21a is carried out by reaction of 21 with an appropriate chiral amine in a suitable solvent or solvent mixture to form the corresponding amine salt. The chiral amine includes conventional amines for resolution purpose with (R)-1-phenylethylamine preferred. The solvent or solvent mixture includes any conventional solvent with ethanol preferred. The temperature may range from 160° to −20° C. with 80° to 0° C. preferred.

The amine salt is converted to free acid 21a by reaction with aqueous acid in a suitable solvent or solvent mixture. The aqueous acid includes those acids that are stronger than the carboxylic acid 21 with aqueous HCl being preferred. A suitable solvent includes any conventional solvent with ethyl acetate being preferred. The acid 21a can be converted to compound IA of the invention by coupling 21a with guanidine in the presence of a coupling agent such as carbonyl diimidazole.

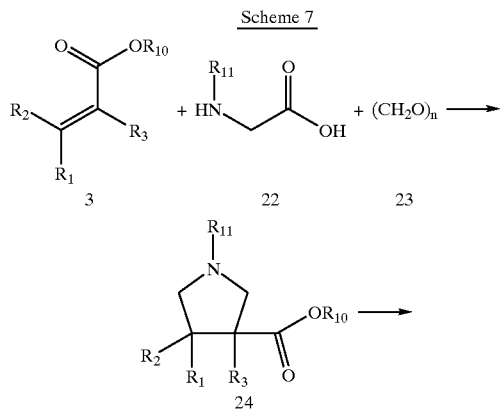

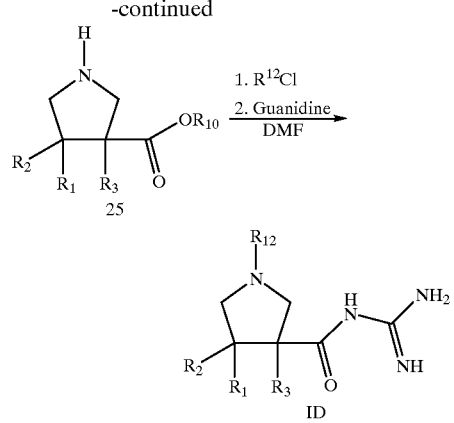

$R^{11}$=Aryl, lower alkyl, benzyl $R^{12}$=Aryl, lower alkyl, benzyl, arylcarbonyl, alkylcarbonyl, formyl, alkylaminocarbonyl, arylaminocarboynl Compounds of formula ID of the invention can be prepared as in Scheme 7. The reaction of unsaturated ester 3 with N-substituted glycine and paraformaldehyde gives compound of formula 24 which can be converted to the desired compound of formula ID of the invention by reacting with guanidine as described in Scheme 2.

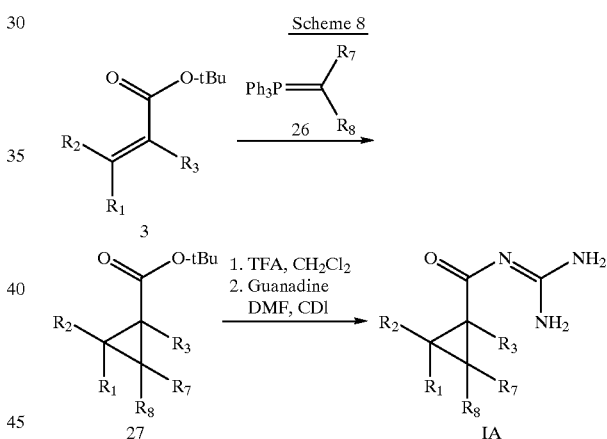

$R^7$ and $R^8$=lower alkyl, alkoxy or can be joined to form a cycloalkyl forming a 5,6 or 7 membered ring Compounds of formula IA of the invention can also be prepared as shown in Scheme 8. The reaction of an unsaturated ester such as 3 with an ylid such as 26 gives 27 which can be hydrolyzed to the corresponding acid and coupled with guanidine using an appropriate coupling reagent such as carbonyl diimidazole to give IA.

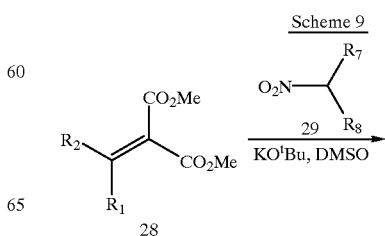

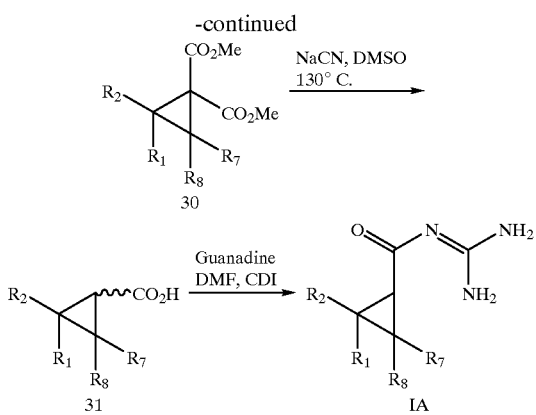

$R^7$ and $R^8$=lower alkyl or can be joined to form a cycloalkyl forming a 5,6 or 7 membered ring Compounds of formula IA of the invention can also be prepared as shown in Scheme 9. The reaction of an unsaturated ester such as 27 with compounds of type 29 gives 30 which can be decarboxylated to the corresponding acid 31 and coupled with guanidine using an appropriate coupling reagent such as carbonyl diimidazole to give IA.

Scheme 10

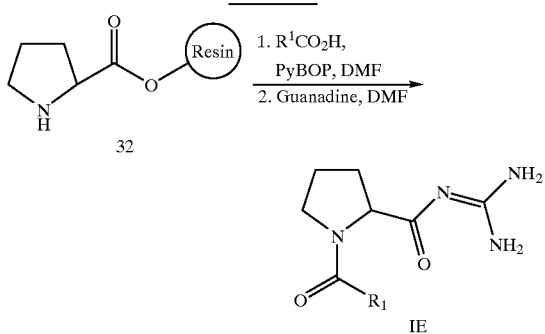

Compounds of formula IE of the invention can be prepared as shown in Scheme 10. The reaction of 32 with an appropriate carboxylic acid using an appropriate coupling reagent such as PyBOP followed by treatment with guanidine in an appropriate solvent such as DMF gives IE.

Scheme 11

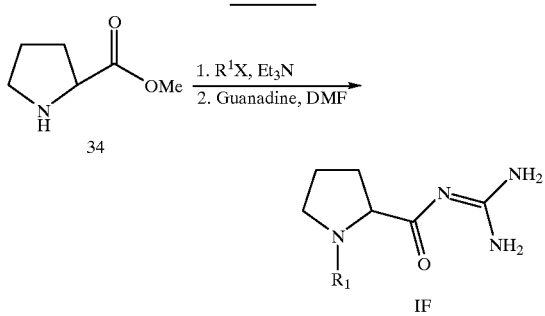

Compounds of formula IF of the invention can be prepared as shown in Scheme 11. The reaction of 34 with an appropriate alkylating agent in the presence of an appropriate base such as triethylamine followed by treatment with guanidine in an appropriate solvent such as DMF gives IF.

The above schemes as shown fix the position of the acyl guanidine moiety relative to the group B. However, it will be appreciated that these schemes apply to preparing compounds of formula I of the invention wherein the acyl guanidine moiety may be attached at any of the ring positions of the group A.

The compounds of formula I of the invention exhibit $Na^+/H^+$ exchange inhibitory activity, and hence, are useful for treating or preventing disorders caused by intracellular acidosis during myocardial ischemia, such as cardiac dysfunction, myocardial necrosis, arrhythmia, reperfusion injury, and the like which are observed in ischemic heart diseases (e.g., myocardial infarction and angina pectoris).

Thus, compounds of formula I of the invention may be used as antiischemic agents, i.e., for the treatment of ischemic conditions such as myocardial ischemia, cerebral ischemia, lower limb ischemia and the like. Thus, a composition containing one (or a combination) of the compounds of this invention, may be administered to a species of mammal (e.g., humans, dogs or cats) suffering from an ischemic condition.

A single dose, or two to four divided daily doses, provided on a basis of about 0.001 to about 100 mg per kilogram of body weight per day, preferably about 0.1 to about 25 mg per kilogram of body weight per day is appropriate. The substance is preferably administered orally, but parenteral routes such as the subcutaneous, intramuscular, intravenous or intraperitoneal routes or any other suitable delivery system, such as intranasal or transdermal routes can also be employed.

As a result of the $Na^+/H^+$ exchange inhibiting activity of the compounds of this invention, these compounds are also useful in the treatment of cardiovascular disorders. For example, compounds of the present invention are useful as therapy for congestive heart failure, therapy for peripheral vascular disorders (e.g. Raynaud's Disease), therapy for hypertension, as anti-anginal agents, as antifibrillatory agents, and in limiting myocardial infarction.

Compounds of the present invention are additionally expected to be useful in the treatment of cerebral ischemia (e.g., stroke).

As a result of the Na/H exchange inhibiting activity, the compounds of this invention can also be used for the treatment of diseases associated with proliferation of smooth muscle cells, mesangial cells, and fibroblasts. Such diseases include restenosis after angioplasty, renal fibrosis, atherosclerosis, hepatic fibrosis, prostate hypertrophy, pulmonary fibrosis and glomerular nephrosclerosis.

Other uses for compounds of this invention which inhibit Na/H exchange include treatments for diseases such as cardiac hypertrophy, ischemic/reperfusion injury associated with organ transplantation, and other surgical procedures such as percutaneous transluminal coronary angioplasty (PTCA).

Due to their Na/H exchange inhibiting properties, compounds of this invention can also be used for CNS disorders associated with cerebral ischemia such as cerebral infarction, cerebral edema and like. Additionally, they can be used for ischemia and ischemia-reperfusion injury resulting from shock and trauma.

The compounds of the invention are also anti-thrombotic agents and antiproliferative agents and are also useful in treating renal disease.

The compounds of the invention are also dual inhibitors of NHE-1 and NHE-3 and thus can be used as cardioprotectants for the treatment of heart disease, whilst also improving renal function by protecting against renal damage, or reversing hypertension by a direct modulation of sodium resorbtion in the kidney. As dual inhibitors, the compounds of the invention are also useful in a combination of therapies, for example, hypertension in patients with acute coronary syndromes, MI, recovery from MI and chronic stable angina. They are also useful for heart failure when an anti-hypertensive or diuretic agent is required for treatment.

Compounds of this invention can be additionally used for the treatment of diabetes mellitus and other diabetic complications and for lowering serum lipids such as lowering LDL-cholesterol.

The compounds of this invention can also be formulated in combination with a diuretic such as chlorothiazide, hydrochlorothiazide, flumethiazide, hydroflumethiazide, bendroflumethiazide, methylchlorthiazide, trichloromethiazide, polythiazide or benzthiazide as well as ethacrynic acid tricrynafen, chlorthalidone, furosemide, musolimine, bumetanide, triamterene, amiloride and spironolactone and salts of such compounds, angiotensin converting enzyme inhibitors such as captopril, zofenopril, fosinopril, enalapril, ceranopril, cilazopril, delapril, pentopril, quinapril, ramipril, lisinopril, and salts of such compounds, thrombolytic agents such as tissue plasminogen activator (tPA), recombinant tPA, streptokinase, urokinase, prourokinase, and anisoylated plasminogen streptokinase activator complex (APSAC, Eminase, Beecham Laboratories), or calcium channel blocking agents such as verapamil, nifedipine or diltiazem. Such combination products if formulated as a fixed dose employ the compounds of this invention within the dose range described above and the other pharmaceutically active agent within its approved dose range.

The compounds of formula I, and combinations thereof, can be formulated, as described above, in compositions such as tablets, capsules or elixirs for oral administration, in sterile solutions or suspensions for parenteral administration, and may also be administered via transdermal patch or nasal inhalation solutions. About 10 to about 500 milligrams of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples and preparations describe the manner and process of making and using the invention and are of preferred embodiments of the invention. It should be understood that there may be other embodiments which fall within the spirit and scope of the invention as defined by the claims appended hereto.

EXAMPLE 1 trans-N-(Aminoiminomethyl)-2-(4-methylphenyl) cyclopropanecarboxamide

A.

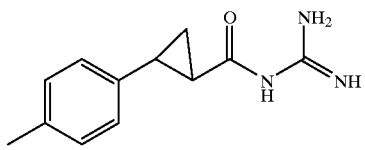

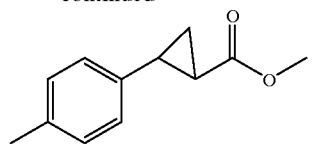

To a solution of trans-4-methylcinnamic acid

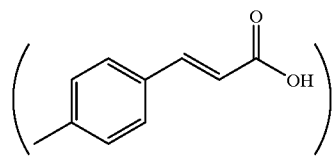

(81 mg, 0.5 mmol) in THF (10 mL) was added Pd(OAc)$_2$ (5 mg) in small portions followed by a cold (0° C.) ethereal diazomethane (CH$_2$N$_2$) solution [6 mL, prepared from 1,1-methyl-3-nitro-1-nitrosoguanidine (74 mg, 4.5 mmol)] with continuous stirring during 10–15 minutes. The addition of the diazomethane was done dropwise at 0° C. just following each addition of the palladium catalyst. A few drops of glacial acetic acid were added at the conclusion of the reaction to quench any unreactive diazomethane. The reaction mixture was filtered through a Celite bed and the cake was washed with fresh THF (2×10 mL). The filtrate was concentrated to give the title compound in the form of a dark oil (86 mg, 90% yield).

$^1$H NMR (270 MHz, CDCl$_3$)δ 7.08 (d, J=8.03 Hz, 2H); 6.98 (d, J=8.32 Hz, 2H); 3.70 (S, 3H); 2.5–2.45 (m, 1H); 2.30 (s, 3H); 1.85–1.84 (m, 1H); 1.60–1.55 (m, 1H); 1.32–1.25 (m, 1H).

B.

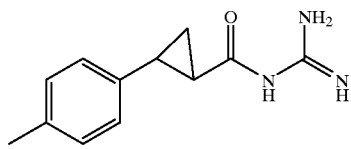

To a stirring solution of guanidine (148 mg, 2.5 mmol in DMF (1 mL) was added a solution of Part A compound in DMF (0.5 mL). Stirring was continued for 3 h at room temperature. Addition of water (2 mL) and extraction with ethyl acetate (2×5 mL), followed by evaporation of solvent afforded the crude product as a tan solid. The title compound was isolated as a TFA salt (white solid, 95 mg, 75% overall yield) from the preparative HPLC.

[Analytical HPLC: ret. time=2.83 min; 100% purity; LC/MS-m/e (M+H)$^+$218$^+$; $^1$H NMR (270b MHz; CD$_3$OD)δ 7.1 (d, J=8.2 Hz, 2H); 7.04 (d, J=8.2 Hz, 2H); 2.62–2.52 (m, 1H); 2.29 (s, 3H); 2.06–1.95 (m, 1H); 1.74–1.65 (m, 1H); 1.57–1.49 (m, 1H)].

EXAMPLE 2 trans-N-(Aminoiminomethyl)-2-(2,3-dihydro-4-benzofuranyl)cyclopropanecarboxamide

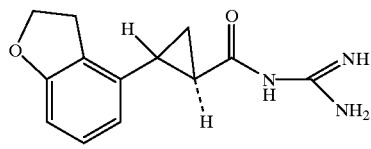

A. 2,3-Dihydrobenzofuran-4-carboxylic acid

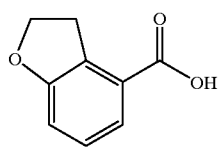

Benzofuran-4-carboxylic acid

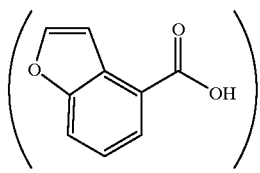

[Eissenstat, et al, J. Medicinal Chemistry, 38 (16) 3094–3105 (1995)] (10.0 g, 61.7 mmol) was hydrogenated (60 psi) in acetic acid (100 mL) over 10% Pd/C (2 g) for 12 hr. The mixture was filtered and the filtrate was diluted with water (500 mL) to give 2,3-dihydrobenzofuran-4-carboxylic acid as a white powder (8.4 g, 83%). A sample was recrystallized from isopropanol to give fine white needles (mp: 185.5–185.5° C.).

B. 2,3-Dihydrobenzofuran-4-methanol

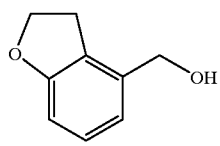

A solution of Part A 2,3-dihydrobenzofuran-4-carboxylic acid (10 g, 61 mmol) in THF (100 mL) was stirred as LAH (4.64 g, 122 mmol) was slowly added. The mixture was heated to reflux for 30 min. The mixture was cooled and quenched cautiously with ethyl acetate and then with 1N HCl (150 mL). The mixture was then made acidic with 12N HCl until all the inorganic precipitate dissolved. The organic layer was separated, and the inorganic layer was extracted twice with ethyl acetate. The organic layers were combined, washed twice with brine, and then concentrated in vacuo. This oil was distilled to give 2,3-dihydrobenzofuran-4-methanol as a clear oil that crystallized upon cooling (8.53 g, 87.6%).

C. 2,3-Dihydrobenzofuran-4-carboxaldehyde

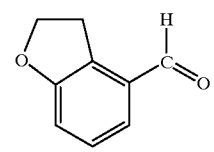

DMSO (8.10 mL, 114 mmol) was added at −78° C. to a stirred solution of oxalyl chloride in $CH_2Cl_2$ (40 mL of a 2M solution). A solution of Part B 2,3-dihydrobenzofuran-4-methanol (8.53 g, 56.9 mmol) in $CH_2Cl_2$ (35 mL) was added dropwise, and the solution stirred at −78° C. for 30 min. Triethylamine (33 mL, 228 mmol) was added cautiously to quench the reaction. The resulting suspension was stirred at room temperature for 30 min. and diluted with $CH_2Cl_2$ (100 mL). The organic layer was washed three times with water, and twice with brine, and then concentrated in vacuo to give 2,3-dihydrobenzofuran-4-carboxaldehyde as an oil (8.42 g, 100%) that was used without purification.

D. trans-3-(2,3-Dihydro-4-benzofuranyl)-2-propenoic acid

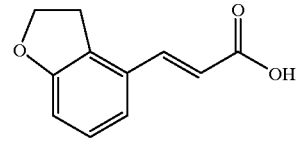

A solution of 2,3-dihydrobenzofuran-4-carboxaldehyde (8.42 g, 56.9 mmol) and malonic acid (11.86 g, 114 mmol) in pyridine (30 mL) and pyrrolidine (1 mL) was heated at reflux for 6 hr. The solution was cooled and poured into cold water (400 mL). The mixture was made strongly acidic with 12 N HCl to give a pale yellow precipitate that was filtered and air dried. The pale yellow powder was recrystallized from isopropanol to give white flakes (10.3 g, 95.3%, mp: 205–207° C.).

Anal. for $C_{11}H_{10}O_3$: Calc'd, C, 69.46; H, 5.30. Found, C, 69.36; H, 5.17. $^1$H NMR (300 MHz, $CDCl_3$)δ 7.76 (d, 1H, J=16.1 Hz), 7.15 (t, 1H, J=7.8 Hz), 7.07 (d, 1H, J=7.8 Hz), 6.81 (d, 1H, J=7.8 Hz), 6.37 (d, 1H, J=16.1 Hz), 4.62 (t, 2H, J=8.8 Hz), 3.33 (t, 2H, J=8.8 Hz).

E. trans-2-(2,3-Dihydro-4-benzofuranyl)cyclopropanecarboxylic acid, methyl ester

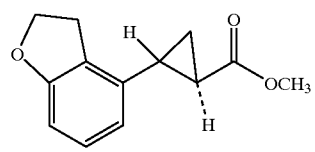

The title compound was prepared from title D compound by the same-procedure as described in Example 1, Part A.

F. trans-N-(Aminoiminomethyl)-2-(2,3-dihydro-4-benzofuranyl)-cyclopropanecarboxamide

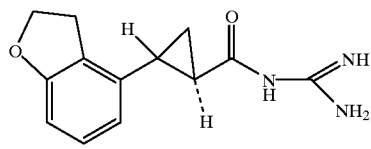

The title compound was prepared from the title E compound by the same procedure as described in Example 1, Part B.

EXAMPLE 3
(1S-trans)-N-(Aminoiminomethyl)-2-(2,3-dihydro-4-benzofuranyl)cyclopropanecarboxamide

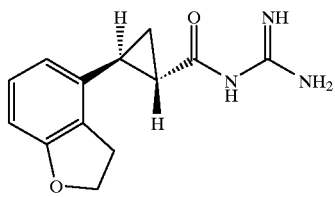

The title compound was prepared from the title compound of Example 2 (racemic mixture) by HPLC using Chiralpak-AD column with isopropanol:hexanes: triethylamine (10:90:0.2) as a mobile phase.

EXAMPLE 4
(1R-trans)-N-(Aminoiminomethyl)-2-(2,3-dihydro-4-benzofuranyl)cyclopropanecarboxamide

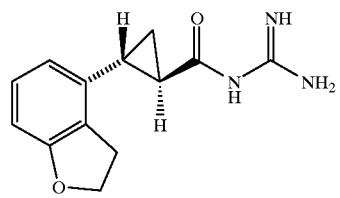

The title compound was prepared from the title compound of Example 2 (racemic mixture) by HPLC using Chiralpak-AD column and isopropanol:hexanes: triethylamine (10:90:0.2) as a mobile phase.

EXAMPLES 5 TO 48

The following compounds were prepared from the corresponding α,β-unsaturated acids or esters by the method described in Examples 1 and 2.

| Example No. | Structure | Characterization (MS) |
|---|---|---|
| 5 | 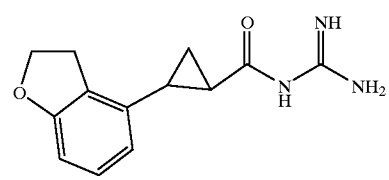 | $(M + H)^+ 246$ |
| 6 | 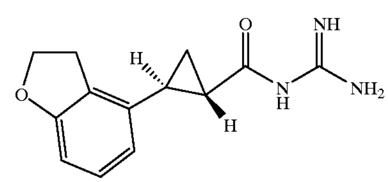 | $(M + H)^+ 246$ |
| 7 | 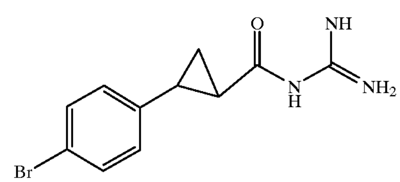 | $(M + H)^+ 282$ |
| 8 | 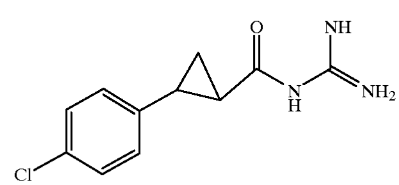 | $(M + H)^+ 237$ |

-continued

| Example No. | Structure | Characterization (MS) |
|---|---|---|
| 9 | 2-phenylcyclopropane-1-carbonyl guanidine | (M + H)⁺203 |
| 10 | 2-(3-bromophenyl)cyclopropane-1-carbonyl guanidine | (M + H)⁺282 |
| 11 | 2-(3,5-dimethoxyphenyl)cyclopropane-1-carbonyl guanidine | (M + H)⁺264 |
| 12 | 2-(6-bromo-1,3-benzodioxol-5-yl)cyclopropane-1-carbonyl guanidine | (M + H)⁺362 |
| 13 | 2-(4-methylphenyl)cyclopropane-1-carbonyl guanidine | (M + H)⁺218 |
| 14 | 2-(2,4-dichlorophenyl)cyclopropane-1-carbonyl guanidine | (M + H)⁺272 |
| 15 | 2-(3-nitrophenyl)cyclopropane-1-carbonyl guanidine | (M + H)⁺249 |
| 16 | 2-(3-chlorophenyl)cyclopropane-1-carbonyl guanidine | (M + H)⁺238 |

| Example No. | Structure | Characterization (MS) |
|---|---|---|
| 17 | 2-(2,3-dimethoxyphenyl)cyclopropyl guanidine carboxamide | (M + H)⁺264 |
| 18 | 2-(4-trifluoromethylphenyl)cyclopropyl guanidine carboxamide | (M + H)⁺272 |
| 19 | 2-(3-trifluoromethoxyphenyl)cyclopropyl guanidine carboxamide | (M + H)⁺288 |
| 20 | 2-(4-phenylphenyl)cyclopropyl guanidine carboxamide | (M + H)⁺280 |
| 21 | 2-(2-bromo-4,5-dimethoxyphenyl)cyclopropyl guanidine carboxamide | (M + H)⁺342 |
| 22 | 2-(benzo[d][1,3]dioxol-5-yl)cyclopropyl guanidine carboxamide | (M + H)⁺248 |
| 23 | 2-(4-methylthiophenyl)cyclopropyl guanidine carboxamide | (M + H)⁺250 |
| 24 | 2-(3,4,5-trimethoxyphenyl)cyclopropyl guanidine carboxamide | (M + H)⁺294 |

-continued

| Example No. | Structure | Characterization (MS) |
|---|---|---|
| 25 | 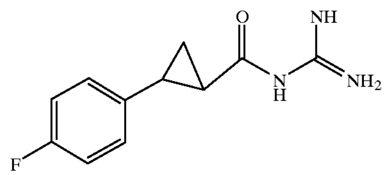 | (M + H)⁺222 |
| 26 | 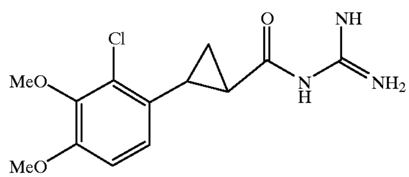 | (M + H)⁺298 |
| 27 | 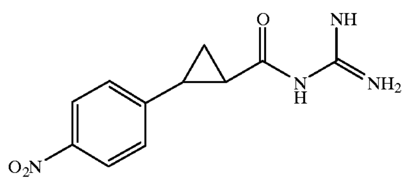 | (M + H)⁺249 |
| 28 | 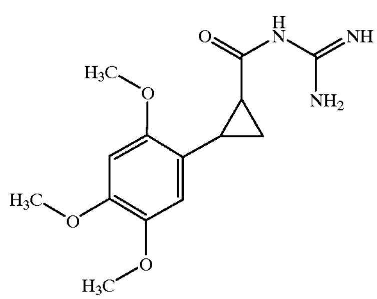 | (M + H)⁺294 |
| 29 | 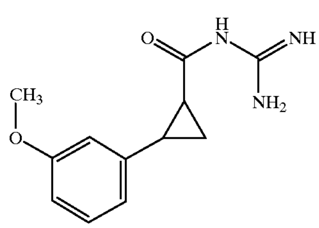 | (M + H)⁺234 |
| 30 | 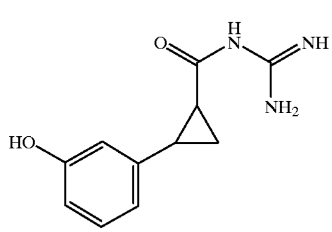 | M + H)⁺220 |

-continued

| Example No. | Structure | Characterization (MS) |
|---|---|---|
| 31 | 3-hydroxy-4-methoxyphenyl cyclopropyl carbonyl guanidine | (M + H)+250 |
| 32 | 4-(dimethylamino)phenyl cyclopropyl carbonyl guanidine | (M + H)+247 |
| 33 | 4-hydroxyphenyl cyclopropyl carbonyl guanidine | (M + H)+220 |
| 34 | 3-methoxy-4-hydroxyphenyl cyclopropyl carbonyl guanidine | (M + H)+250 |
| 35 | 2,5-difluorophenyl cyclopropyl carbonyl guanidine | (M + H)+240 |
| 36 | 2,6-difluorophenyl cyclopropyl carbonyl guanidine | (M + H)+240 |

-continued

| Example No. | Structure | Characterization (MS) |
|---|---|---|
| 37 | 3,4-difluorophenyl cyclopropyl carbonyl guanidine | (M + H)⁺240 |
| 38 | 3,5-difluorophenyl cyclopropyl carbonyl guanidine | (M + H)⁺240 |
| 39 | 4-isopropylphenyl cyclopropyl carbonyl guanidine | (M + H)⁺246 |
| 40 | 2,4-dimethoxyphenyl cyclopropyl carbonyl guanidine | (M + H)⁺264 |
| 41 | 5-bromo-2-methoxyphenyl cyclopropyl carbonyl guanidine | (M + H)⁺313 |

-continued
| Example No. | Structure | Characterization (MS) |
|---|---|---|
| 42 | 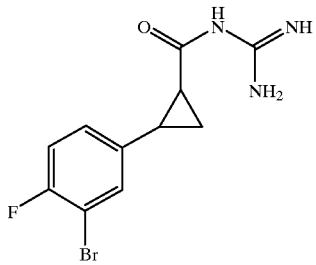 | (M + H)+301 |
| 43 | 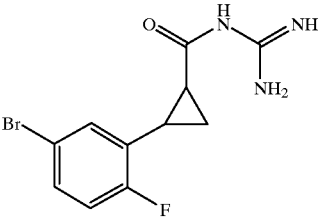 | (M + H)+301 |
| 44 | 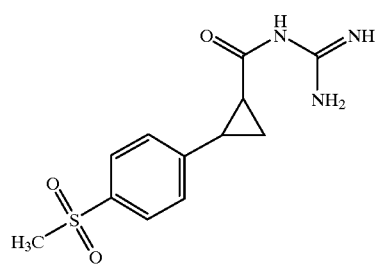 | (M + H)+282 |
| 45 | 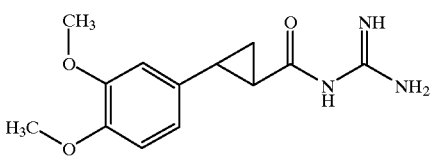 | (M + H)+264 |
| 46 | 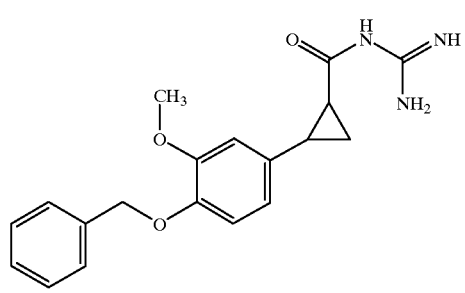 | (M + H)+340 |
| 47 | 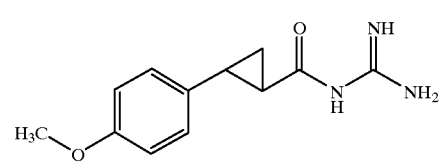 | (M + H)+234 |

-continued

| Example No. | Structure | Characterization (MS) |
|---|---|---|
| 48 | ![structure] | (M + H)⁺248 |
| 49 | ![structure] | (M + H)⁺246 |

(MS values: $(M+H)^+ 248$ for 48; $(M+H)^+ 246$ for 49.)

EXAMPLE 50 trans-N-(Aminoiminomethyl)-2-(2,5-dimethylphenyl)cyclopropanecarboxamide

B.

To a stirred solution of ethyl diazoacetate (0.105 mL, 1.0 mmol) and 2,5-dimethylstyrene (198 mg, 1.5 mmol) in 2 mL methylene chloride at −78° C. was added Pd(OAc)$_2$ (10 mg) and the reaction mixture was gradually allowed to come to RT over approximately 10 minutes. The mixture was concentrated to remove solvent and the resulting residue was treated with a solution of guanidine (295 mg, 5 mmol) in 2 mL DMF. The mixture was stirred at RT for 3 h and concentrated. The resulting crude brownish residue was shaken with 5 mL ethyl acetate to extract the soluble material and the ethyl acetate solution was added to a prepacked Varian Chem Elut™ 5 mL column, pretreated with 3 mL water. An additional 5 mL ethyl acetate was used to extract the column and the combined ethyl acetate eluate was concentrated. The residue was subjected to preparative HPLC (C18 column/90:10:0.1 to 10:90: 0.1 water-MeOH-TFA gradient) providing 13 mg of the title compound (as a trifluoroacetic acid salt), LRMS (M+H)⁺=232.

EXAMPLES 50A AND 50B

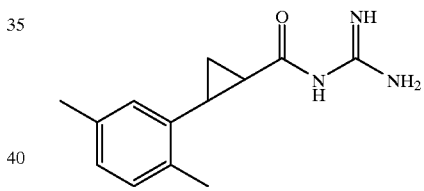

Chiral Enantiomer A and

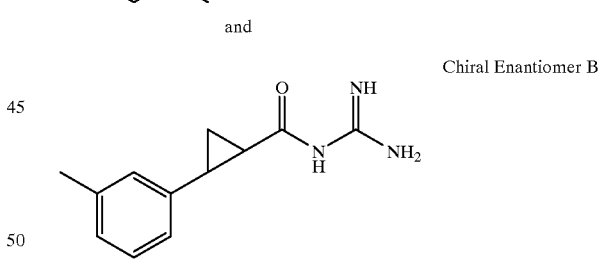

Chiral Enantiomer B

The Examples 49A and 49B compounds are prepared by resolving the racemic mixture from Example 49 by chiral chromatography (Chirapak AD column/hexanes-IPA-triethylamine 90:10:0.2). The title compound is eluted as the faster moving enantiomer, $[\alpha]_D + 218°$ C.=1 (MeOH).

EXAMPLES 51–67

The following compounds were prepared from the corresponding olefins using the procedure described above for Example 50.

| Example No. | Structure | Characterization (MS) |
|---|---|---|
| 51 | 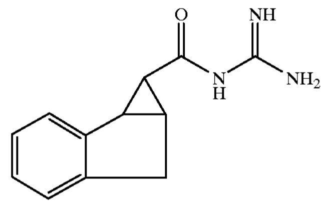 | (M + H)⁺216 |
| 52 | 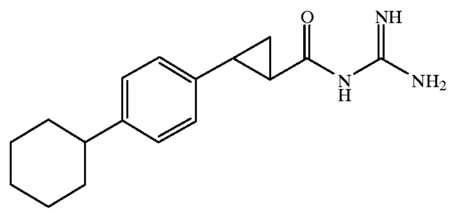 | (M + H)⁺286 |
| 53 | 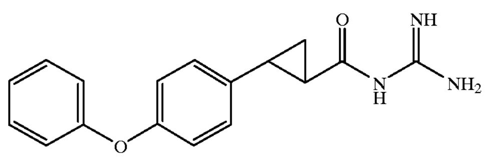 | (M + H)⁺296 |
| 54 | 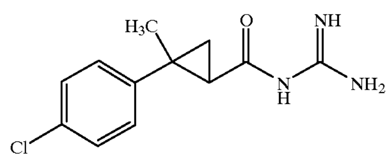 | (M + H)⁺252⁺ |
| 55 | 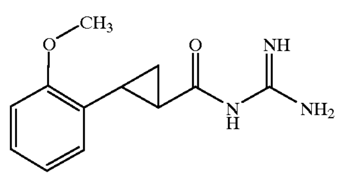 | (M + H)⁺234 |
| 56 | 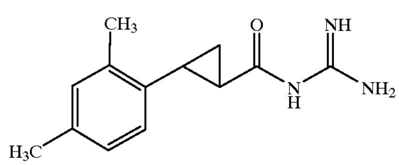 | (M + H)⁺232 |
| 57 | 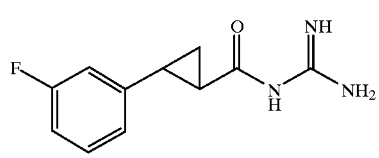 | (M + H)⁺222 |
| 58 | 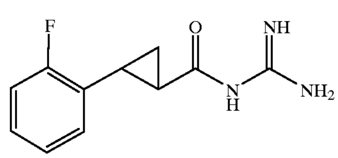 | (M + H)⁺222 |

-continued

| Example No. | Structure | Characterization (MS) |
|---|---|---|
| 59 | 4-ethoxyphenyl cyclopropyl C(O)NH-C(=NH)NH2 | (M + H)⁺248 |
| 60 | 3-methylphenyl cyclopropyl C(O)NH-C(=NH)NH2 | (M + H)⁺218 |
| 61 | 2-methylphenyl cyclopropyl C(O)NH-C(=NH)NH2 | (M + H)⁺218 |
| 62 | 4-methoxyphenyl cyclopropyl C(O)NH-C(=NH)NH2 | (M + H)⁺234 |
| 63 | 2,4,6-trimethylphenyl cyclopropyl C(O)NH-C(=NH)NH2 | (M + H)⁺246 |
| 64 | 3,4-dimethoxyphenyl cyclopropyl C(O)NH-C(=NH)NH2 | (M + H)⁺264 |
| 65 | 3,5-bis(trifluoromethyl)phenyl cyclopropyl C(O)NH-C(=NH)NH2 | (M + H)⁺340 |
| 66 | 2-(trifluoromethyl)phenyl cyclopropyl C(O)NH-C(=NH)NH2 | (M + H)⁺272 |

-continued

| Example No. | Structure | Characterization (MS) |
|---|---|---|
| 67 | 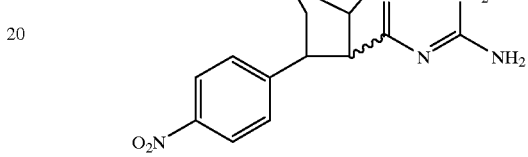 | (M + H)⁺272 |

EXAMPLE 68

A.

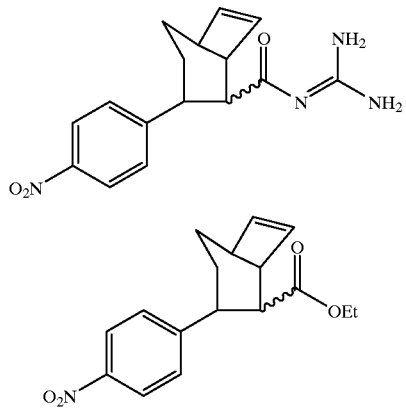

To a solution of ethyl 4-nitrocinnamate (0.5 g, 2.2 mmol) and cyclopentadiene (0.17 g, 2.7 mmol) in toluene (20 mL) was added 1M solution of diethylaluminum chloride (2.6 mL, 2.6 mmol) in hexane at −78° C. The resulting solution was stirred at −78° C. for 1.5 h and warmed to ambient temperature and stirred for 12 h. The solution was washed with IN NaOH solution, dried (MgSO$_4$) and concentrated. The residue was chromatographed on silica gel (ethyl acetate:hexanes/1:4) to give the desired product (0.39 g) as a 4:1 mixture of 2 isomers.

B.

To a solution of title A compound (0.20 g, 0.7 mmol) in DMF (5 mL) was added guanidine (0.2 g, 3.5 mmol) at ambient temperature. The resulting solution was stirred for 16 h at ambient temperature. The solution was diluted with ethyl acetate and washed with brine. The organic layer was dried (MgSO$_4$) and concentrated. The residue was purified by reverse phase preparative HPLC to give the desired product as a white solid. (M+H)⁺=301.

EXAMPLE 69–113

Using the procedure described in Example 68, the following compounds were prepared.

| Examples | Structure | Characterization MS |
|---|---|---|
| 69 isomer A | 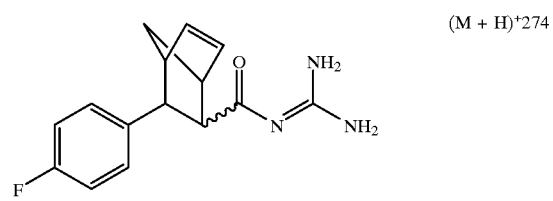 | (M + H)⁺274 |
| 70 isomer B | 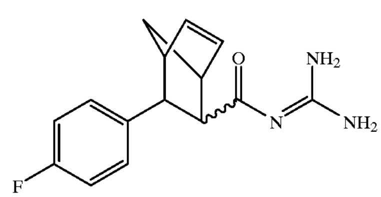 | (M + H)⁺274 |

-continued
| Examples | Structure | Characterization MS |
|---|---|---|
| 71 | 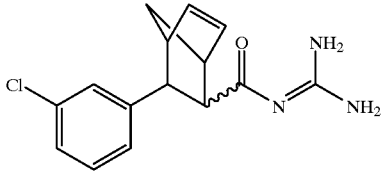 | (M + H)⁺290 |
| 72 | 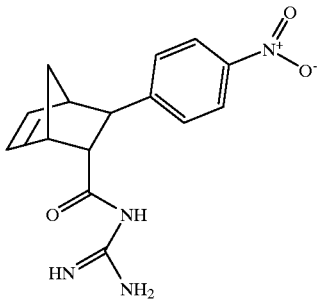 | (M + H)⁺301 |
| 73 | 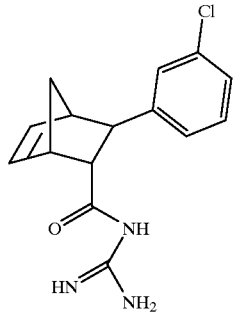 | (M + H)⁺291 |
| 74 | 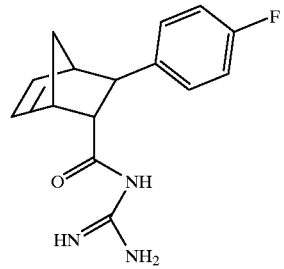 | (M + H)⁺274 |
| 75 | 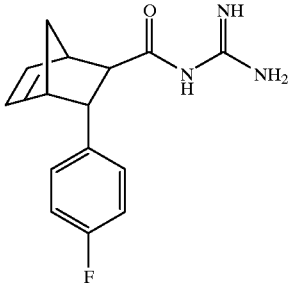 | (M + H)⁺274 |

-continued
| Examples | Structure | Characterization MS |
|---|---|---|
| 76 | 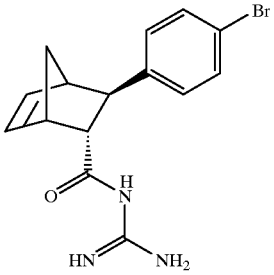 | (M + H)⁺335 |
| 77 | 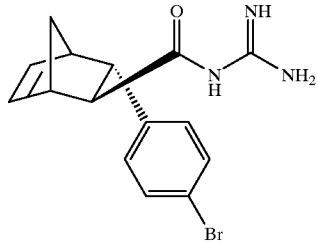 | (M + H)⁺335 |
| 78 | 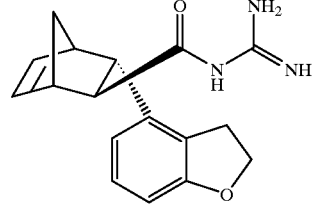 | (M + H)⁺298 |
| 79 | 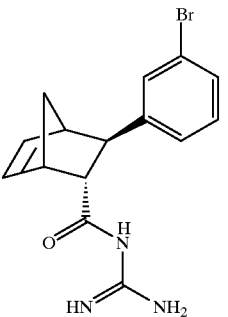 | (M + H)⁺335 |
| 80 | 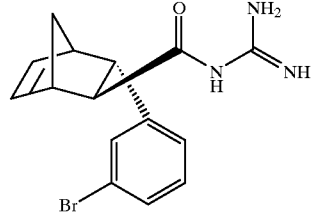 | (M + H)⁺335 |

-continued

| Examples | Structure | Characterization MS |
|---|---|---|
| 81 | 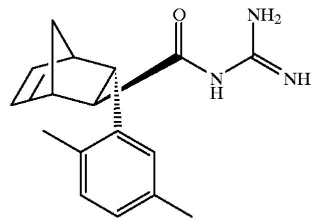 | (M + H)⁺284 |
| 82 | 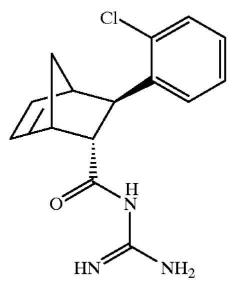 | (M + H)⁺291 |
| 83 | 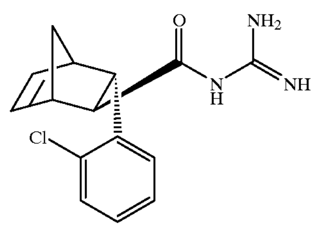 | (M + H)⁺291 |
| 84 | 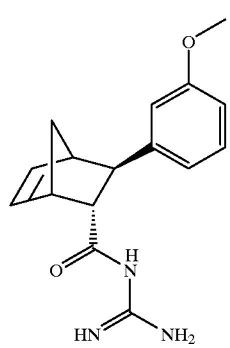 | (M + H)⁺286 |
| 85 | 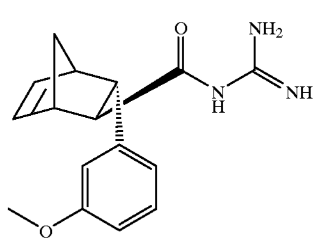 | (M + H)⁺286 |

-continued

| Examples | Structure | Characterization MS |
|---|---|---|
| 86 | 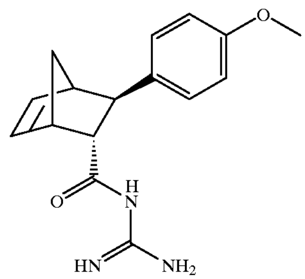 | (M + H)⁺286 |
| 87 | 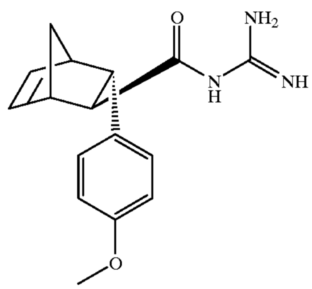 | (M + H)⁺286 |
| 88 | 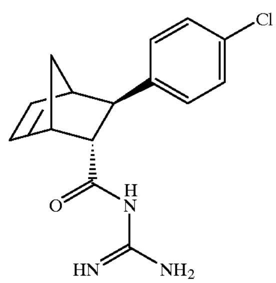 | (M + H)⁺291 |
| 89 | 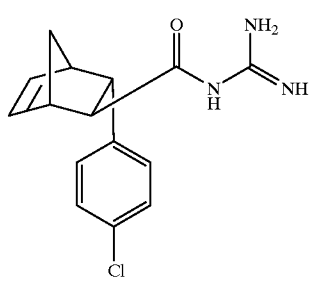 | (M + H)⁺291 |

-continued

| Examples | Structure | Characterization MS |
|---|---|---|
| 90 | 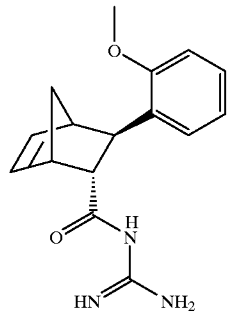 | (M + H)⁺286 |
| 91 | 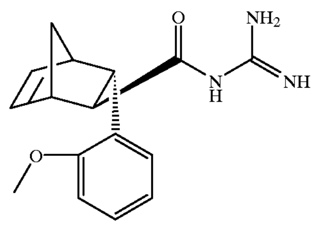 | (M + H)⁺286 |
| 92 | 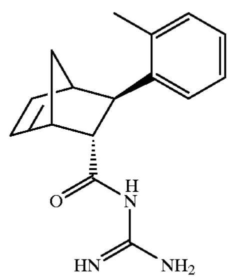 | (M + H)⁺270 |
| 93 | 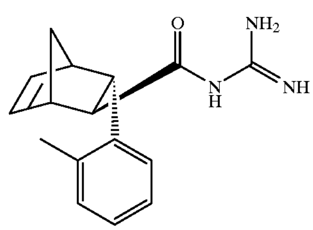 | (M + H)⁺270 |
| 94 | 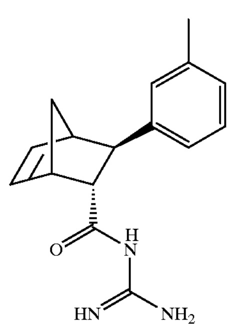 | (M + H)⁺270 |

-continued

| Examples | Structure | Characterization MS |
|---|---|---|
| 95 | 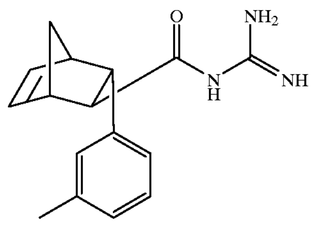 | (M + H)⁺270 |
| 96 | 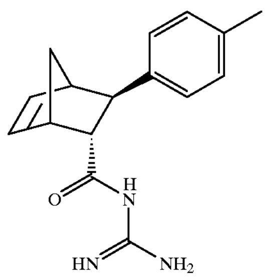 | (M + H)⁺270 |
| 97 | 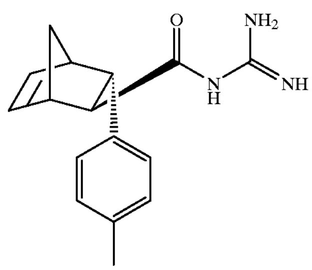 | (M + H)⁺270 |
| 98 | 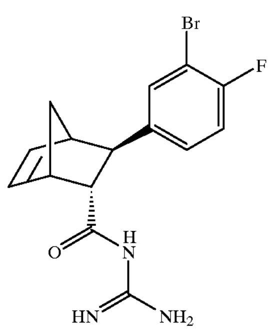 | (M + H)⁺353 |
| 99 | 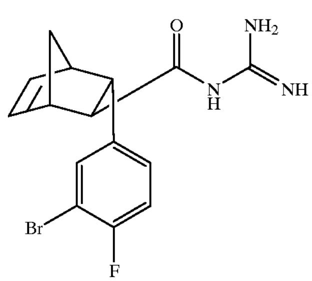 | (M + H)⁺353 |

-continued

| Examples | Structure | Characterization MS |
|---|---|---|
| 100 | 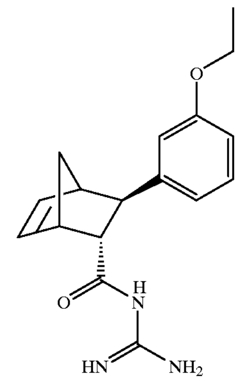 | (M + H)⁺300 |
| 101 | 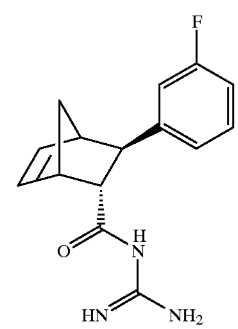 | (M + H)⁺274 |
| 102 | 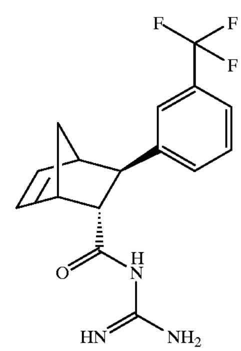 | (M + H)⁺324 |
| 103 | 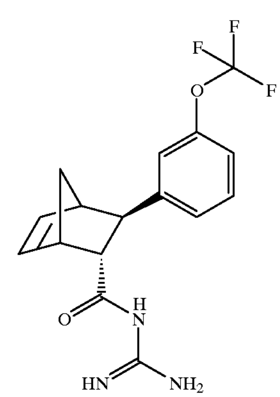 | (M + H)⁺340 |

-continued

| Examples | Structure | Characterization MS |
|---|---|---|
| 104 | 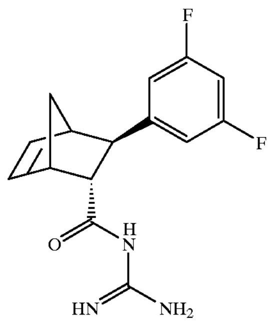 | (M + H)⁺292 |
| 105 | 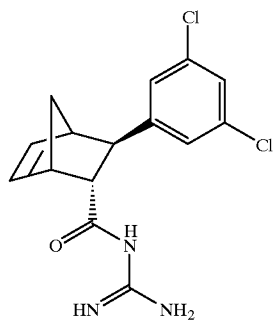 | (M + H)⁺325 |
| 106 | 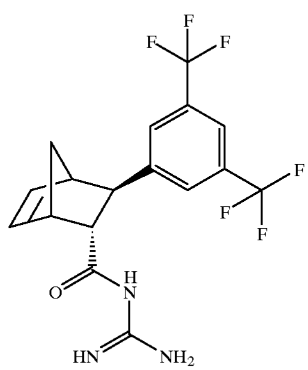 | (M + H)⁺392 |
| 107 | 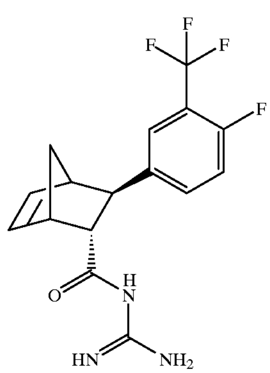 | (M + H)⁺342 |

-continued

| Examples | Structure | Characterization MS |
|---|---|---|
| 108 | 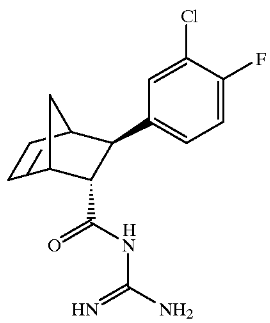 | (M + H)⁺309 |
| 109 | 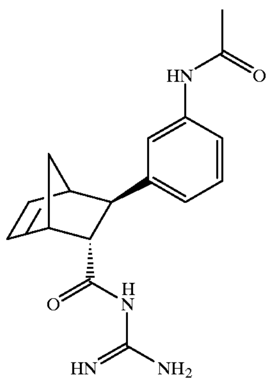 | (M + H)⁺313 |
| 110 | 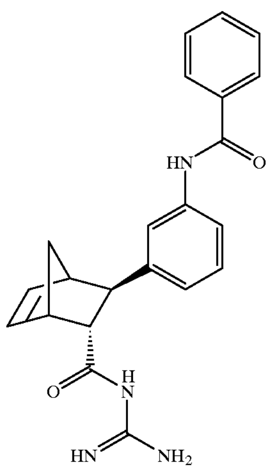 | (M + H)⁺375 |
| 111 | 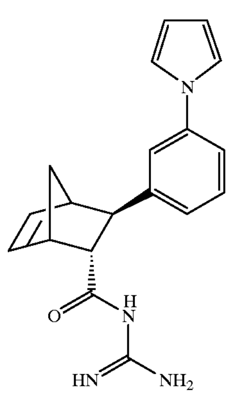 | (M + H)⁺321 |

| Examples | Structure | Characterization MS |
|---|---|---|
| 112 | 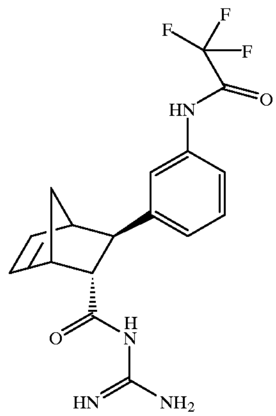 | (M + H)⁺367 |
| 113 | 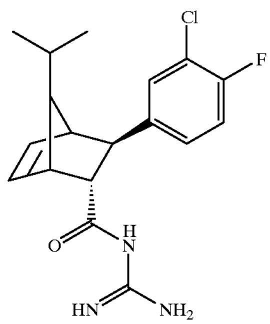 | (M + H)⁺351 |

EXAMPLE 114

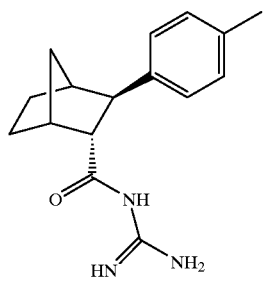

To a solution of the compound of Example 96 in methanol (20 mL) was added carbon on platinum. The resulting mixture was stirred at ambient temperature and ambient pressure of hydrogen for 4 hr and filtered. The filtrate was concentrated the residue was purified by reverse phase preparative HPLC to give the title product as a white powder (M+H)⁺=272.

EXAMPLES 115 TO 145

Following the procedure of Examples 68 and 114, the following compounds were prepared.

| Example | Structure | MW |
|---|---|---|
| 115 | 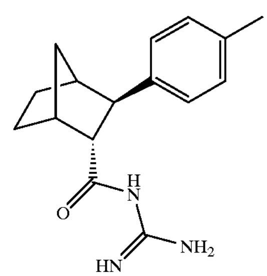 | (M + H)⁺ 272 |
| 116 | 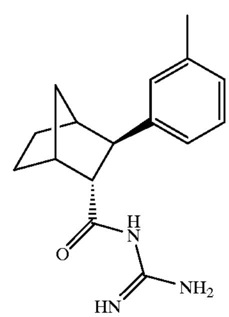 | (M + H)⁺ 272 |

-continued

| Example | Structure | MW |
|---------|-----------|-----|
| 117 | 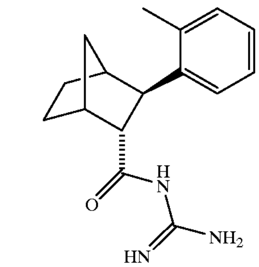 | (M + H)+ 272 |
| 118 | 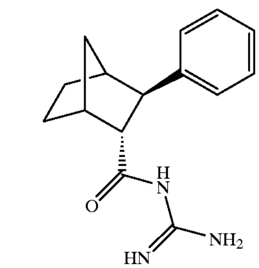 | (M + H)+ 258 |
| 119 | 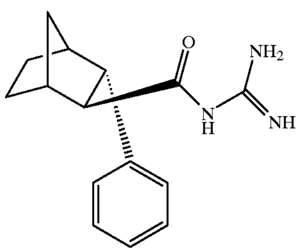 | (M + H)+ 258 |
| 120 | 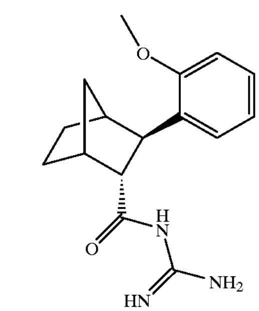 | (M + H)+ 288 |
| 121 | 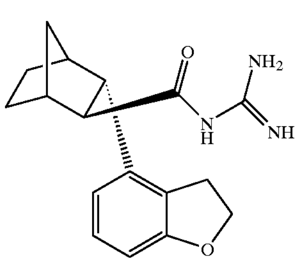 | (M + H)+ 300 |

-continued

| Example | Structure | MW |
|---------|-----------|-----|
| 122 | 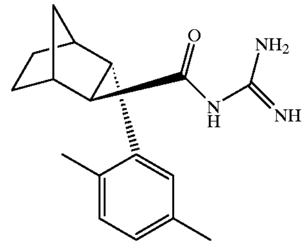 | (M + H)+ 286 |
| 123 | 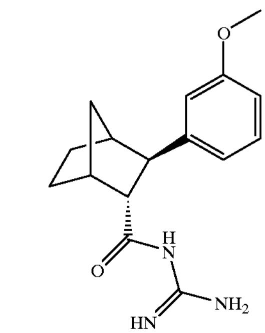 | (M + H)+ 288 |
| 124 | 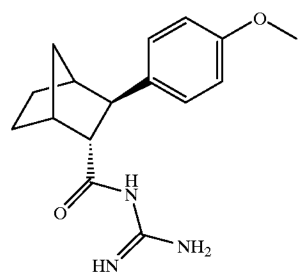 | (M + H)+ 288 |
| 125 | 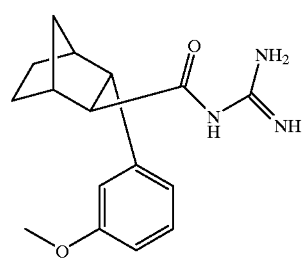 | (M + H)+ 288 |
| 126 | 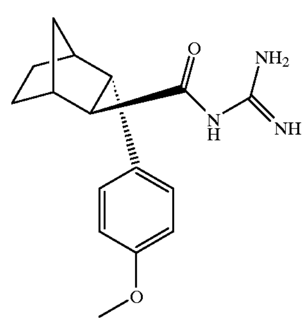 | (M + H)+ 288 |

| Example | Structure | MW |
|---|---|---|
| 127 | 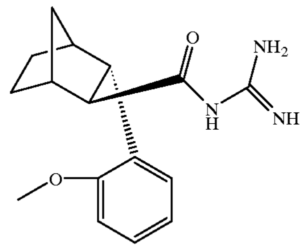 | (M + H)+ 288 |
| 128 | 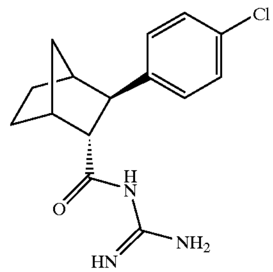 | (M + H)+ 293 |
| 129 | 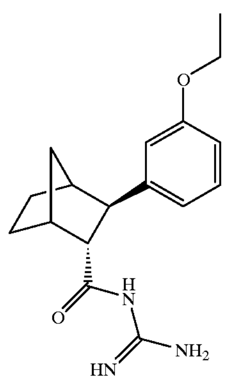 | (M + H)+ 302 |
| 130 | 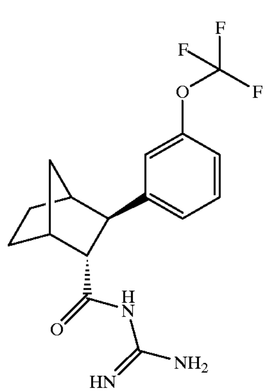 | (M + H)+ 342 |
| 131 | | (M + H)+ 355 |
| 132 | | (M + H)+ 276 |
| 133 | | (M + H)+ 326 |
| 134 | | (M + H)+ 294 |

-continued
| Example | Structure | MW |
|---|---|---|
| 135 | 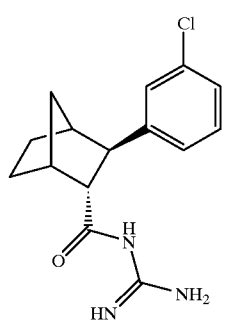 | (M + H)+ 293 |
| 136 | 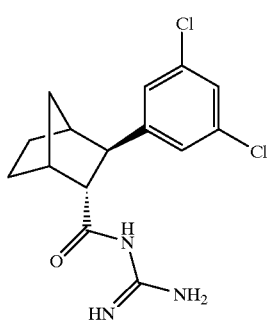 | (M + H)+ 327 |
| 137 | 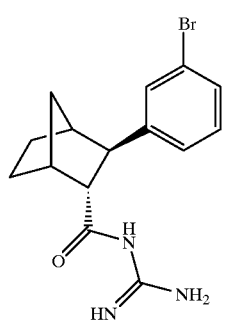 | (M + H)+ 337 |
| 138 | 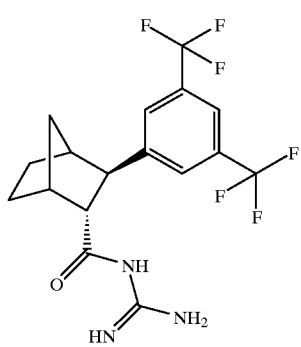 | (M + H)+ 394 |
-continued
| Example | Structure | MW |
|---|---|---|
| 139 | 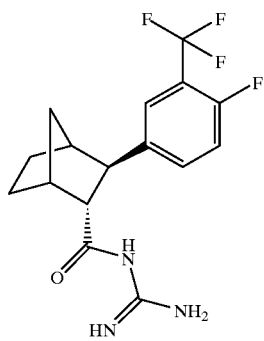 | (M + H)+ 344 |
| 140 | 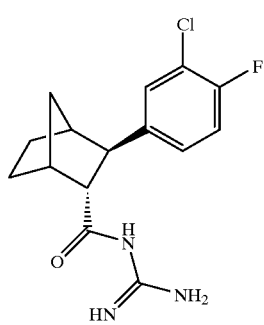 | (M + H)+ 311 |
| 141 | 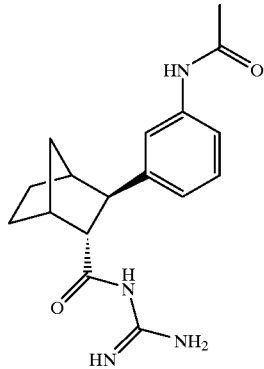 | (M + H)+ 315 |
| 142 | 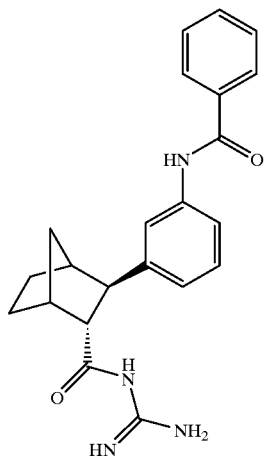 | (M + H)+ 377 |

73
-continued

| Example | Structure | MW |
|---|---|---|
| 143 | 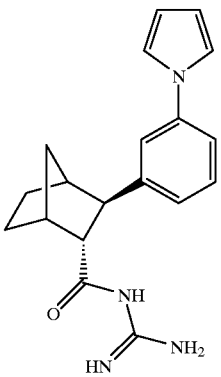 | (M + H)⁺ 323 |
| 145 | 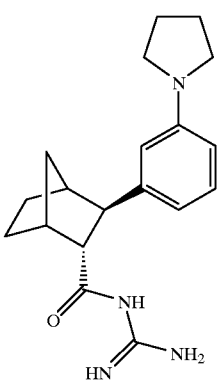 | (M + H)⁺ 327 |
| 145A | 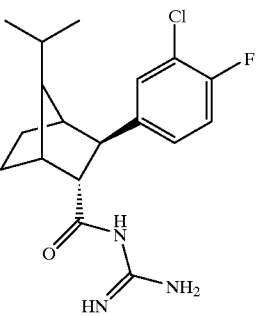 | (M + H)⁺ 353 |

EXAMPLE 146

A.

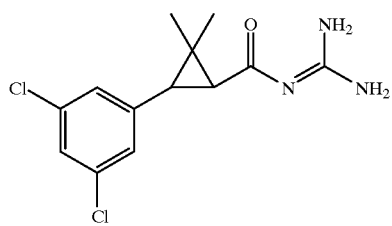

74
-continued

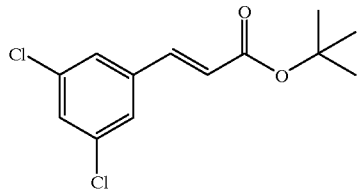

To a solution of tert-butyldiethylphosphonoacetate (6.94 g, 27.5 mmol) in THF (50 ml) at 0° C. was added slowly sodium hexamethyldisilazide (NaHMDS) (27.5 ml, 27.5 mmol).

The resulting solution was warmed to 25° C. and stirred 30 minutes. After cooling the reaction mixture to 0° C., a solution of 3,5-dichlorobenzaldehyde (4.38 g, 25 mmol) in THF (25 ml) was slowly added. The reaction mixture was warmed to 25° C. and stirred overnight. The reaction mixture was poured onto saturated NH₄Cl/EtOAc. The aqueous layer was extracted 3 times (×) with EtOAc. The combined organics were washed with brine, dried over Na₂SO₄, and concentrated in vacuo. Purification of the crude residue on silica gel (9:1 hexanes-EtOAc) provided 5.19 g (77%) of title compound in the form of a white solid.

B.

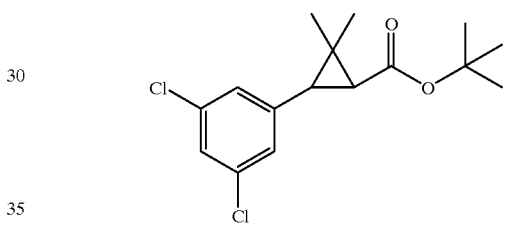

To a suspension of isopropyltriphenylphosphonium iodide (6.48 g, 15 mmol) in THF (45 ml) at −78° C. was added n-BuLi (2.5 M in hexanes, 6.6 ml, 16.5 mmol). The resulting mixture was warmed to 0° C. and stirred 30 minutes. To the reaction mixture was added a solution of tert-butyl-3,5-dichlorocinnamic ester (4.11 g, 15 mmol) in THF (30 ml). The reaction mixture was stirred 2 hours at 0° C., then slowly warmed to 25° C. and stirred overnight. The reaction mixture was poured onto 10% H₂SO₄/EtOAc. The aqueous layer was extracted 3× with EtOAc. The combined organics were washed with saturated NaHCO₃, brine, and H₂O, dried over NaSO₄, and concentrated in vacuo. The crude residue was used without further purification: ¹H NMR (CDCl₃) d 7.32 (1H, s) 7.30–7.27 (2H, m), 2.72 (1H, d, J=8.9 Hz), 2.28 (1H, d, J=8.9 Hz), 1.71 (9H, s), 1.51 (3H, s), 1.08 (3H, s).

C.

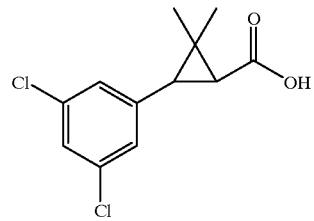

The crude ester from Step B (ca. 25 mmol) was dissolved in 1:1 trifluoroacetic acid-CH₂Cl₂ (25 ml) at 25° C. The resulting solution was stirred 1 hour at 25° C. The reaction mixture was concentrated in vacuo. The crude residue was partitioned between 10% NaOH and Et₂O. The aqueous layer was extracted 3× with ether. The pH of the aqueous layer was adjusted to 4 and was extracted 10× with EtOAc. The combined organics were dried over MgSO₄ and concentrated in vacuo to afford 2.32 g (71% over two steps) of a white solid: ¹H NMR (CDCl₃) d 7.32 (1H, s) 7.30–7.27 (2H, m), 2.77 (1H, d, J=8.9 Hz), 2.20 (1H, d, J=8.9 Hz), 1.48 (3H, s), 1.05 (3H, s).

D.

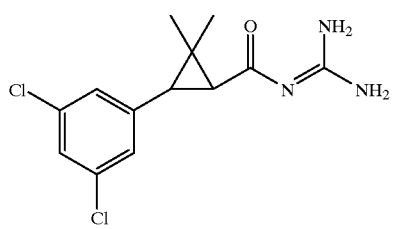

To a solution of acid from Step C (425 mg, 1.6 mmol) in DMF 5 ml at 25° C. was added carbonyldiimidazole (313 mg, 1.9 mmol). The resulting solution was stirred 1 hour at 25° C. To the reaction mixture was added guanidine carbonate (609 mg, 3.2 mmol). The reaction mixture was stirred overnight at 25° C. The reaction mixture was poured onto H₂O/EtOAc. The aqueous layer was extracted 3× with EtOAc. The combined organics were washed 2× with brine, dried over Na₂SO₄, and concentrated in vacuo to provide 373 mg (77%) of title compound in the form of a yellow oil. The crude product was separated into its two enantiomers (Chiralpak AD 5×50 cm, 9:1 hexanes-EtOH, 0.2% NEt₃, isocratic program): ¹H NMR (CDCl₃) d 9.02 (1H, bs), 7.71 (2H, bs), 7.37 (1H, s) 7.30–7.25 (2H, m), 2.72 (1H, d, J=8.9 Hz), 2.18 (1H, d, J=8.9 Hz), 1.48 (3H, s), 1.05 (3H, s); LCMS (M+1)=301.

EXAMPLE 147

A.

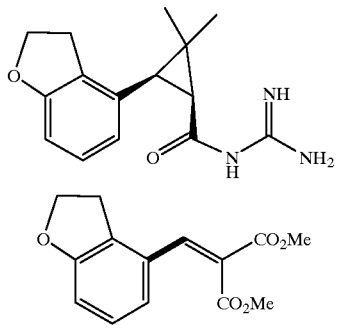

To a solution of 2,3-dihydrobenzofuran-4-aldehyde (1 g, 6.7 mmol) (Example 2, Part C) and dimethyl malonate 0.89 g, 6.7 mmol) in benzene (30 mL) was added piperidine (0.11 g, 1.4 mmol) and acetic acid (0.40 g, 6.7 mmol). The resulting solution was stirred for 18 hr with continuous removal of water. The solution was cooled to ambient temperature and concentrated. The residues was chromatographed on silica gel (ethyl acetat:hexane, 3:7) to give the title compound (1.5 g).

B.

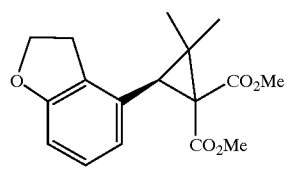

To a solution of Part A compound (1.3 g, 5.0 mmol) and 2-nitropropane (0.88 g, 9.9 mmol) in DMSO (20 mL) was added potassium t-butoxide (1.11 g, 9.9 mmol). The resulting mixture was stirred at ambient temperature for 65 hr and diluted with ethyl acetate. The solution was washed with 1N HCl. The organic layer was dried and concentrated. The residue was chromatographed on silica gel (ethyl acetate:hexane, 15:85) to give the title compound (0.82 g).

C.

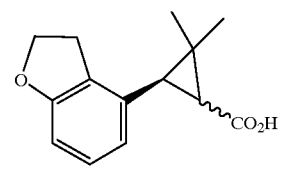

To a solution of Part B compound (0.1 g, 0.3 mmol) in DMSO (10 mL) was added sodium cyanide (32 mg, 0.65 mmol). The mixture was stirred for 4 hr at 15° C. and cooled to ambient temperature and diluted with ethyl acetate. The mixture was extracted with water. The aqueous layer was acidified with 1N HCl and extracted with ethyl acetate. The organic layer was dried and concentrated to give the title compound (45 mg) as 8 to 1 of trans to cis isomers.

D.

To a solution of Part C compound (45 mg, 02 mmol) in DMF (5 mL) was added carbonyl-diimidazole (38 mg, 0.2 mmol). The resulting solution was stirred for 1 hr at ambient temperature and guanidine (14 mg, 0.2 mmol) was added. The resulting solution was stirred for 16 hr at ambient temperature and diluted with ethyl acetate. The solution was washed with water. The organic layer was dried and concentrated. The residue was purified by reverse phase preparative HPLC to give the title compound (M+H)⁺=274.

EXAMPLE 148

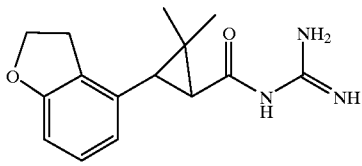

A.

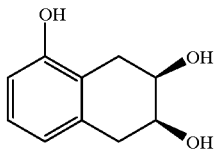

3a-9a-cis-3a,4,9,9a-Tetrahydro-2,2-dimethyl-2H-naphtho[2,3-d]-1,3-dioxol-5-ol (described in J. Med. Chem., 1978, 21, 913) (200 g, 0.908 mole), methanol (500 ml), and distilled water (170 mL) were charged in a 1000 mL three-neck round bottom flask equipped with a mechanical stirrer, a reflux condenser, and a digital thermometer probe at room temperature to obtain a suspension. Trifluoroacetic acid (15 mL) was added to the suspension with stirring. The suspension was heated to reflux at 62.5° C. for 3 hr. The reaction mixture was cooled to ambient temperature. A white suspension appeared. Methanol and trifluoroacetic acid were removed under reduced pressure. Water (360 mL) was added to the suspension with stirring. The suspension was then heated to 90° C. to dissolve the precipitate. The mixture was stirred for 30 min at 90° C. and allowed to cool to ambient temperature over 30 min and set aside at ambient temperature for 16 hr. The resulting crystals were filtered and washed with cold distilled water (100 mL). The crystals were dried in vacuo at room temperature overnight to give 155.9 g of the desired triol (95.3% yield) as gray needles.

B.

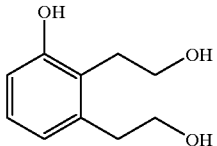

Part A triol (140 g, 777 mmol), tetrahydrofuran (330 mL) and distilled water (660 mL) were charged to a 2000 mL three-neck round bottom flask equipped with a mechanical stirrer and a digital thermometer at ambient temperature. A suspension was formed. The suspension was cooled to 0° C. by using an ice-water bath. Sodium periodate (179.47 g, 839 mmol) was added portionwise (~10 g each) over a period of 80 minutes. The reaction mixture was stirred for additional 40 minutes at 0° C. The precipitate was filtered and washed with ethanol (2×125 mL). The filtrate and the ethanol solutions were combined and saved.

Absolute ethanol (700 mL) in a 3000 mL three-neck round bottom flask equipped with a mechanical stirrer, a digital thermometer, and a pressure equalizing addition funnel was cooled to −6° C. by using a dry-ice acetone bath. Sodium borohydride (88.18 g, 2.331 mol) was added and the resulting suspension was stirred for 5 min at −6° C. To this was added the dialdehyde solution (1200 mL) in ethanol (from above) dropwise over a period of 80 minutes with the temperature maintained between −3 and 0° C. The mixture was stirred for additional 40 minutes at 0° C. Acetone (300 mL) was added dropwise to above solution over a period of 40 minutes and while keeping the temperature below 3° C.

The reaction mixture was stirred for additional 0.5 hrs below 3° C. It was then warmed to room temperature and stirred for 30 minutes.

Saturated ammonium chloride solution (500 mL) was then added at room temperature and the white precipitate was filtered and wash with ethanol (2×100 mL). The filtrate and the ethanol solutions were combined and the organic solvent removed under reduced pressure. Solid ammonium chloride (50 g) was added to the residue and the residue extract with ethyl acetate (5×400 mL). The combined organic layers were washed with 2:1 mixture of water:saturated sodium hydrogensulfite (300 mL), 1:1 mixture of water:brine (300 mL), and brine (2×300 mL). The organic phase was dried over magnesium sulfate and filtered. The solvent was removed under reduced pressure to give 136.13 g of the desired compound in 94.8% yield.

C.

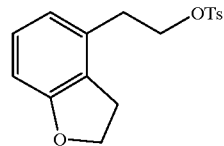

Part B triol (134 g, 735 mmol), pyridine (250 mL), and dichloromethane (350 mL) were charged in a 2000 mL three-neck round bottom flask equipped with a mechanical stirrer, a digital thermometer, and a pressure equalizing addition funnel at room temperature. The mixture was cooled to −40° C. by a dry-ice acetone bath. To this was added a solution of tosyl chloride (274.78 g, 1.442 mol) in pyridine (70 mL) and dichloromethane (400 mL) over a period of 170 minutes at −40° C. with good stirring. The mixture was stirred for an additional 3.5 hr at −35° C. Additional tosyl chloride (16.81 g, 88.2 mmol) was then added to the reaction mixture at −40° C. and the reaction mixture stirred for 30 minutes. The reaction mixture was warmed to −10° C. and dichloromethane (1500 mL) was added at −10° C. The reaction mixture was warmed to room temperature, washed with 2N HCl (4×650 mL), saturated NaHCO₃ (650 mL), brine (650 mL), dry over Na₂SO₄, and filtered. Solvent was removed under reduced pressure to give 360 g of crude ditosylate as a light yellowish residue which was used for the next step without any purification.

The crude ditosylate and methanol (2000 mL) were charged in a 3000 mL three-neck round bottom flask equipped with a mechanical stirrer, a digital thermometer, and a pressure equalizing addition funnel. The mixture was cooled to 0° C. by an ice-water bath. Anhydrous potassium carbonate (111.74 g, 809 mmol) was added portionwise to the methanol solution at 0° C. and the reaction mixture stirred at 0° C. for 2 hr. The reaction mixture was warmed to room temperature and stirred for additional 2 hr. The white precipitate was filtered and washed with ethyl acetate (2×100 mL). The filtrates were combined and concentrated to ~500 mL. The resulting precipitate was filtered and washed with 1:1 methanol:water (100 mL). The residue was dried in vacuum (~1 mmHg) for 3.5 hrs and over house vacuum overnight to give the desired compound (197.0 g, 84% yield).

D.

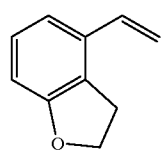

The Part C tosylate (100 g, 314 mmol) was dissolved in THF (1200 mL) in a 2000 mL three-neck round bottomed flask equipped with a mechanical stirrer, a digital thermometer, and a pressure equalizing addition funnel at room temperature. The reaction mixture was cooled to 0° C. by an ice-water bath. To this was added a solution of t-BuOK (1 M, 345.5 mL) in THF dropwise at 0° C. over a period of 110 min. The reaction mixture was warmed to ambient temperature and stirred for additional 2 hr. Water (350 mL) and EtOAc (600 mL) were added and the two layers were separated. The aqueous layer was further extracted with EtOAc (2×150 mL). The combined EtOAc layers were washed with brine (2×150 mL) dried over $MgSO_4$ and filtered. The solvent was removed under reduced pressure to give 46 g of the title styrene in 100% yield.

E.

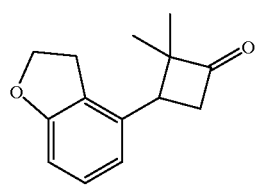

To a flame-dried 1L three necked round bottom flask equipped with a magnetic stirrer was added N,N, 2-trimethyl propionamide (17.8 mL, 0.138 mol) and anhydrous methylene chloride (200 mL). The mixture was stirred to give a solution under argon and cooled to −15° C. Trifluoromethanesulfonic anhydride (26 mL, 0.154 mol) was added via syringe and the resulting mixture was stirred at −15° C. for 10 minutes. A solution of

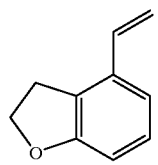

(from Part D)(17.5 g, 0.12 mol), and collidine (21 mL, 0.155 mol) in anhydrous methylene chloride (30 mL) was added at −15° C. After the addition was completed, the reaction mixture was heated to reflux and stirred for 20 hours. The solvent was removed on a rotary evaporator and the residue oil was washed with ether (3×100 mL) The residue was then dissolved in methylene chloride (150 mL). Water (150 mL) was added and the mixture was refluxed for 6 hours. After cooling to room temperature, the phases were separated. The aqueous layer was extracted with methylene chloride (2×100 mL). The rich organic layers were combined, washed with brine (200 mL) and dried over anhydrous sodium sulfate. After removal of sodium sulfate by filtration, the filtrate was concentrated to give an oil which was purified by silica gel chromatography using 5–10% EtOAc/hexane as the eluent to give 19.0 g (73%) title compound as a white crystalline compound. HPLC, 100A% at 220 nm. $^1$H NMR ($CDCl_3$) d, 7.14 (t, J=7.8 Hz, 1H), 6.72 (t, J=8.2 Hz, 2H), 4.52–4.65 (m, 2H), 3.50 (dd, J=7.0, 16.4 Hz, 1H), 3.08–3.41 (m, 4H), 1.38 (s, 3H), 0.83 (s, 3H).

F.

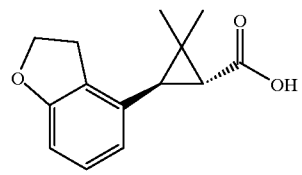

To an oven dried 3L three necked round bottom flask equipped with a mechanical stirrer was placed Part E compound (20.0 g, 92.47 mmol) and anhydrous THF (925 mL). The mixture was stirred to give solution and cooled to −65° C. A solution of 1N LiHMDS in THF (101.7 mL, 101.7 mmol) was added over 15 minutes while keeping the pot temperature below −55° C. The resulting mixture was stirred at −70° C. for 30 minutes and 0° C. for 15 minutes. After cooling back to −70° C., a solution of N-bromosuccinimide (NBS) (16.4 g, 92.2 mmol) in anhydrous THF (230 mL) was added over 5 minutes. After addition was completed the cooling bath was replaced with an ice-water bath and the reaction mixture was stirred to 0° C. for 10–20 minutes at which time HPLC indicated that the bromination was complete. A solution of sodium hydroxide (23.1 g, 577.5 mmol) in DI water (230 mL) was added at 0° C. and the resulting reaction mixture was stirred at room temperature for 15–30 minutes at which time the ring contraction reaction was complete. THF was removed on a rotary evaporator and the rich aqueous was washed with MTBE (2×125 mL). The residual organic solvent was removed on rotary evaporator and the rich aqueous was diluted with DI water (250 mL). The pH of the resulting rich aqueous was then adjusted from ~12.5 to 1.0 using conc. HCl (47 mL).

The resulting slurry was cooled to 0° C. and stirred for 30 minutes. The slurry was filtered, washed with ice-cold DI water (3×50 mL) and suction dried for 18 hours to give 20.6 g (96%) of title compound as white crystalline compound. HPLC 97.7A% at 220 nm. $^1$H NMR ($CDCl_3$) d 7.07 (t, J=7.8 Hz, 1H), 6.71 (d, J=7.9 Hz, 1H), 6.59 (d, J=7.6 Hz), 4.61 (t, J=8.9 Hz, 2H), 2.23–3.32 (m, 1H), 3.07–3.15 (m, 1H), 2.61 (d, J=5.9 Hz, 1H), 2.00 (d, J=5.9 Hz, 1H), 1.47 (s, 3H), 1.00 (s, 3H). $^{13}$C NMR ($CDCl_3$) d 179.3, 160.2, 134.4, 128.4, 127.5, 120.1, 108.3, 71.5, 37.1, 31.6, 30.8, 29.3, 22.4, 20.9.

G.

Resolution of part F Acid

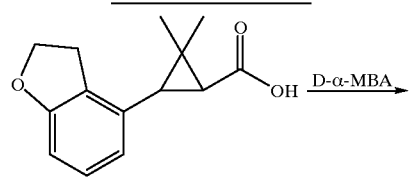

(Part F Racemic Acid)

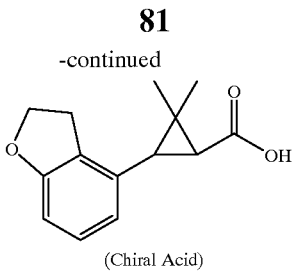

(Chiral Acid)

To a stirring solution of Part F acid (14.0 g, 60.27 mmols) in absolute ethanol (420 mL) at 55° C. was added D-(+)-α-methylbenzylamine (9.2 mL, 72.33 mmols) in one portion. To the solution was added a seed crystal then the mixture was allowed to slowly cool to room temperature with stirring over 2 hrs, then the mixture was stirred an additional 18 hrs at room temperature. The solid was isolated by filtration, washed with hexanes (3×5 pad volumes), air-dried (30 min), dried under vaccum (<2 mm Hg, 16 hr) to afford 7.89 g of amine salt as a white powder (37% yield; 50% theoretical maximum).

To a suspension of amine salt (3.70 g, 10.47 mmol) in EtOAc (50 mL) was added 1N HCl (25 mL) at room temperature. After mixing vigorously, the aqueous solution was removed. The organic solution was washed with sat. aq. NaCl (25 mL), dried (anhyd. MgSO$_4$), filtered, and concentrated in vacuo to afford 2.42 g of chiral acid as a white solid (99% yield).

$^1$H NMR (270 MHz, CDCl$_3$): δ 7.05 (dd, J=7.9 and 7.7 Hz, 1H), 6.68 (d, J=7.9 Hz, 1H), 6.58 (d, J=7.7 Hz, 1H), 4.59 (dd, J=9 and 9 Hz, 2H), 2.9–3.4 (m, 2H), 2.59 (d, J=5.9 Hz, 1H), 1.98 (d, J=5.9 Hz, 1H), 1.45 (s, 3H), and 0.98 (s, 3H).

H.

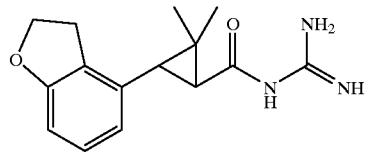

To a stirring solution of Part G chiral carboxylic acid (12 g, 51.7 mmol) in anhydrous DMF (70 mL) was added CDI (10.05 g, 62.04 mmol) in small portions. After 2 h. under argon at RT, a solution of free base guanidine (6.1 g, 103.4 mmol) in DMF (20 mL) was added. Stirring was continued for 18 h at RT. The reaction mixture was diluted with ethyl acetate and washed with water (×5); followed by brine (×1); dried over MgSO$_4$; filtered and solvent was removed in vacuo, affording the crude product as a white foam. The crude product was subjected to reversed phase preparative HPLC (C18 column/water-MeOH-TFA 80:20:0.1 to 10:90:0.1 gradient) to afford a TFA salt of the title compound. This was dissolved in EtOAc, adjusted to pH 7–8 with saturated Na$_2$CO$_3$ aqueous solution, diluted with water, the organic layer was died over MgSO$_4$; filtered and concentrated in vacuo, affording the title compound as a free base. This was taken in THF and treated with 14 mL 4N HCl in dioxane at 0° C. with swirling. The solvent was removed in vacuo and the residue was lyophilized from water to afford the title compound as the HCl salt (white solid, 8.6 g, 54% yield).

MS m/e (M+H)$^+$274$^{30}$ ; $^1$H NMR (270 MHz; CDCl$_3$) d 11.8 (s, 1H); 8.4 (bs, 4H); 7.26 (s, CHCl$_3$); 7.01 (t, J=7.84, 1H); 6.67 (d, J=7.94, 1H); 6.55 (d, J=7.65, 1H); 4.58(t, J=9.2, 2H); 3.25 (m, 1H); 5.05(m, 1H); 2.71(d, J=5.6, 1H); 2.12 (d, J=5.7, 1H); 1.4 (s, 3H); 0.99 (s, 3H). $^{13}$C NMR (270 MHz; CDCl$_3$) 20.52, 22.21, 29.29, 33.22, 34.47, 37.46, 71.43, 77.1, 77.42, 77.75, 108.6, 119.9, 127.4, 128.5, 133.5, 156.4, 160.3, 173.9. Optical rotation [a]$_D$ +7.3° C.=1 CHCl$_3$.

Elemental Analysis: C$_{15}$H$_{19}$N$_3$O.1.0 HCl.0.806 H$_2$O

|  | % C | % H | % N |
| --- | --- | --- | --- |
| Calculated: | 55.55 | 6.72 | 12.96 |
| Found: | 55.55 | 6.43 | 13.03 |

The following compounds were prepared using procedures described above.

| Example No. | Structure | Characterization (MS) |
| --- | --- | --- |
| 149 | 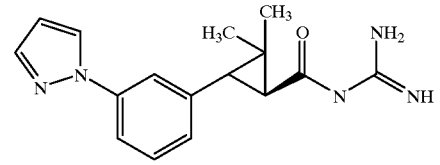 | (M + H)$^+$ 298 |
| 150 | 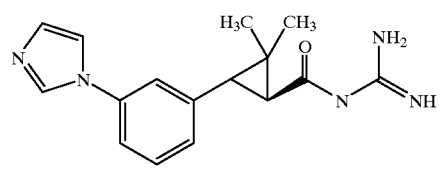 | (M + H)$^+$ 298 |

-continued

| Example No. | Structure | Characterization (MS) |
|---|---|---|
| 151 | 3-chlorophenyl cyclopropane carboxamide guanidine | (M + H)+ 266 |
| 152 | 2-nitrophenyl cyclopropane carboxamide guanidine | (M + H)+ 276 |
| 153 | 3,5-difluorophenyl cyclopropane carboxamide guanidine | (M + H)+ 267 |
| 154 | 4-chlorophenyl cyclopropane carboxamide guanidine | (M + H)+ 266 |
| 155 | 3-bromo-4-fluorophenyl cyclopropane carboxamide guanidine | (M + H)+ 329 |
| 156 | 2,4-difluorophenyl cyclopropane carboxamide guanidine | (M + H)+ 267 |
| 157 | 2,5-difluorophenyl cyclopropane carboxamide guanidine | (M + H)+ 267 |

-continued

| Example No. | Structure | Characterization (MS) |
|---|---|---|
| 158 | 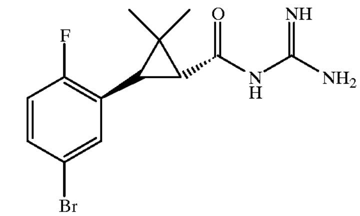 | (M + H)+ 329 |
| 159 | 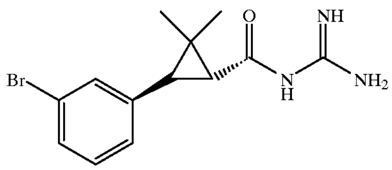 | (M + H)+ 311 |
| 160 | 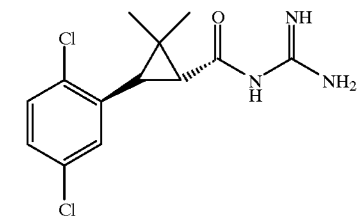 | (M + H)+ 301 |
| 161 | 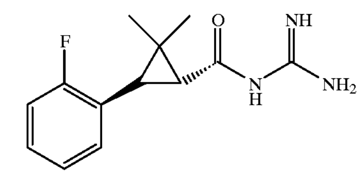 | (M + H)+ 249 |
| 162 | 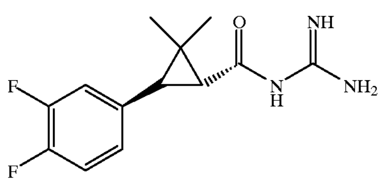 | (M + H)+ 267 |
| 163 | 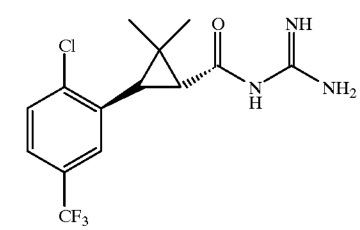 | (M + H)+ 333 |
| 164 | 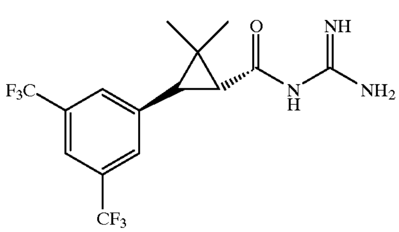 | (M + H)+ 367 |

-continued

| Example No. | Structure | Characterization (MS) |
|---|---|---|
| 165 | 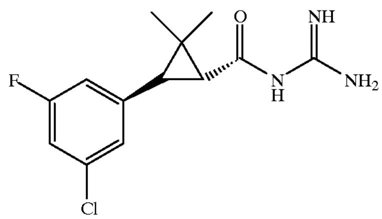 | (M + H)+ 284 |
| 166 | 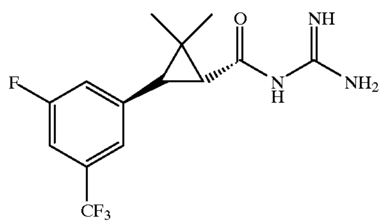 | (M + H)+ 317 |
| 167 | 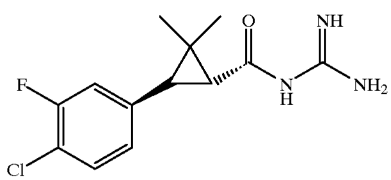 | (M + H)+ 283 |
| 168 | 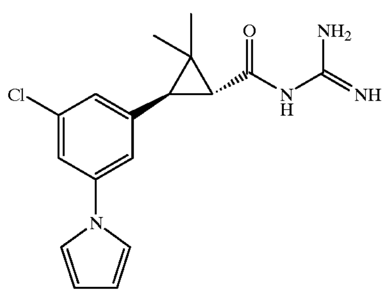 | (M + H)+ 297 |
| 169 | 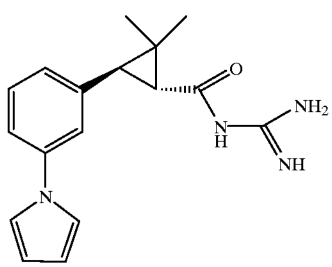 | (M + H)+ 332 |
| 170 | 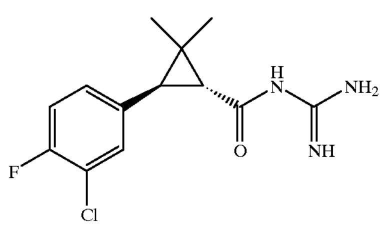 | (M + H)+ 285 |

-continued

| Example No. | Structure | Characterization (MS) |
|---|---|---|
| 171 | 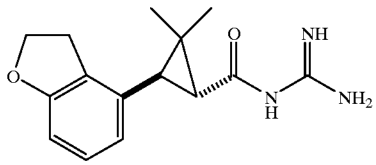 | (M + H)+ 274 |
| 172 | Chiral | (M + H)+ 274 |
| 173 | 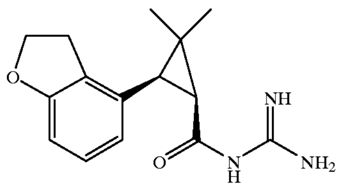 | (M + H)+ 274+ |
| 174 | 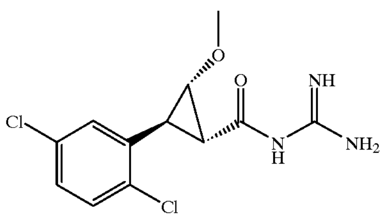 | (M + H)+ 303 |
| 175 | 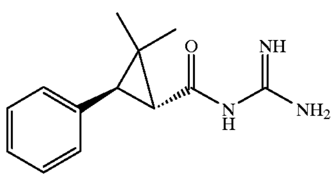 | (M + H)+ 232 |
| 176 | 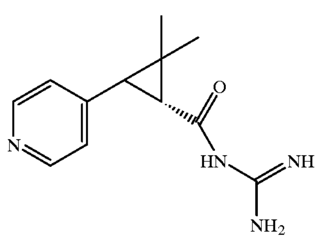 | (M + H)+ 233 |
| 177 | 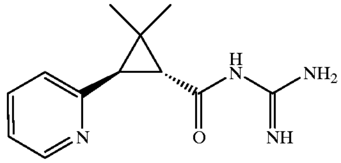 | (M + H)+ 233 |

| Example No. | Structure | Characterization (MS) |
|---|---|---|
| 178 | 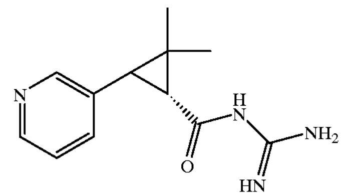 | (M + H)⁺ 233 |
| 179 | 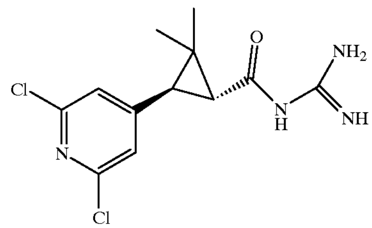 | (M + H)⁺ 302 |
| 180 | 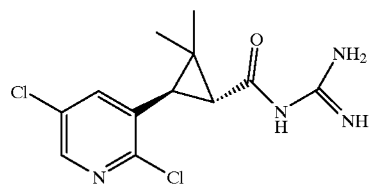 | (M + H)⁺ 302 |
| 181 | 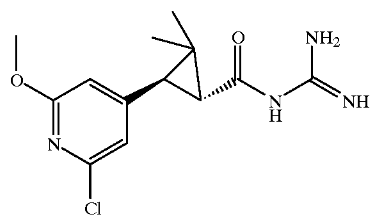 | (M + H)⁺ 298 |
| 182 | 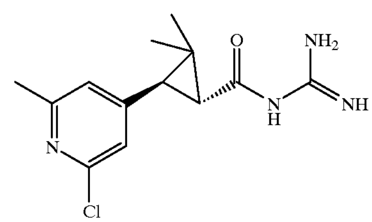 | (M + H)⁺ 281 |
| 183 | 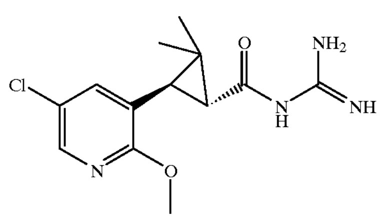 | (M + H)⁺ 297 |
| 184 | 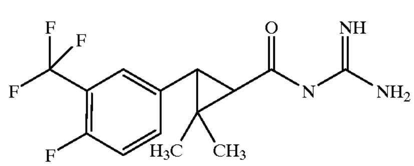 | (M + H)⁺ 318 |

-continued
| Example No. | Structure | Characterization (MS) |
|---|---|---|
| 185 | 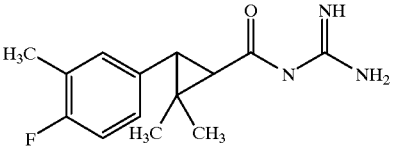 | (M + H)+ 264 |
| 186 | 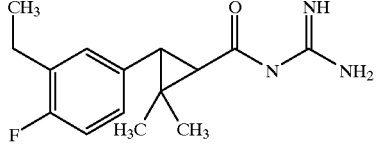 | (M + H)+ 278 |
| 187 | 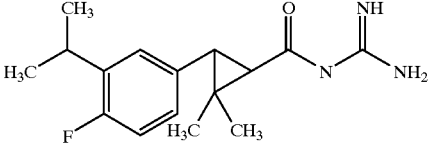 | (M + H)+ 292 |
| 188 | 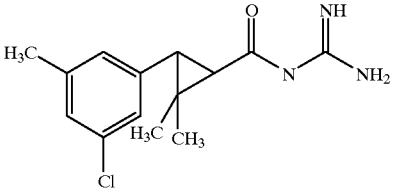 | (M + H)+ 278 |
| 189 | 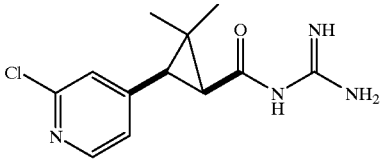 | (M + H)+ 266 |
| 190 | 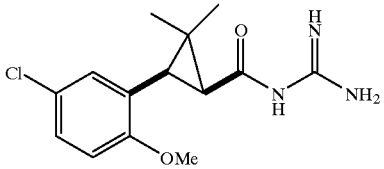 | (M + H)+ 295 |

-continued
| Example No. | Structure | Characterization (MS) |
|---|---|---|
| 191 | 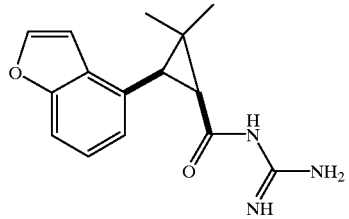 | (M + H)+ 272 |
| 192 | 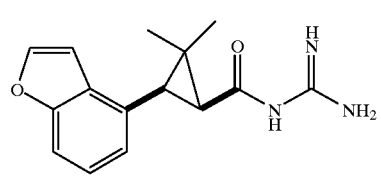 | (M + H)+ 272 |
| 193 | 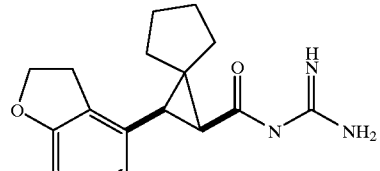 | (M + H)+ 300 |
| 194 | 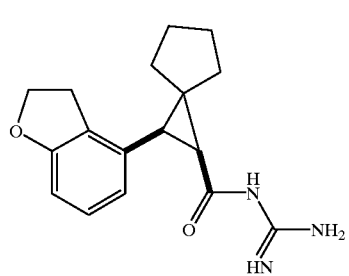 | (M + H)+ 300 |
| 195 | 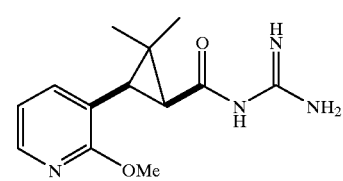 | (M + H)+ 263 |
| 196 | 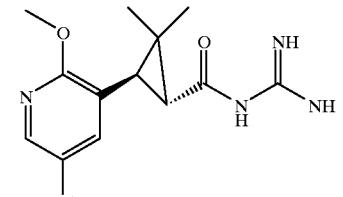 | (M + H)+ 296 |

-continued

| Example No. | Structure | Characterization (MS) |
|---|---|---|
| 197 | 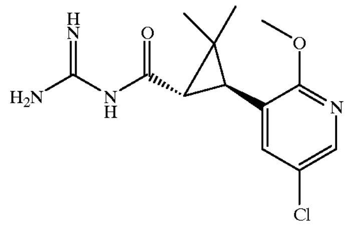 | (M + H)+ 296 |
| 198 | 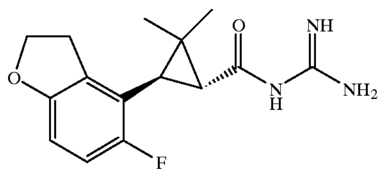 | (M + H)+ 292 |

EXAMPLE 199

A.

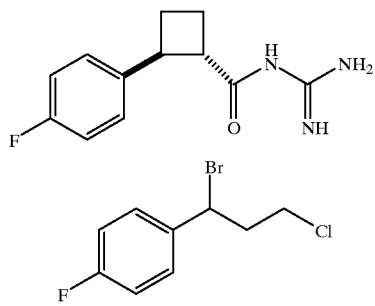

To a solution of 2-chloroethy-4-fluorophenylketone (2 g, 10.7 mmol) in 1:1 solution of THF:ethanol (20 mL) at 0° C. was added sodium borohydride (0.49 g, 12.8 mmol). The resulting solution was stirred for 3 h at 0° C. and was quenched with saturated ammonium chloride (40 mL). The mixture was stirred for 30 min at ambient temperature. The organic layer was separated and aqueous layer was extracted with diethyl ether. The combined organic layers were dried and concentrated to give the corresponding alcohol, which did not further characterized. To the alcohol concentrated HBr (10 mL) was added. The mixture was stirred for 3 h at ambient temperature and poured into ice (ca 30 g) with potassium carbonate (10 g). The mixture was extracted with ethyl acetate. The organic layers were dried and concentrated. The residue was chromatographed on silica gel (ethyl acetate:hexane, 1:9) to give 1.2 g (44%) of title compound.

B.

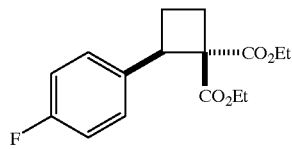

To a solution of Part A compound (1.16 g, 4.6 mmol) in dioxane (20 mL) was added diethyl malonate (0.78 g, 4.9 mmol) and sodium hydride (0.28 g, 11.6 mmol). The mixture was stirred for 13 h at reflux and cooled to ambient temperature. The mixture was diluted with ethyl acetate and washed with brine. The organic layer was dried and concentrated. The residue was chromatographed on silica gel (ethyl acetate:hexane, 5:95) to give 0.72 g (53%) of title compound.

C.

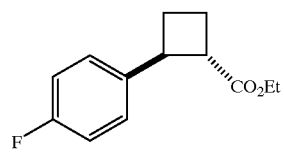

A mixture of Part B compound (0.5 g, 1.7 mmol) and lithium chloride (0.15 g, 3.4 mmol) in 10% aqueous DMSO (10 mL) was stirred for 7 h at reflux and cooled to ambient temperature. The solution was diluted with ethyl acetate and washed with brine. The organic layer was dried and concentrated. The residue was chromatographed on silica gel (ethyl acetate:hexane, 5:95) to give 0.23 g (61%) of title compound.

D.

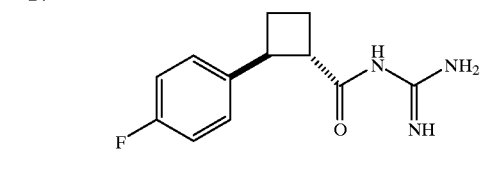

To a solution of Part C compound (0.23 g, 1 mmol) in DMF (5 mL) was added guanidine (0.3 g, 5.1 mmol). The mixture was stirred for 18 h at ambient temperature and diluted with ethyl acetate. The mixture was washed with water and dried and concentrated. The residue was purified using reverse phase preparative HPLC to give 0.1 g of the desired product. ((M+H)+=236).

EXAMPLE 200

A.

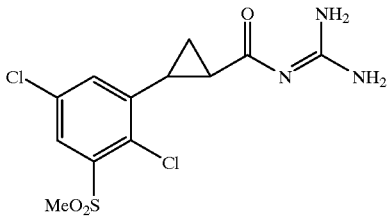

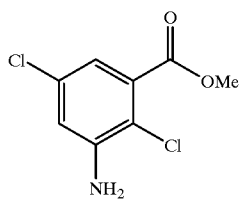

Methyl 3-Amino-2,5-dichlorobenzoate

HCl gas was bubbled through a solution of 2,5-dichloro-3-nitrobenzoic acid (20 g) in 200 mL MeOH and the reaction mixture was 100° C. (bath temperature) to remove approximately 80 mL solvent. The mixture was allowed to come to RT, added 80 mL MeOH and bubbled additional HCl through the reaction mixture. The mixture was heated again to 100° C. to remove the volatiles. The residue was dissolved in 250 mL MeOH, followed by the addition of 10 g RaNi. The mixture was stirred at RT under hydrogen for 16 h, filtered to remove the catalyst and the filtrate was cocentrated in vacuo to afford the title compound as an off-white solid (18.5 g).

B.

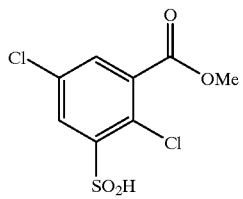

2,5-Dichloro-3-(carboxymethyl)benzenesulfinic acid

A solution of sodium nitrite (1.68 g, 24 mmol) in 5 mL water was added dropwise to a stirred mixture of the Part A compound (4.4 g, 20 mmol), conc. sulfuric acid (15 mL), 89% phosphoric acid (20 mL) and water 10 mL at 0–5° C. over 15 minutes. Stirring was continued at 0–5° C. for 5 h and the reaction mixture was kept at –16° C. for 14 h. To this was added 20 mL precondensed $SO_2$ at –15° C. in one portion and the reslting mixture was immediately poured in to a flask containing Cu powder (200 mg) and $CuSO_4$ heptahydrate (11.12 g, 40 mmol) with stirring. The resulting foamy mixture was stirred at RT for 4 h, diluted with water and extracted with ethyl acetate. The ethyl acetate layer was extracted with 2 N NaOH, the NaOH layer was acidified with 20% sulfuric acid and extracted with ethyl acetate. The ethyl acetate layer was dried over magnesium sulfate and concentrated to give the title compound as a yellow solid (2.9 g).

C.

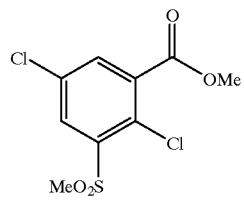

Methyl 2,5-Dichloro-3-(carboxymethyl)-benzenesulfonate

To a solution of Part B compound (1 g) in 5 mL DMF was added potassium carbonate (770 mg) and MeI (795 mg) and the resulting mixture was stirred at RT for 24 h. The mixture was diluted with water, extracted with ethyl acetate, the organic layer was washed with brine, dried over magnesium sulfate and concentrated in vacuo to afford the title compound as a yellow gummy oil (1 g).

D.

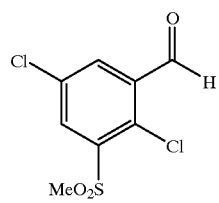

Methyl 2,5-Dichloro-3-formylbenzenesulfonate

To a solution of the Part C ester (1 g, 3.53 mmol) in 25 mL toluene was added a solution of duisobutylaluminum hydride (DIBAL) in toluene (1.5 M, 5.2 mL, 7.8 mmol) at –78° C. and the mixture was stirred at that temperature for minutes. The mixture was allowed to come to –25° C., stirred for 15 min., cooled to –78° C. and quenched by adding 5 mL MeOH. The reaction mixture was diluted with EtOAc, washed sequentially with dilute HCl, saturated $NaHCO_3$ and brine. The organic layer was dried over magnesium sulfate and concentrated. This compound was oxidized as reported in Example 2, Step C to give the title compound as a thick pale oil (0.9 g).

E.

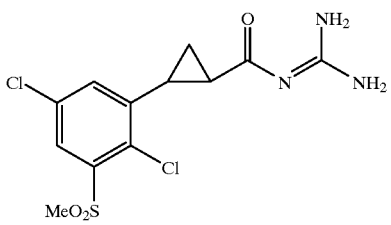

$(M + H)^+ = 350$

The title compound was prepared employing the Part D intermediate and the procedures set out hereinbefore.

EXAMPLE 201

A.

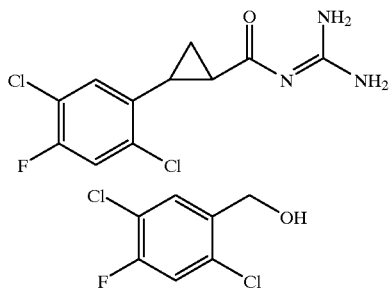

2,5-Dichloro-4-fluorobenzyl alcohol

A solution of 2,5-dichloro-4-fluorobenzoic acid (4.1 g, 19.6 mmol; prepared as described in the literature: Feit, P. W. et al, J. Med. Chem. 1972, Vol. 15, 79–83) in 100 mL THF was treated with 24.5 mL borane methylsulfide complex in THF (2M, 24.5 mL, 49 mmol) at 0–5° C. The mixture was allowed to come to RT, stirred for 14 h at RT and quenched by adding saturated NaHCO$_3$ and 10 mL MeOH. The mixture was extracted with ethyl acetate, the organic layer was washed sequentially with 10% HCl and saturated NaHCO$_3$ solutions, dried over magnesium sulfate and concentrated to give 3.65 g of the title compound as a white solid.

B.

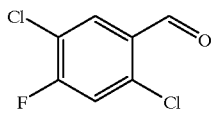

2,5-Dichloro-4-fluorobenzaldehyde

To a solution of oxalyl chloride (1.72 mL, 19.74 mmol) in 20 mL methylene chloride at −78° C. was added a solution DMSO (2.8 mL, 39.5 mL) in 3 mL methylene chloride. The mixture was stirred for 5 minutes at −78° C. followed by the addition of a solution of Part A 2,5-dichloro-4-fluorobenzyl alcohol (3.5 g, 17.95 mmol) from above in 15 mL methylene chloride. The mixture was stirred at −40° C. for 15 min., cooled to −78° C. followed by the addition of triethylamine (8.26 mL, 59.2 mmol). The mixture was allowed to come to RT, washed sequentially with 10% HCl, saturated sodium bicarbonate solution and water. The organic layer was dried over magnesium sulfate and concentrated to afford the title compound 3.39 g as a white solid.

C.

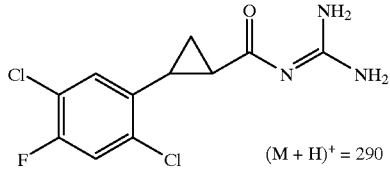

(M + H)$^+$ = 290

The title compound was prepared employing the Part B intermediate and the procedures set out hereinbefore.

EXAMPLE 202

A.

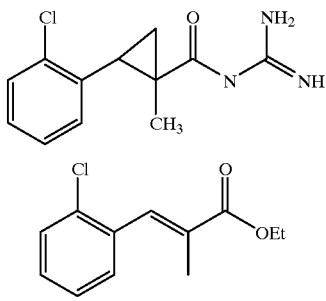

trans-Ethyl-(2-chloro)-α-methylcinnamate

A solution of 2-chlorobenzaldehyde (1.29 g, 9.2 mmol) and (carbethoxyethylidene)-triphenylphosphorane (5.0 g, 13.8 mmol) in dichloromethane (40 mL) was heated while stirring at 40° C. for 18 hours. After the reaction solution cooled down to RT, the solution was concentrated in vacuo to remove solvent. The resulting off-white solid was subjected to flash chromatography (silica gel, 7:3 hexane:ethyl acetate) to afford the title compound (1.88 g, 8.34 mmol, 91% yield) as a clear heavy oil.

B.

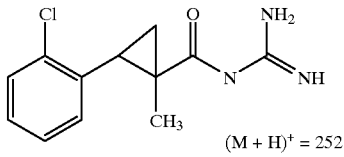

(M + H)$^+$ = 252

The title compound was prepared employing the Part A intermediate and the procedures set out hereinbefore ((M+H)$^+$=252).

EXAMPLE 203

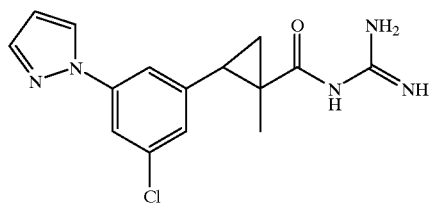

EXAMPLE 204

A.

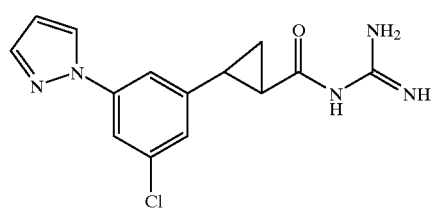

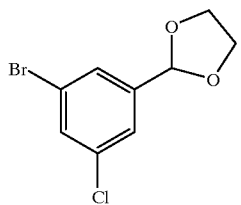

2-(3-Bromo-5-chlorophenyl)-1,3-dioxalane

To a solution of 3-bromo-5-chlorobenzaldehyde (prepared using the methodology described in patent WO 9708145, 970306, by Ruminski, Peter et al; 1.91 g, 8.7 mmol) in toluene (150 mL) was added ethylene glycol (2.91 mL, 52 mmol) and p-toluene sulfonic acid monohydrate (50 mg, 0.26 mmol). The reaction flask was attached to a Dean-Stark trap to remove water. After refluxing for 18 hours, the reaction mixture was washed with saturated NaHCO3 solution (2x). The organic layer was dried over MgSO4, filtered, and concentrated in vacuo to remove solvent and the resulting oil was subjected to flash chromatography (silica gel, 9:1 hexane:ethyl acetate) to afford the title compound (1.95 g, 7.4 mmol, 85% yield) as a light yellow oil.

B.

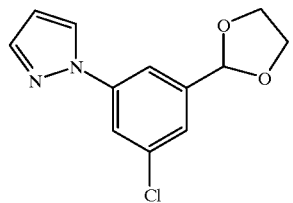

2-(3-Chloro-[5-(1H-pyrazol-1-yl)]phenyl)-1,3-dioxalane

A solution of pyrazole (258 mg, 3.79 mmol) in DMF (5 mL) was added dropwise at RT to a solution of NaH (100 mg, 4.17 mmol) in DMF (10 mL) while stirring. After stirring for an additional 5 min, a solution of Part A 2-(3-bromo-5-chlorophenyl)-1,3-dioxalane (1 g, 3.79 mmol) in DMF (10 mL) and CuI (145 mg, 0.76 mmol) were added to the reaction solution. The reaction mixture was heated to 150° C. for 7 h. Cooled to RT, the reaction mixture was diluted with dichloromethane and washed with water. The layers were separated and the water layer was backwashed with fresh dichloromethane (2x). All the organic layers were combined, dried over anhydrous MgSO$_{41}$ filtered and the solvent was removed in vacuo affording an oil. Flash chromatography (silica gel, 8:2 hexane:ethyl acetate) was used to isolate the title compound as an off-white solid (618 mg, 2.47 mmol, 65% yield).

C.

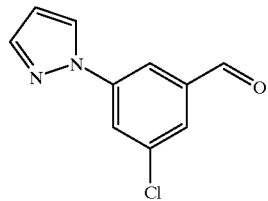

3-Chloro-5-(1H-pyrazol-1-yl)benzaldehyde

Part B 2-(3-chloro-[5-(1H-pyrazol-1-yl)]phenyl)-1,2-dioxalane (669 mg, 2.67 mmol) was stirred at room temperature for 2 h. in 1N HCl (30 mL) and dioxane (4 mL). The reaction mixture was neutralized with saturated NaHCO$_3$ solution and extracted with ethyl acetate (3x). All the organic layers were combined and dried over anhydrous MgSO$_4$, filtered and the solvent was removed in vacuo affording the title compound as an off-white solid (552 mg, 2.67 mmol, 100% yield).

D.

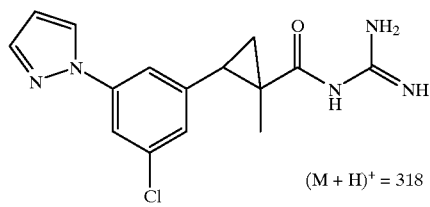

$(M + H)^+ = 318$

E.

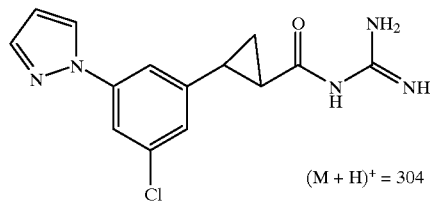

$(M + H)^+ = 304$

The title D and E compounds were prepared employing the Part C intermediate and the procedures set out hereinbefore.

EXAMPLE 205

A.

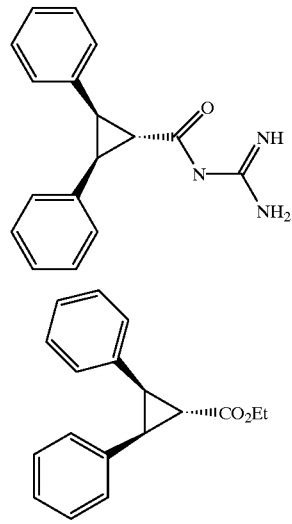

Ethyl 2,3-cis-diphenylcyclopropane carboxylate

A solution of tris(4-bromophenyl)aminium hexachloroantimonate (245 mg) in dichloromethane (10 mL) was cooled in an ice bath and purged with nitrogen for 1 h. To this was added a solution of cis-stilbene (180 mg) and ethyl diazoacetate (1.14 g) in dichloromethane (10 mL). Recation mixture was stirred overnight and allowed to warm to ambient temperature. Reaction was quenched with saturated potassium carbonate solution in methanol (5 mL), diluted with water and extracted with ethyl acetate. Organic layer was separated, dried over magnesium sulfate and concentrated to give crude title compound (0.1 g) which was used without purification.

B.

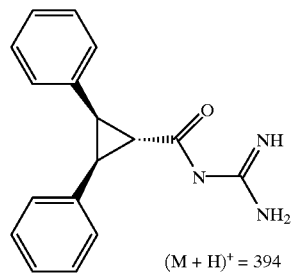

(M + H)⁺ = 394

The title compound was prepared emlopying the Part A intermediate and the procedures set out hereinbefore.

EXAMPLE 206

A.

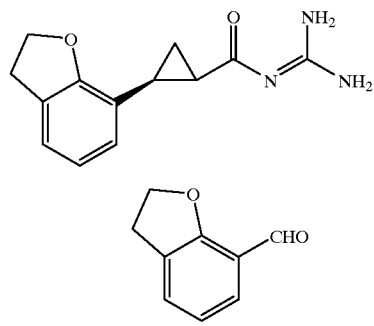

2,3-Dihydrobenzofuran-7-carboxaldehyde

A solution of 2,3-dihydrobenzofuran-7-carboxylic acid (1.0 g, 6.09 mmol, 1.0 equiv.), dimethylmethoxyamine hydrochloride (654 mg, 6.7 mmol, 1.1 equiv.), diisopropylethylamine (DIEA) (2.35 ml, 13.4 mmol, 2.2 equiv.), benzotriazole-1-yl-oxy-tris-pyrrolidino-phosphonium hexafluorophosphate (PyBOP) (3.48 g, 6.7 mmol, 1.1 equiv.) and 4-dimethylaminopyridine (DMAP) (74 mg, 0.67 mmol, 0.1 equiv.) in anhydrous THF (20 ml) was stirred for 18 hr under argon. The reaction mixture was then diluted with EtOAc (100 ml) and washed with aqueous sat. NaHCO3 (2×150 ml) and aqueous 1N HCl (2×150 ml), the oragnic layer was dried over MgSO4, filtered and solvent removed. yield: 1.06 mg, 84%. LS-MS calcd 207, found 208.

To a solution of the amide (950 mg, 4.59 mmol, 1.0 equiv.) in anhydrous THF (20 ml) was cooled to −5C under argon, was slowly added 1.0 M LAH in THF (9.1 ml, 9.14 mmol, 1.5 equiv.), the reaction mixture was stirred for 1 hr at −5C. A solution of aqueous 1 N HCl (150 ml) was slowly added to the reaction mixture, and extracted with EtOAc (50 ml). The organic layer was washed with aqueous 1 N HCl (150 ml), the organic layer was collected and dried over MgSO4, filter and solvent removed under reduced pressure to yield the aldhyde. Yield: 620 mg, 91%. LR-MS calcd 148, found 149.

B.

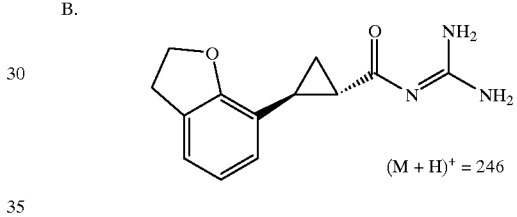

(M + H)⁺ = 246

The Part A intermediate was used in preparing the title compound employing the procedures set out hereinbefore.

EXAMPLES 207 to 257

The following compounds were prepared from the corresponding aldehydes, acids or esters using the procedures described above.

| Example No. | Structure | Characterization (MS) |
|---|---|---|
| 207 | 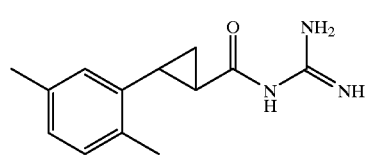 | (M + H)⁺ 260 |
| 208 | 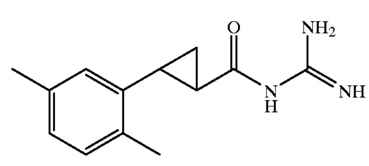 | (M + H)⁺ 232 |

-continued

| Example No. | Structure | Characterization (MS) |
|---|---|---|
| 209 | 2,5-dimethylphenyl-cyclopropyl-C(O)NH-C(=NH)NH₂ (chiral) | (M + H)⁺ 232 |
| 210 | 2,5-dimethylphenyl-cyclopropyl-C(O)NH-C(=NH)NH₂ (chiral) | (M + H)⁺ 232 |
| 211 | 3,5-dichlorophenyl-cyclopropyl-C(O)NH-C(=NH)NH₂ | (M + H)⁺ 272 |
| 212 | 2,3,5-trichlorophenyl-cyclopropyl-C(O)NH-C(=NH)NH₂ | (M + H)⁺ 306 |
| 213 | 2,3-dichlorophenyl-cyclopropyl-C(O)NH-C(=NH)NH₂ | (M + H)⁺ 272 |
| 214 | 2-methyl-5-chlorophenyl-cyclopropyl-C(O)NH-C(=NH)NH₂ | (M + H)⁺ 252 |
| 215 | 2-chloro-5-methylphenyl-cyclopropyl-C(O)NH-C(=NH)NH₂ | (M + H)⁺ 252 |
| 216 | 2,5-dichlorophenyl-cyclopropyl-C(O)NH-C(=NH)NH₂ | (M + H)⁺ 272 |

-continued
| Example No. | Structure | Characterization (MS) |
|---|---|---|
| 217 | 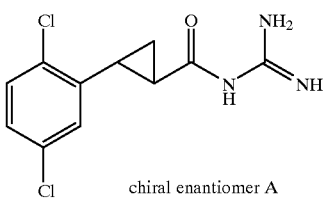 chiral enantiomer A | (M + H)⁺ 272 |
| 218 | 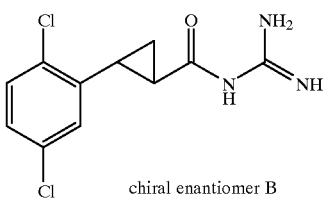 chiral enantiomer B | (M + H)⁺ 272 |
| 219 | 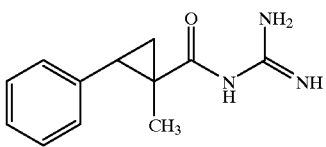 | (M + H)⁺ 218 |
| 220 | 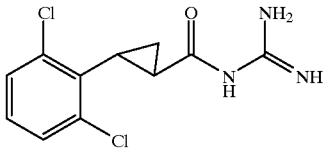 | (M + H)⁺ 272 |
| 221 | 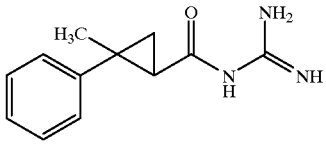 | (M + H)⁺ 218 |
| 222 | 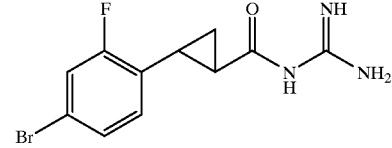 | (M + H)⁺ 301 |
| 223 | 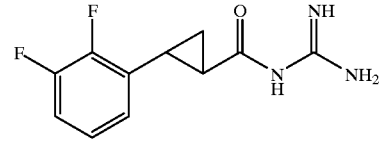 | (M + H)⁺ 240 |
| 224 | 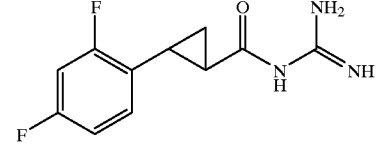 | (M + H)⁺ 240 |

| Example No. | Structure | Characterization (MS) |
|---|---|---|
| 225 | 4-tert-butylphenyl cyclopropyl carbonyl guanidine | (M + H)+ 260 |
| 226 | 5-bromo-2-ethoxyphenyl cyclopropyl carbonyl guanidine | (M + H)+ 328 |
| 227 | 3-benzyloxy-4-methoxyphenyl cyclopropyl carbonyl guanidine | (M + H)+ 340 |
| 228 | 4-(2-chlorophenoxy)-3-nitrophenyl cyclopropyl carbonyl guanidine | (M + H)+ 375 |
| 229 | 4-(3-chlorophenoxy)-3-nitrophenyl cyclopropyl carbonyl guanidine | (M + H)+ 375 |

-continued

| Example No. | Structure | Characterization (MS) |
|---|---|---|
| 230 | 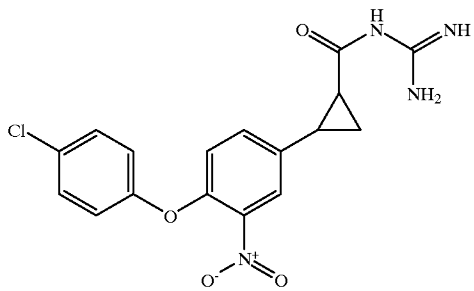 | (M + H)+ 375 |
| 231 | 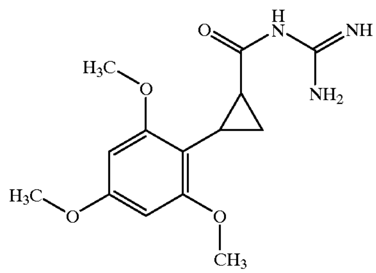 | (M + H)+ 294 |
| 232 | 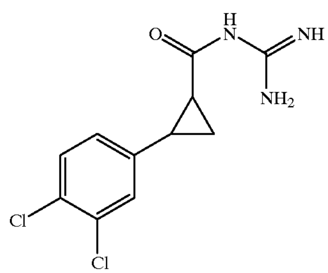 | (M + H)+ 272 |
| 233 | 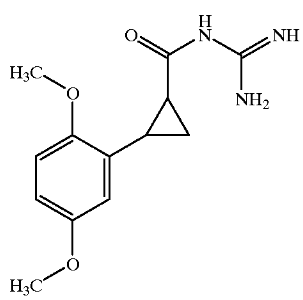 | (M + H)+ 264 |
| 234 | 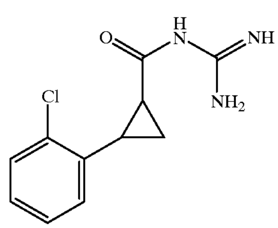 | (M + H)+ 238 |
| 235 | 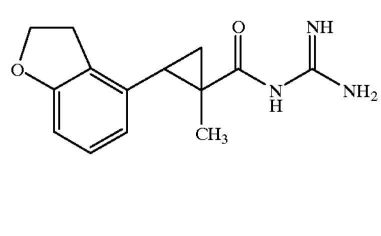 | (M + H)+ 260 |

-continued

| Example No. | Structure | Characterization (MS) |
|---|---|---|
| 236 | 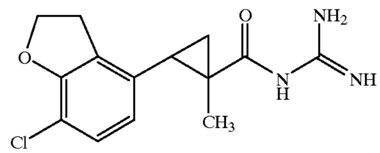 | (M + H)+ 252 |
| 237 | 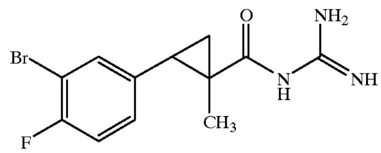 | (M + H)+ 314 |
| 238 | 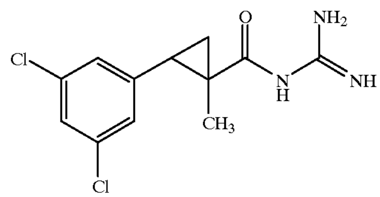 | (M + H)+ 286 |
| 239 | 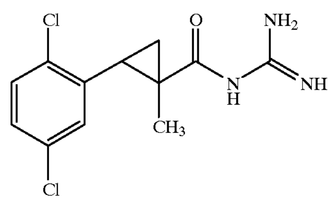 | (M + H)+ 286 |
| 240 | 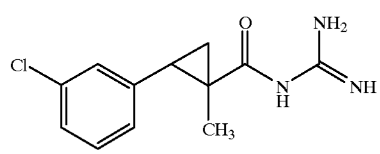 | (M + H)+ 252 |
| 241 | 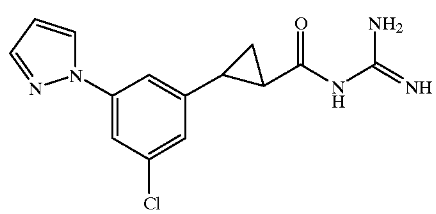 | (M + H)+ 304 |
| 242 | 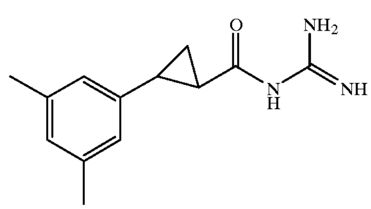 | (M + H)+ 232 |
| 243 | 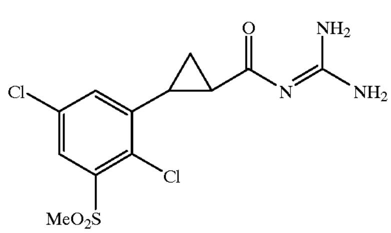 | (M + H)+ 350 |

-continued
| Example No. | Structure | Characterization (MS) |
|---|---|---|
| 244 | 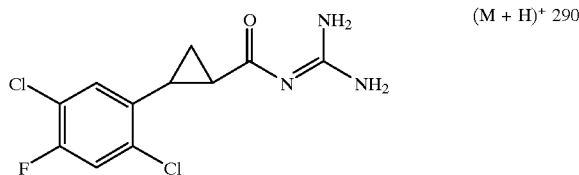 | (M + H)+ 290 |
| 245 | 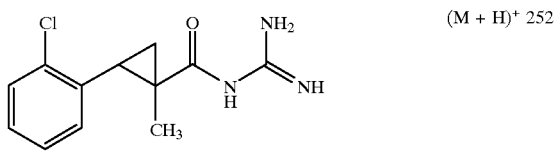 | (M + H)+ 252 |
| 246 | 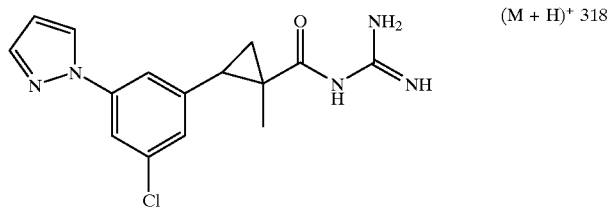 | (M + H)+ 318 |
| 247 | 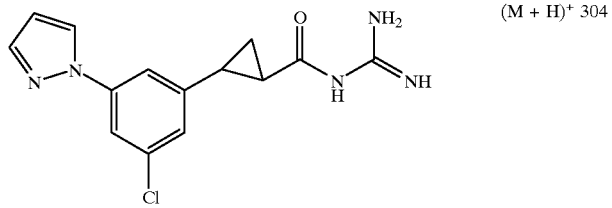 | (M + H)+ 304 |
| 248 | 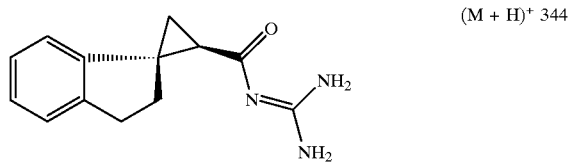 | (M + H)+ 344 |
| 249 | 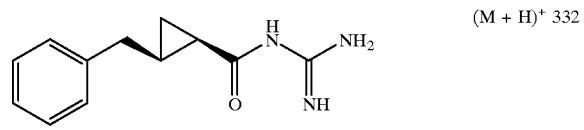 | (M + H)+ 332 |

| Example No. | Structure | Characterization (MS) |
|---|---|---|
| 250 | 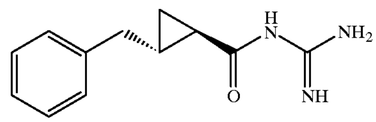 | (M + H)+ 332 |
| 251 | 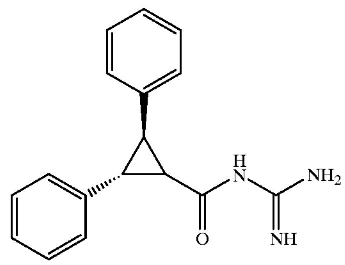 | (M + H)+ 394 |
| 252 | 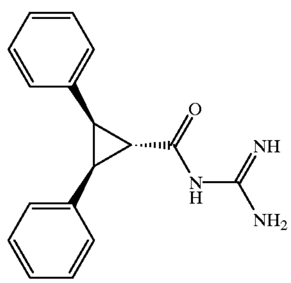 | (M + H)+ 394 |
| 253 | 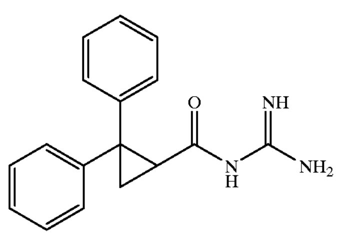 | (M + H)+ 394 |
| 254 | 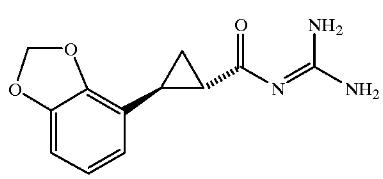 | (M + H)+ 248 |
| 255 | 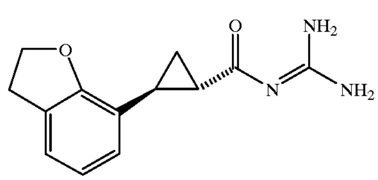 | (M + H)+ 246 |
| 256 | 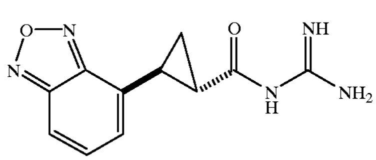 | (M + H)+ 246 |

| Example No. | Structure | Characterization (MS) |
|---|---|---|
| 257 | 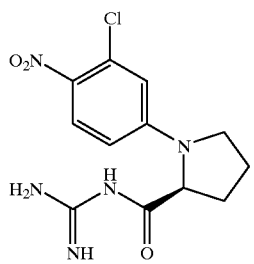 | (M + H)+ 266 |

EXAMPLE 258
(S)-N-(Aminoiminomethyl)-1-(3-chloro-4-nitrophenyl)-2-pyrrolidinecarboxamide

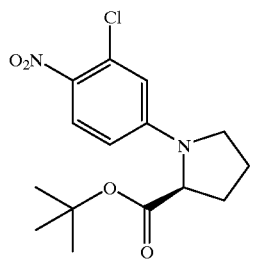

A. (S)-1-(3-Chloro-4-nitrophenyl)-2-pyrrolidinecarboxylic acid 1,1-dimethylethyl ester

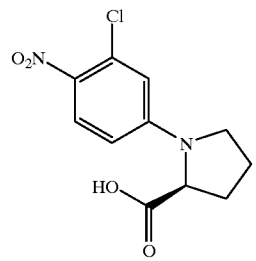

To a solution of L-proline tert-butyl ester

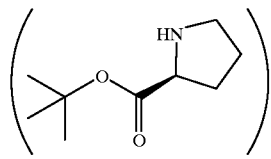

(1.06 g, 7.5 mmol) in dry DMSO (10 ml) were added 3-chloro-4-nitrofluorobenzene (1.48 g, 8.4 mmol) and diisopropylethylamine (2.60 mL, 15 mmol). The resulting solution was heated at 110° C. in a sealed tube for 48 hours. The reaction mixture was cooled to room temperature and partitioned between brine and ethyl acetate. The aqueous layer was extracted with ethyl acetate. The combined organic extracts were washed with water, dried over sodium sulfate, and concentrated in vacuo. Purification of the crude residue on silica gel (7:3/EtOAc-hexanes) provided 1.98 g (90%) of a pale yellow solid.

$^1$H NMR (CD$_3$OD): d 8.13 (1H, d, J=2.7 Hz), 8.02 (1H, dd, J=9.3 Hz, 2.7 Hz), 6.92 (1H, d, J=9.3 Hz), 5.01 (1H, dd, J=9.2 Hz, 3.9 Hz), 3.35 (1H, m), 3.30 (1H, m), 2.31 (1H, m), 2.07 (1H, m), 2.02 (2H, m), 1.38 (9H, s).

B. (S)-1-(3-Chloro-4-nitrophenyl)-2-pyrrolidinecarboxylic acid

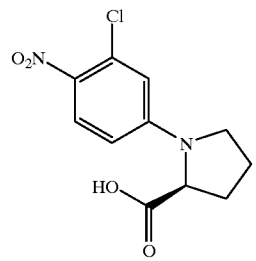

The Part A compound (0.44 g, 1.5 mmol) was dissolved in 1:1 CH$_2$Cl$_2$-trifluoroacetic acid (5 mL). The resulting solution was stirred at room temperature for 12 hours. The reaction mixture was concentrated in vacuo and azeotroped with toluene to afford 350 mg of the title compound as a brown solid.

$^1$H NMR (CD$_3$OD): d 8.26 (1H, d, J=2.7 Hz), 8.17 (1H, dd, J=9.3 Hz, 2.7 Hz), 7.19 (1H, d, J=9.3 Hz), 5.20 (1H, dd, J=9.2 Hz, 3.9 Hz), 3.94 (1H, m), 3.77 (1H, m), 2.64 (1H, m), 2.27 (1H, m), 2.19 (3H, m).

C. (S)-N-(Aminoiminomethyl)-1-(3-chloro-4-nitrophenyl)-2-pyrrolidinecarboxamide

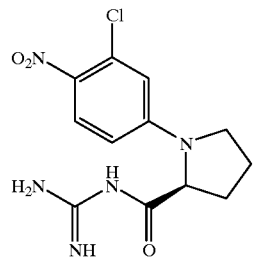

To a solution of Part B compound (0.36 mg, 1.5 mmol) in dry DMF (5 mL) at room temperature was added 1,1'-carbonyldiimidazole (0.29 g, 1.8 mmol). The resulting solution was stirred at room temperature for 2 hours, then cooled to 0° C. To the reaction mixture was added solid guanidine (0.44 g, 7.5 mmol). The resulting solution was warmed to room temperature and stirred for 12 hours. The reaction mixture was partitioned between water and ethyl acetate. The aqueous layer was extracted with ethyl acetate. The combined organics were washed with brine, dried over sodium sulfate, and concentrated in vacuo. Purification of the crude residue by preparative HPLC (C18 column/ 10:90:0.1 to 90:10:1 MeOH-water-TFA gradient) provided the desired product (110 mg, 27%) as white solid.

$^1$H NMR (CD$_3$OD): d 8.28 (1H, d, J=2.7 Hz), 8.19 (1H, dd, J=9.3 Hz, 2.7 Hz), 7.22 (1H, d, J=9.3 Hz), 5.31 (1H, dd, J=9.2 Hz, 3.9 Hz), 3.97 (1H, m), 3.79 (1H, m), 2.65 (1H, m), 2.30 (1H, m), 2.21 (2H, m). LRMS (M+H)$^+$=312.

EXAMPLES 259 TO 282

The following compounds (Examples 259 to 282) were prepared employing a procedure similar to that as set out in Example 258.

| Example No. | Structure | Characterization (MS) |
|---|---|---|
| 259 | 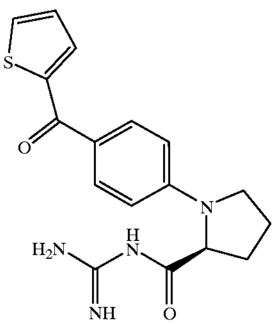 | (M + H)+ 343 |
| 260 | 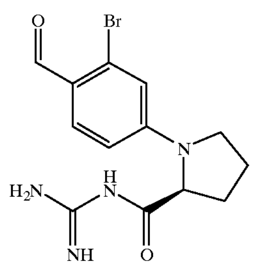 | (M + H)+ 339 |
| 261 | 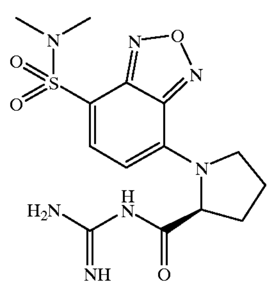 | (M + H)+ 382 |
| 262 | 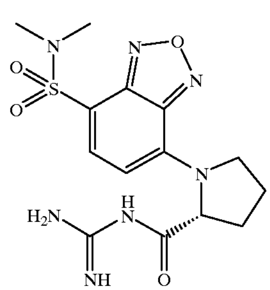 | (M + H)+ 382 |

-continued

| Example No. | Structure | Characterization (MS) |
|---|---|---|
| 263 | 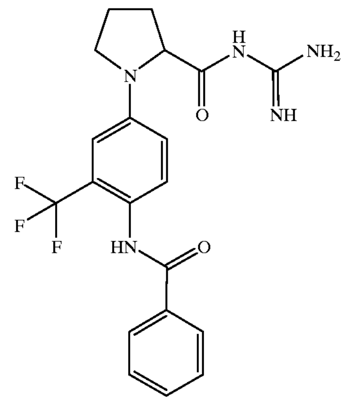 | (M + H)+ 420 |
| 264 | 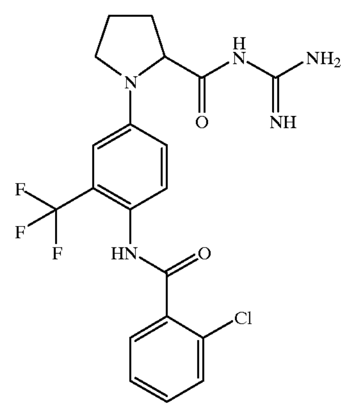 | (M + H)+ 454 |
| 265 | 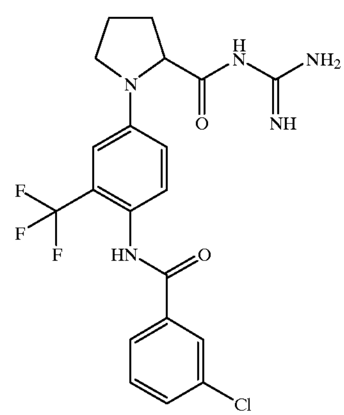 | (M + H)+ 454 |

-continued

| Example No. | Structure | Characterization (MS) |
|---|---|---|
| 266 | 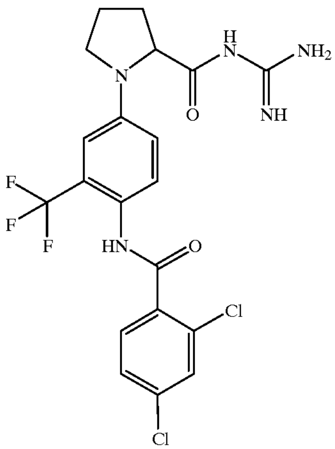 | (M + H)+ 488 |
| 267 | 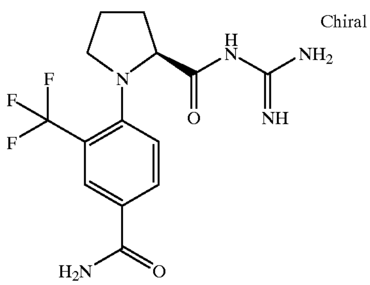 | (M + H)+ 343 Chiral |
| 268 | 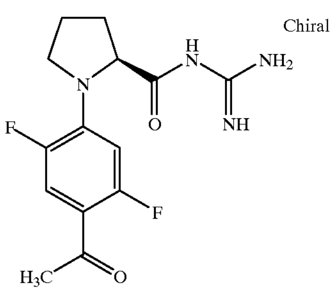 | (M + H)+ 311 Chiral |
| 269 | 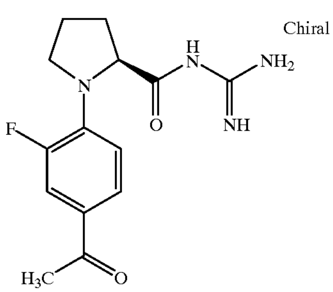 | (M + H)+ 311 Chiral |

-continued

| Example No. | Structure | Characterization (MS) |
|---|---|---|
| 270 | 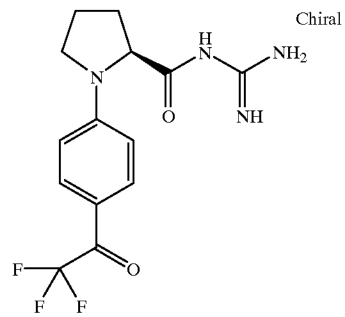 | (M + H)+ 328 Chiral |
| 271 | 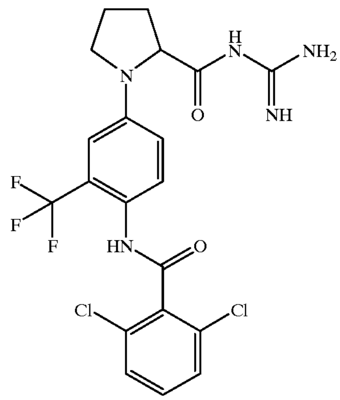 | (M + H)+ 488 |
| 272 | 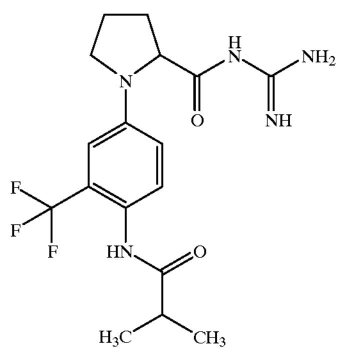 | (M + H)+ 386 |
| 273 | 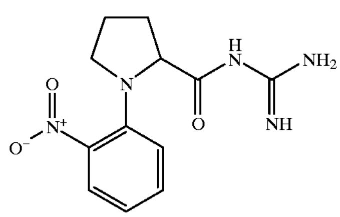 | (M + H)+ 278 |

-continued
| Example No. | Structure | Characterization (MS) |
|---|---|---|
| 274 | 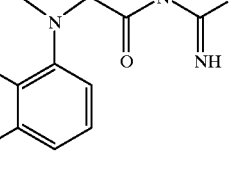 | (M + H)+ 326 |
| 275 | 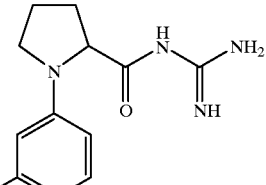 | (M + H)+ 311 |
| 276 | 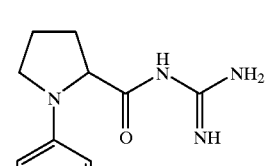 | (M + H)+ 392 |
| 277 | 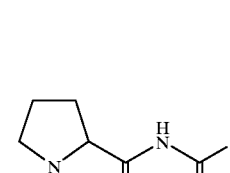 | (M + H)+ 454 |
-continued
| Example No. | Structure | | Characterization (MS) |
|---|---|---|---|
| 278 | 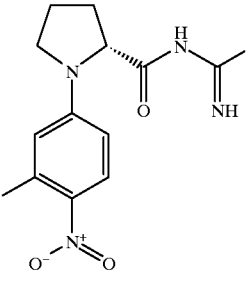 | Chiral | (M + H)+ 312 |
| 279 | 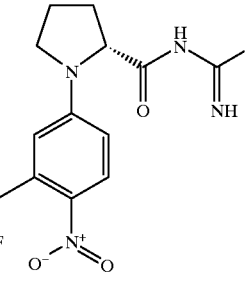 | Chiral | (M + H)+ 346 |
| 280 | 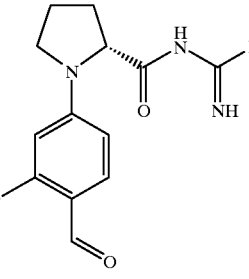 | Chiral | (M + H)+ 339 |
| 281 | 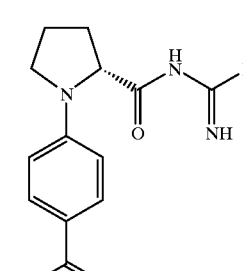 | Chiral | (M + H)+ 343 |

-continued

| Example No. | Structure | Characterization (MS) |
|---|---|---|
| 282 | 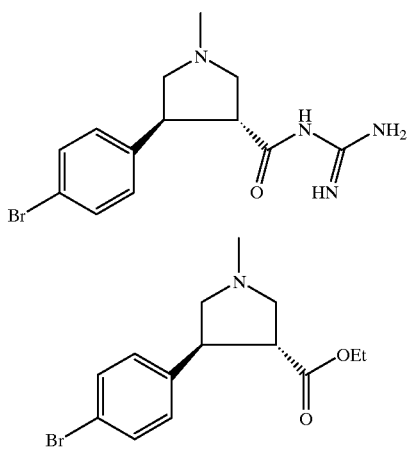 | (M + H)+ 346 |

EXAMPLE 283

A.

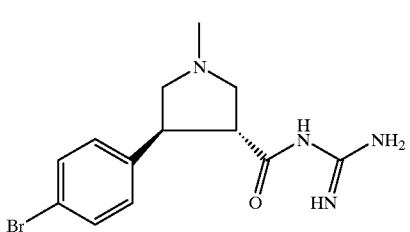

A mixture of ethyl 4-bromocinnamate (0.5 g, 2 mmol), sarcosine (0.19 g 2.2 mmol), and paraformaldehyde (0.19 g, 6.4 mmol) in benzene (50 mL) was stirred for 10 hr at reflux with continuous removal of water. The mixture was cooled to ambient temperature and concentrated. The residue was chromatographed on silica gel (ethyl acetate) to give the desired product (0.21 g).

B.

To a solution of Part A compound (0.15 g, 0.5 mmol) in DMF (10 mL) was added guanidine (0.14 g, 2.4 mmol) at ambient temperature. The resulting solution was stirred at ambient temperature for 18 hr and diluted with ethyl acetate and washed with brine. The organic layer was dried (MgSO$_4$) and concentrated. The residue was purified by reverse phase preparative HPLC to give title compound as a white powder. (M+H)+=326.

EXAMPLES 284 TO 315

The following compounds were prepared employing a procedure analogous to that as set out in Example 283.

| Example No. | Structure | Characterization (MS) |
|---|---|---|
| 284 | 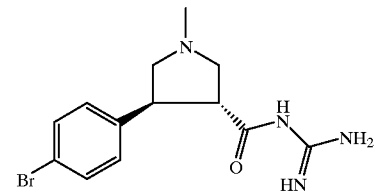 | (M + H)+ 326 |
| 285 | 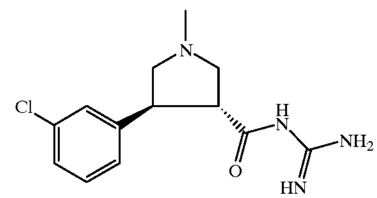 | (M + H)+ 281 |
| 286 | 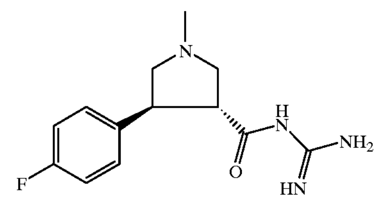 | (M + H)+ 265 |
| 287 | 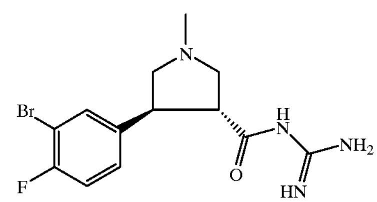 | (M + H)+ 344 |
| 288 | 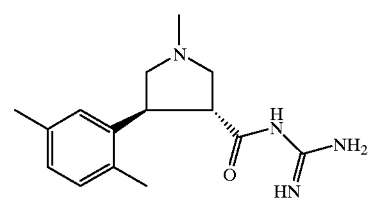 | (M + H)+ 275 |
| 289 | 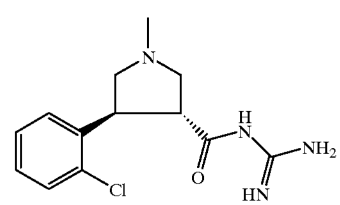 | (M + H)+ 281 |
| 290 | 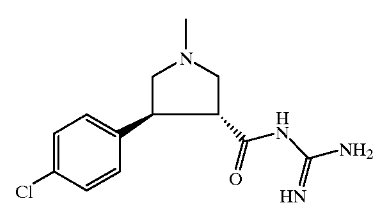 | (M + H)+ 281 |

-continued

| Example No. | Structure | Characterization (MS) |
|---|---|---|
| 291 | 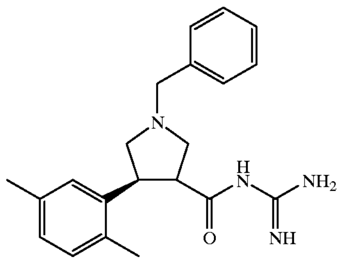 | (M + H)+ 351 |
| 292 | 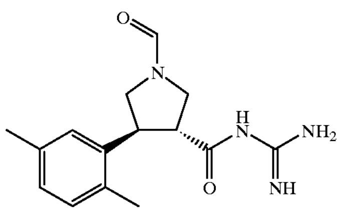 | (M + H)+ 289 |
| 293 | 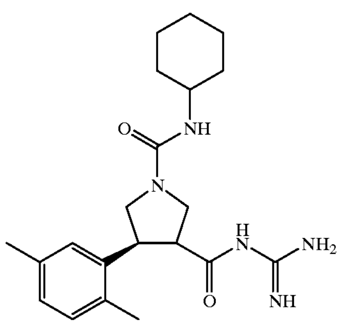 | (M + H)+ 386 |
| 294 | 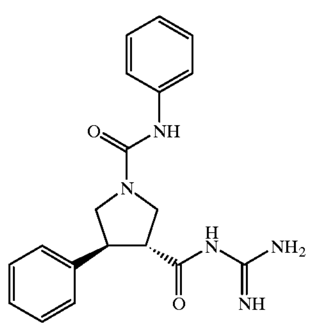 | (M + H)+ 352 |
| 295 | 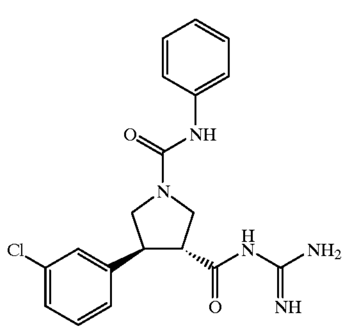 | (M + H)+ 387 |

-continued

| Example No. | Structure | Characterization (MS) |
|---|---|---|
| 296 | 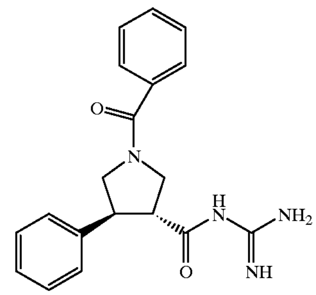 | (M + H)+ 337 |
| 297 | 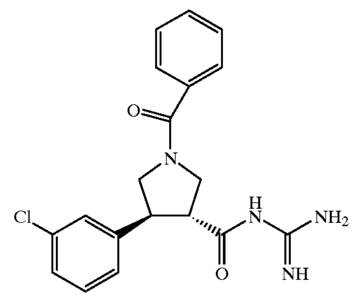 | (M + H)+ 372 |
| 298 | 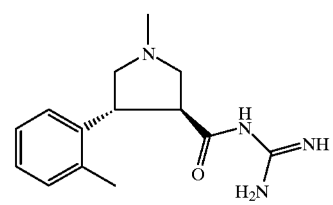 | (M + H)+ 261 |
| 299 | 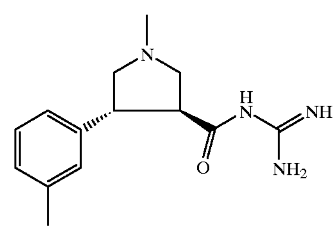 | (M + H)+ 261 |
| 300 | 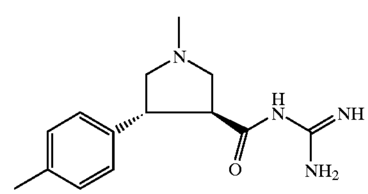 | (M + H)+ 261 |
| 301 | 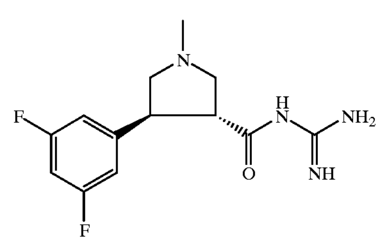 | (M + H)+ 283 |

-continued

| Example No. | Structure | Characterization (MS) |
|---|---|---|
| 302 | 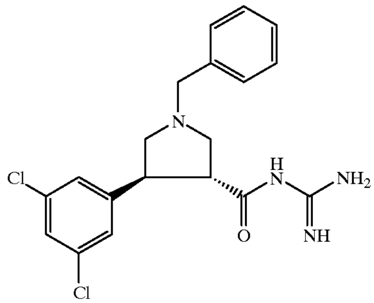 | (M + H)⁺ 392 |
| 303 | 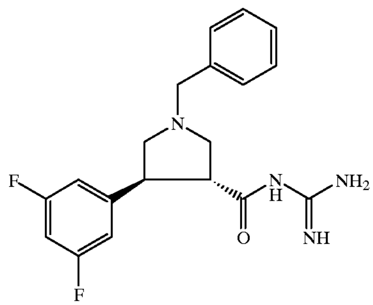 | (M + H)⁺ 359 |
| 304 | 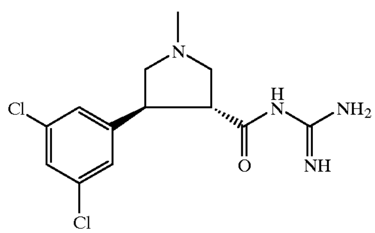 | (M + H)⁺ 316 |
| 305 | 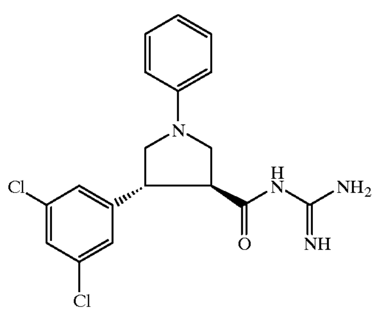 | (M + H)⁺ 378 |
| 306 | 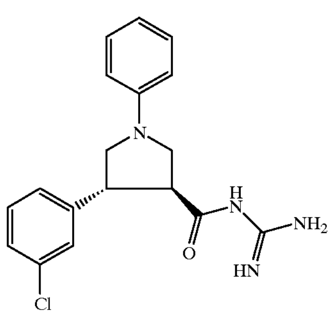 | (M + H)⁺ 344 |
| 307 | | (M + H)⁺ 406 |
| 308 | | (M + H)⁺ 420 |
| 309 | | (M + H)⁺ 391 |
| 310 | | (M + H)⁺ 377 |

| Example No. | Structure | Characterization (MS) |
|---|---|---|
| 311 | 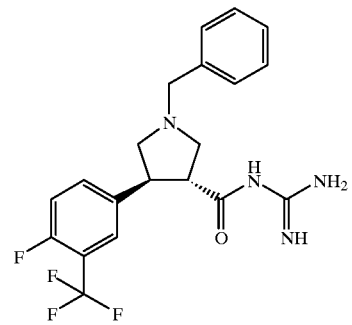 | (M + H)+ 409 |
| 312 | 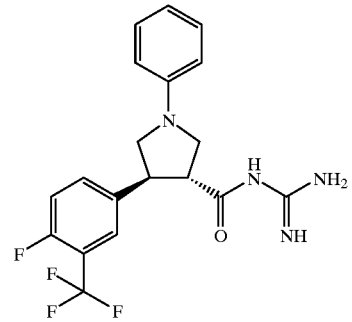 | (M + H)+ 395 |
| 313 | 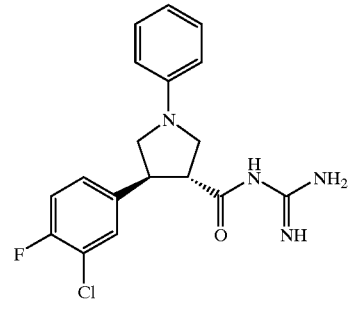 | (M + H)+ 362 |
| 314 | 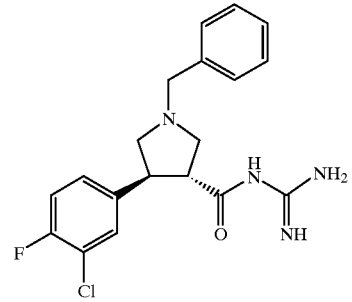 | (M + H)+ 376 |

| Example No. | Structure | Characterization (MS) |
|---|---|---|
| 315 | 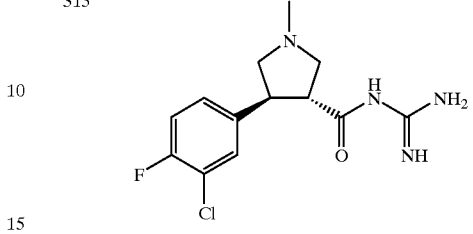 | (M + H)+ 300 |

EXAMPLE 316

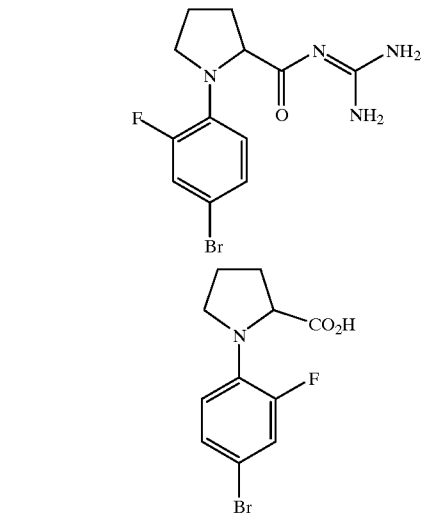

A.

2-Fluoro-4-bromo-N-phenylproline

To a solution of DL-proline (576 mg, 5 mmol) in 10/1 DMF-H$_2$O (7.5 ml) at RT were added CuI (48 mg, 0.25 mmol), Pd(PPh$_3$)$_4$ (290 mg, 0.25 mmol), K$_2$CO$_3$ (690 mg, 5 mmol), NEt$_3$ (1.4 ml, 10 mmol), triethylammonium bromide (158 mg, 0.75 mmol), and 1,4-dibromo-2-fluorobenzene. The resulting mixture was stirred in a sealed tube at 120° C. for 48 hours. The reaction mixture was cooled to room temperature and poured onto saturated K$_2$CO$_3$/Et$_2$O. The aqueous layer was extracted 3× with Et$_2$O. The pH of the aqueous layer was adjusted to 4 and extracted 3× with EtOAc. The combined organics were washed with brine, dried over MgSO$_4$, and concentrated in vacuo to produce title compound which was used without further purification: LCMS (M+1)=287.

137

B.

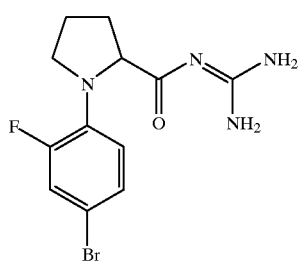

2-Fluoro-4-bromo-N-phenylproline acylguanidine

To a solution of Part A 2-fluoro-4-bromo-N-phenyl proline (215 mg, 0.75 mmol) in DMF (2.5 ml) at 25° C. was added carbonyldiimidazole (147 mg, 0.9 mmol). The resulting solution was stirred 1 hour at 25° C. To the reaction mixture was added guanidine carbonate (300 mg, 1.5 mmol). The reaction mixture was stirred overnight at 25° C. The reaction mixture was poured onto $H_2O$/EtOAc. The aqueous layer was extracted 3× with EtOAc. The combined organics were washed 2× with brine, dried over $Na_2SO_4$, and concentrated in vacuo. Preparative HPLC provided 37 mg (15% over two steps) of a white solid: LCMS (M+)=329.

EXAMPLES 317 TO 347

The following compounds were prepared employing a procedure analogous to that as set out in Example 316.

138

| Example No. | Structure | Characterization (MS) |
|---|---|---|
| 317 | | $(M + H)^+$ 380 |
| 318 | | $(M + H)^+$ 405 |
| 319 | 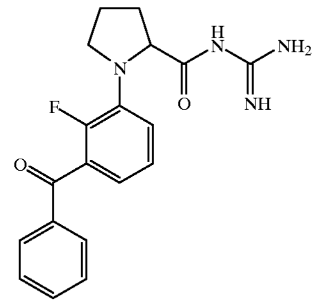 | $(M + H)^+$ 355 |
| 320 | 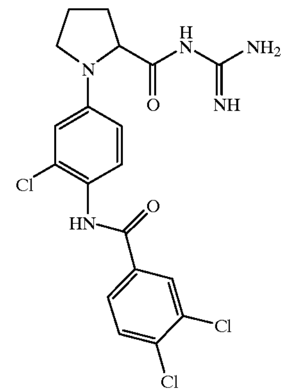 | $(M + H)^+$ 454 |
| 321 | 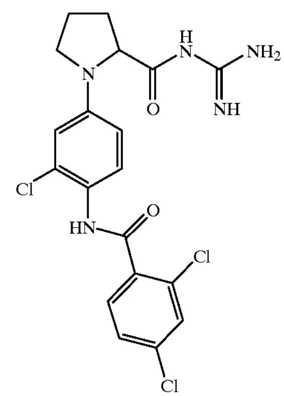 | $(M + H)^+$ 454 |
| 322 | Chiral | $(M + H)^+$ 329 |

-continued

| Example No. | Structure | Characterization (MS) |
|---|---|---|
| 323 | pyrrolidine-N-(3-bromophenyl), C(O)-NH-C(=NH)NH₂ | (M + H)⁺ 311 |
| 324 | pyrrolidine-N-(3-chlorophenyl), C(O)-NH-C(=NH)NH₂ | (M + H)⁺ 267 |
| 325 | pyrrolidine-N-(3,5-dichlorophenyl), C(O)-NH-C(=NH)NH₂ | (M + H)⁺ 301 |
| 326 | pyrrolidine-N-(3-nitrophenyl), C(O)-N=C(NH₂)NH₂ | (M + H)⁺ 278 |
| 327 | pyrrolidine-N-(2,5-dichlorophenyl), C(O)-N=C(NH₂)NH₂ | (M + H)⁺ 301 |
| 328 | pyrrolidine-N-(3-chloro-5-fluorophenyl), C(O)-N=C(NH₂)NH₂ | (M + H)⁺ 285 |
| 329 | pyrrolidine-N-(2,4-dibromophenyl), C(O)-N=C(NH₂)NH₂ | (M + H)⁺ 390 |

-continued

| Example No. | Structure | Characterization (MS) |
|---|---|---|
| 330 | pyrrolidine-N-(3-fluoro-5-trifluoromethylphenyl), C(O)-N=C(NH₂)NH₂ | (M + H)⁺ 318 |
| 331 | pyrrolidine-N-(3,5-dibromophenyl), C(O)-N=C(NH₂)NH₂ | (M + H)⁺ 389 |
| 332 | pyrrolidine-N-(2-chlorophenyl), C(O)-N=C(NH₂)NH₂ | (M + H)⁺ 267 |
| 333 | pyrrolidine-N-(2,4-dichlorophenyl), C(O)-N=C(NH₂)NH₂ | (M + H)⁺ 301 |
| 334 | pyrrolidine-N-(2,5-difluorophenyl), C(O)-N=C(NH₂)NH₂ | (M + H)⁺ 269 |
| 335 | pyrrolidine-N-(4-bromo-2-fluorophenyl), C(O)-N=C(NH₂)NH₂ | (M + H)⁺ 329 |

6,011,059

-continued

| Example No. | Structure | Characterization (MS) |
|---|---|---|
| 336 | pyrrolidine-N-(2,4-difluorophenyl), C(=O)-N=C(NH₂)NH₂ | (M + H)⁺ 269 |
| 337 | pyrrolidine-N-phenyl, C(=O)-N=C(NH₂)NH₂ | (M + H)⁺ 233 |
| 338 | pyrrolidine-N-(2-methylphenyl), C(=O)-N=C(NH₂)NH₂ | (M + H)⁺ 247 |
| 339 | pyrrolidine-N-(3-methylphenyl), C(=O)-N=C(NH₂)NH₂ | (M + H)⁺ 247 |
| 340 | pyrrolidine-N-(4-methylphenyl), C(=O)-N=C(NH₂)NH₂ | (M + H)⁺ 247 |
| 341 | pyrrolidine-N-(4-methoxyphenyl), C(=O)-N=C(NH₂)NH₂ | (M + H)⁺ 263 |

-continued

| Example No. | Structure | Characterization (MS) |
|---|---|---|
| 342 | pyrrolidine-N-(3,5-bis(trifluoromethyl)phenyl), C(=O)-N=C(NH₂)NH₂ | (M + H)⁺ 269 |
| 343 | pyrrolidine-N-(2,3-dichlorophenyl), C(=O)-N=C(NH₂)NH₂ | (M + H)⁺ 301 |
| 344 | pyrrolidine-N-(4-isopropylphenyl), C(=O)-N=C(NH₂)NH₂ | (M + H)⁺ 275 |
| 345 | pyrrolidine-N-(3-trifluoromethylphenyl), C(=O)-N=C(NH₂)NH₂ | (M + H)⁺ 301 |
| 346 | pyrrolidine-N-(3-hydroxyphenyl), C(=O)-N=C(NH₂)NH₂ | (M + H)⁺ 249 |
| 347 | pyrrolidine-N-(4-trifluoromethylphenyl), C(=O)-N=C(NH₂)NH₂ | (M + H)⁺ 301 |

EXAMPLE 348

A.

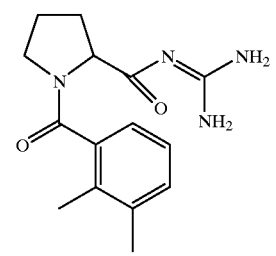

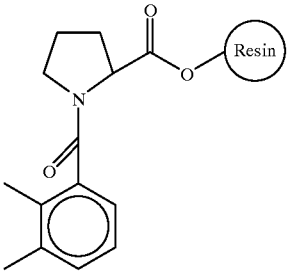

To a solution of 2,3-dimethylbenzoic acid (113 mg, 0.75 mmol) in DMF (1 ml) at 25° C. was added PyBoP (367 mg, 0.83 mmol). The reaction mixture was shaken at 25° C. for 20 minutes. To the reaction mixture was added resin-supported DL-proline ester (0.6 mmol/g, 416 mg, 0.25 mmol). The resulting mixture was shaken overnight at 25° C. The resin was washed 3x each with $CH_2Cl_2$, MeOH, and DMF. Following a final wash with $CH_2Cl_2$, the resin was allowed to dry under vacuum. The resulting title compound was used without further purification.

B.

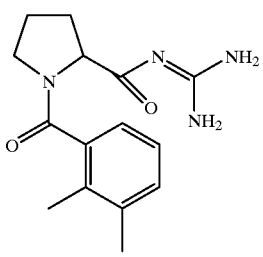

To a suspension of Part A compound (0.25 mmol) in DMF (2.5 ml) at 25° C. was added guanidine (44 mg, 0.75 mmol). The reaction mixture was shaken overnight at 25° C. The resin beads were washed with $CH_2Cl_2$ (25 ml). The crude reaction mixture was filtered through a diatomaceous earth cartridge, eluting with $CH_2Cl_2$ (25 ml). The solvents were removed in vacuo. Purification of the crude residue via preparative HPLC (as described in Example 258 Step C) yielded 32 mg (44% over two steps) of a white solid: LCMS (M+)=288.

EXAMPLES 349 TO 360

The following compounds were prepared employing a procedure analogous to that set out in Example 348.

| Example No. | Structure | Characterization (MS) |
|---|---|---|
| 349 | 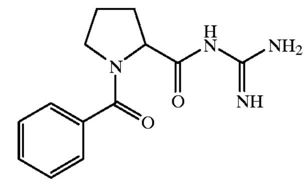 | $(M + H)^+$ 261 |
| 350 | 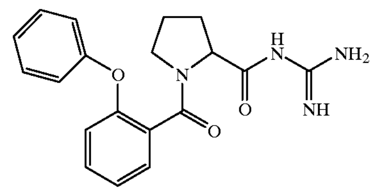 | $(M + H)^+$ 353 |
| 351 | 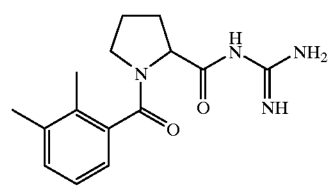 | $(M + H)^+$ 289 |
| 352 | 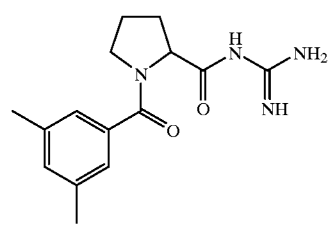 | $(M + H)^+$ 289 |
| 353 | 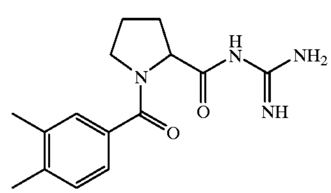 | $(M + H)^+$ 289 |
| 354 | 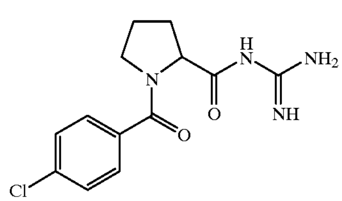 | $(M + H)^+$ 295 |
| 355 | 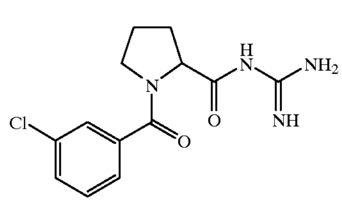 | $(M + H)^+$ 295 |

-continued

| Example No. | Structure | Characterization (MS) |
|---|---|---|
| 356 | 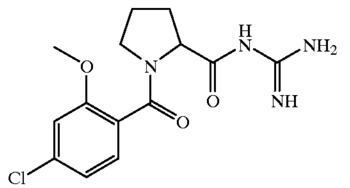 | (M + H)+ 325 |
| 357 | 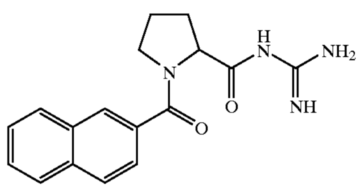 | (M + H)+ 311 |
| 358 | 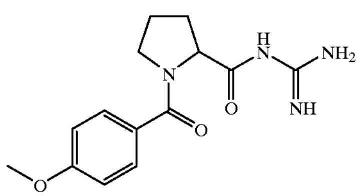 | (M + H)+ 291 |
| 359 | 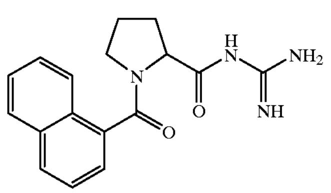 | (M + H)+ 311 |
| 360 | 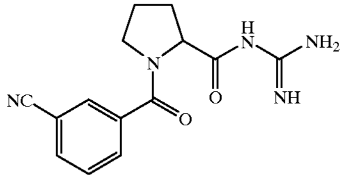 | (M + H)+ 286 |

EXAMPLE 361

A.

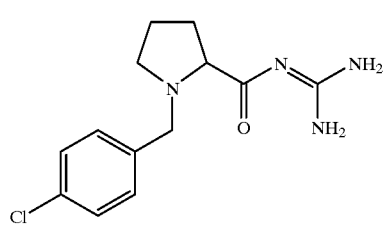

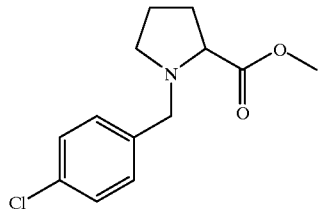

A solution of DL-Proline-OMe hydrochloride (100 mg, 0.6 mmol, 1.0 equiv.), TEA (253 μl, 1.81 mmol, 3.0 equiv.), and p-chloro-benzyl bromide (123 mg. 0.6 mmol, 1.0 equiv.) in dichloroethane (5 ml) was heated to 80° C. for 20 min, then RT for 3 hr. The solvent was removed under reduced pressure to give title compound which was used without purfication in the next step.

B.

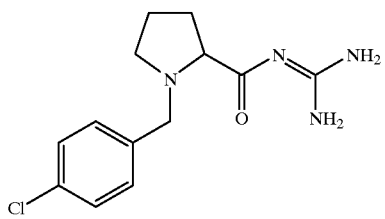

The crude Part A product mixture from G was redissolved in DMF (5 ml) and guanidine free base (100 mg, excess) was added, and the reaction mixture was stirred for 18 hr. The solvent was removed under high vacuum and the crude product was purified by Prep-HPLC (as described in Example 258 Step C) to give the title acyl guanidine.

Yield: 151 mg, 50%. LR-MS calcd 280, found (M+H)+ 281.

EXAMPLES 362 TO 372

The following compounds were prepared employing a procedure analogous to that set out in Example 361.

| Example No. | Structure | Characterization (MS) |
|---|---|---|
| 362 | 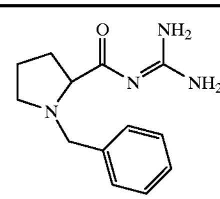 | (M + H)+ 247 |
| 363 | 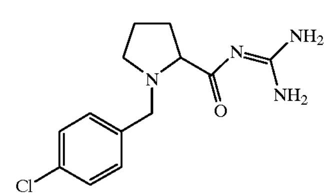 | (M + H)+ 281 |

-continued

| Example No. | Structure | Characterization (MS) |
|---|---|---|
| 364 | 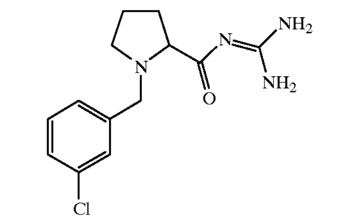 | (M + H)⁺ 281 |
| 365 | 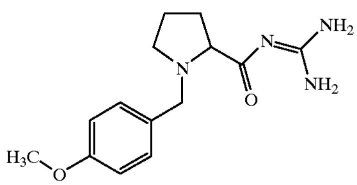 | (M + H)⁺ 279 |
| 366 | 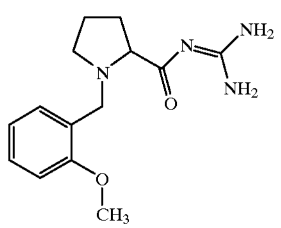 | (M + H)⁺ 279 |
| 367 | 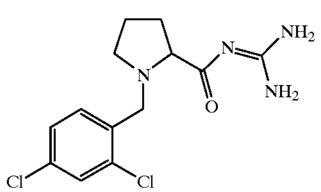 | (M + H)⁺ 318 |
| 368 | 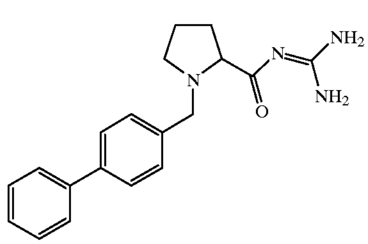 | (M + H)⁺ 323 |
| 369 | 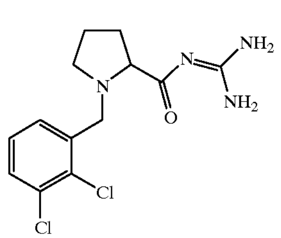 | (M + H)⁺ 318 |

-continued

| Example No. | Structure | Characterization (MS) |
|---|---|---|
| 370 | | (M + H)⁺ 318 |
| 371 | | (M + H)⁺ 318 |
| 372 | | (M + H)⁺ 323 |

What is claimed is:
1. A compound having the structure

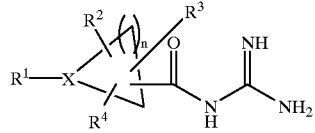

wherein n is an integer from 1 to 5;

X is C—R⁵ wherein R⁵ is H, halo, alkenyl, alkynyl, alkoxy, alkyl, aryl or heteroaryl;

R¹ is H, alkyl, alkenyl, alkynyl, alkoxy, alkenyloxy, alkynyloxy, (alkyl or aryl)₃Si (where each alkyl or aryl group is independent), cycloalkyl, cycloalkenyl, amino, alkylamino, alkenylamino, alkynylamino, arylalkylamino, aryl, arylalkyl, arylamino, aryloxy, cycloheteroalkyl, cycloheteroalkylalkyl, heteroaryl, heteroarylamino, heteroaryloxy, arylthio, arylsulfinyl, arylsulfonyl, thio, alkylthio, alkylsulfinyl, alkylsulfonyl, heteroarylthio, heteroarylsulfinyl, heteroarylsulfonyl, halogen, haloalkyl, polyhaloalkyl, polyhaloalkoxy, aminothio, aminosulfinyl, aminosulfonyl, alkylsulfonylamino, alkenylsulfonylamino, alkynylsulfonylamino, arylsulfonylamino, heteroarylsulfonylamino, alkylaminocarbonyl, arylaminocarbonyl, heteroarylaminocarbonyl, hydroxy, acyl, carboxy, aminocarbonyl, alkylcarbonyl, alkoxycarbonyl, alkylcarbonyloxy, alkylcarbonylamino, arylcarbonyl, arylcarbonyloxy, arylcarbonylamino, heteroarylcarbonyl, heteroaryl-carbonyloxy, heteroarylcarbonylamino, cyano, nitro, alkenylcarbonylamino, alkynylcarbonylamino, alkylaminocarbonylamino, alkenylaminocarbonylamino, alkynylaminocarbonylamino, arylaminocarbonylamino, heteroarylaminocarbonylamino, alkoxycarbonylamino, alkenyloxycarbonylamino, alkynyloxycarbonylamino, aryloxycarbonylamino, heteroaryloxycarbonylamino, aminocarbonylamino, alkylaminocarbonyloxy, alkoxycarbonylamino; 1,1-(alkoxyl or aryloxy)$_2$alkyl (where the two aryl or alkyl substituents can be independently defined, or linked to one another to form a ring), S(O)$_2$R$^6$R$^7$, —NR$^6$(C=NR$^7$)alkyl, —NR$^6$(C=NR$^7$) alkenyl, —NR$^6$(C=NR$^7$)alkynyl, —NR$^6$(C=NR$^7$) heteroaryl, —NR$^8$(C=NCN)-amino,

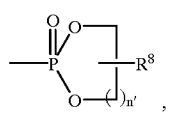

pyridine-N-oxide,

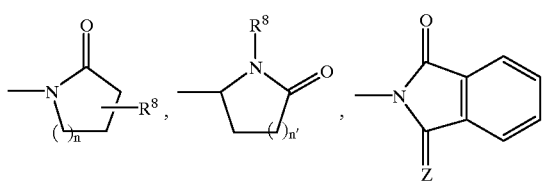

(where Z is O or H$_2$ and n' is 0, 1, 2 or 3) or

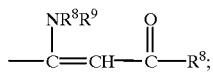

tetrazolyl, imidazole, oxazole or triazole, —PO(R$^{13}$)(R$^{14}$), (where R$^{13}$ and R$^{14}$ are independently alkyl, aryl, alkoxy, aryloxy, heteroaryl, heteroarylalkyl, heteroaryloxy, heteroarylalkoxy, cycloheteroalkyl, cycloheteroalkylalkyl, cycloheteroalkoxy, or cycloheteroalkylalkoxy);

R$^6$, R$^7$, R$^8$ and R$^9$ are independently hydrogen, alkyl, haloalkyl, aryl, heteroaryl, arylalkyl, cycloalkyl or (cycloalkyl)alkyl, or cycloheteroalkyl;

and R$^1$ is optionally substituted with from one to five substituents

R$^2$, R$^3$ and R$^4$ are the same or different and are independently any of the groups set out for R$^1$ and is optionally substituted with from one to five substituents or R$^1$. R$^2$, R$^3$ and/or R$^4$ is optionally joined together with the carbons to which they are attached to form a non-aromatic ring;

or a pharmaceutically acceptable salt thereof, a prodrug ester thereof, or a stereoisomers thereof;

with the proviso that (1) at least one of R$^1$, R$^2$, R$^3$, R$^4$ is other than H; (2) R$^1$, R$^2$, R$^3$ and R$^4$ is other than alkyl having an amino substituent.

2. The compound as defined in claim 1 wherein at least one of R$^1$, R$^2$, R$^3$ and R$^4$ is aryl or heteroaryl.

3. The compound as defined in claim 1 wherein R$^1$ is aryl or heteroaryl.

4. The compound as defined in claim 1 wherein the moiety

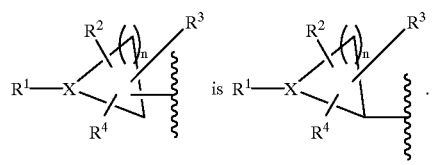

5. The compound as defined in claim 1 wherein R$^2$ and R$^3$ are independently H, lower alkyl, lower alkoxy or aryl, and R$^4$ and R$^5$ are each hydrogen.

6. The compound as defined in claim 1 wherein n is 1.

7. The compound as defined in claim 1 wherein n is 1, R$^2$ and R$^3$ are independently H or lower alkyl, and R$^4$ and R$^5$ are each H, and R$^1$ is aryl or heteroaryl.

8. The compound as defined in claim 1 wherein R$^1$ is phenyl, substituted phenyl or heteroaryl.

9. The compound as defined in claim 1 wherein R$^1$ is phenyl, halophenyl, dihalophenyl, alkylphenyl, nitrophenyl, dialkoxyphenyl, trifluoromethylphenyl, biphenyl, heteroarylphenyl, cycloheteroalkylphenyl, alkylthiophenyl, trialkoxyphenyl or halo(dialkoxy)phenyl, phenylalkyl, 2,3-dihydrobenzofuran

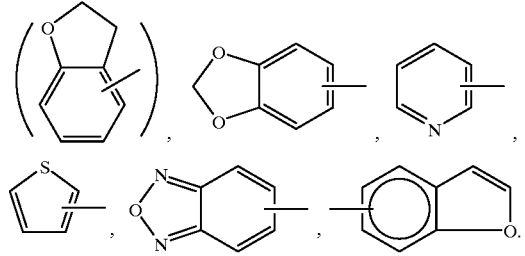

10. The compound as defined in claim 1 wherein R$^1$, R$^2$, R$^3$ and/or R$^4$ is is optionally joined together with the carbons to which they are attached to form a non-aromatic ring.

11. The compounds as defined in claim 1 wherein

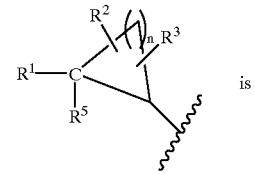

is

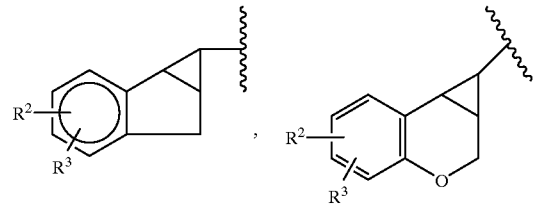

-continued

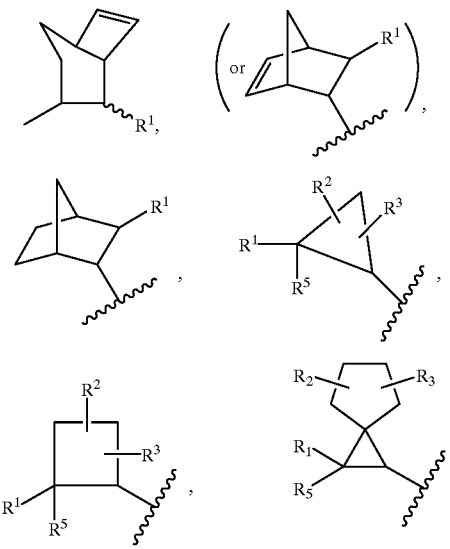

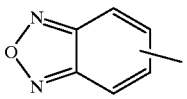
(m = 2 to 5)

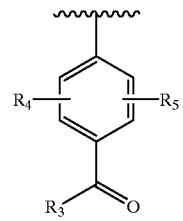

where $R_1$ and $R_2$ are independently H or Cl,

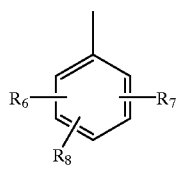

where $R_3$ is $NH_2$, $CH_3$, $CF_3$ and $R_4$ and $R_5$ are independently H, 2-F, 2,5-diF, 2-$CF_3$, 3-$CF_3$,

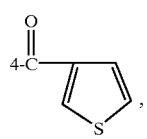

where $R_6$, $R_7$ and $R_8$ are independently H, 2-$NO_2$, 2-$CF_3$, 3-$CF_3$, 3-CN—, 5-$CF_3$, 4-$NO_2$, 4-O=CH—,

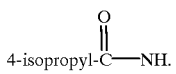

2-$CH_3O$—, 3-$CH_3O$—, 4-$CH_3O$—, 5-$CH_3O$—, 6-$CH_3O$—, 3-OH, 4-$(CH_3)_2N$—, 4-OH, 2-F, 3-F, 4-F, 5-F, 6-F, 4-isopropyl, 2-Br, 5-Br, 3-Br, 4-$CH_3SO_2$, 4-benzyloxy, 3-$CH_3CH_2$—, 2-$CH_3$—, 3-$CH_3$—, 6-$CH_3$—, 4-t-butyl, 4-$CH_3CH_2O$— 4-cyclohexyl, 4-phenoxy, 4-$CH_3$—$SO_2$—NH—,

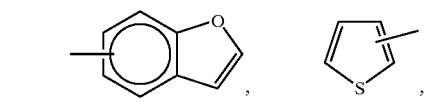

12. The compound as defined in claim 1 wherein $R^1$ is phenyl, 4-bromophenyl, 4-chlorophenyl, 3-bromophenyl, 3,5-dimethoxyphenyl, 4-methylphenyl, 2,4-dichlorophenyl, 3-nitrophenyl, 2-chlorophenyl, 3-chlorophenyl, 2,5-dimethylphenyl, 2-methylphenyl, 3-methylphenyl, 4-methylphenyl, 2,3-dimethoxy phenyl, 4-trifluoromethylphenyl, 3-trifluoromethoxyphenyl, 4-biphenyl, 2-bromo-4,5-dimethoxyphenyl, 4-methylthiophenyl, 3,4,5-trimethoxyphenyl, 4-fluorophenyl, 2-chloro-3,4-dimethoxyphenyl, 4-nitrophenyl, benzyl, 3-methoxyphenyl, 4-methoxyphenyl, 2-methoxyphenyl, 3-bromo-4-fluorophenyl, 3-ethoxyphenyl, 3-trifluoromethylphenyl, 3,5-difluorophenyl, 3,5-dichlorophenyl, 3,5-ditrifluoromethylphenyl, 3-trifluorophenyl, 3-(N-pyrrolyl)phenyl, 3-(N-pyrrolidinyl)phenyl, 3-(N-pyrazolinyl)phenyl, 3-(N-imidazolyl)phenyl,

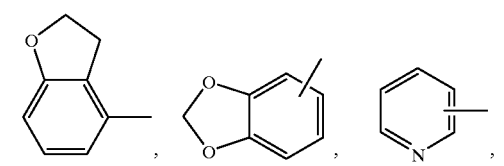

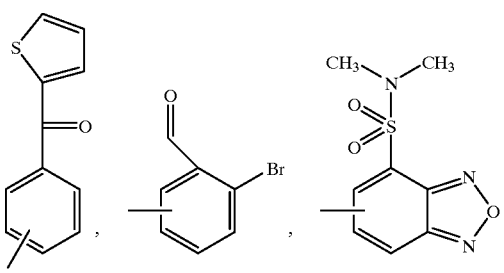

13. The compound as defined in claim 1 wherein n is 1, X is CH, $R^2$ and $R^3$ are independently lower alkyl, and $R^1$ is dihydrobenzofuran.
14. The compound as defined in claim 1 having the formula
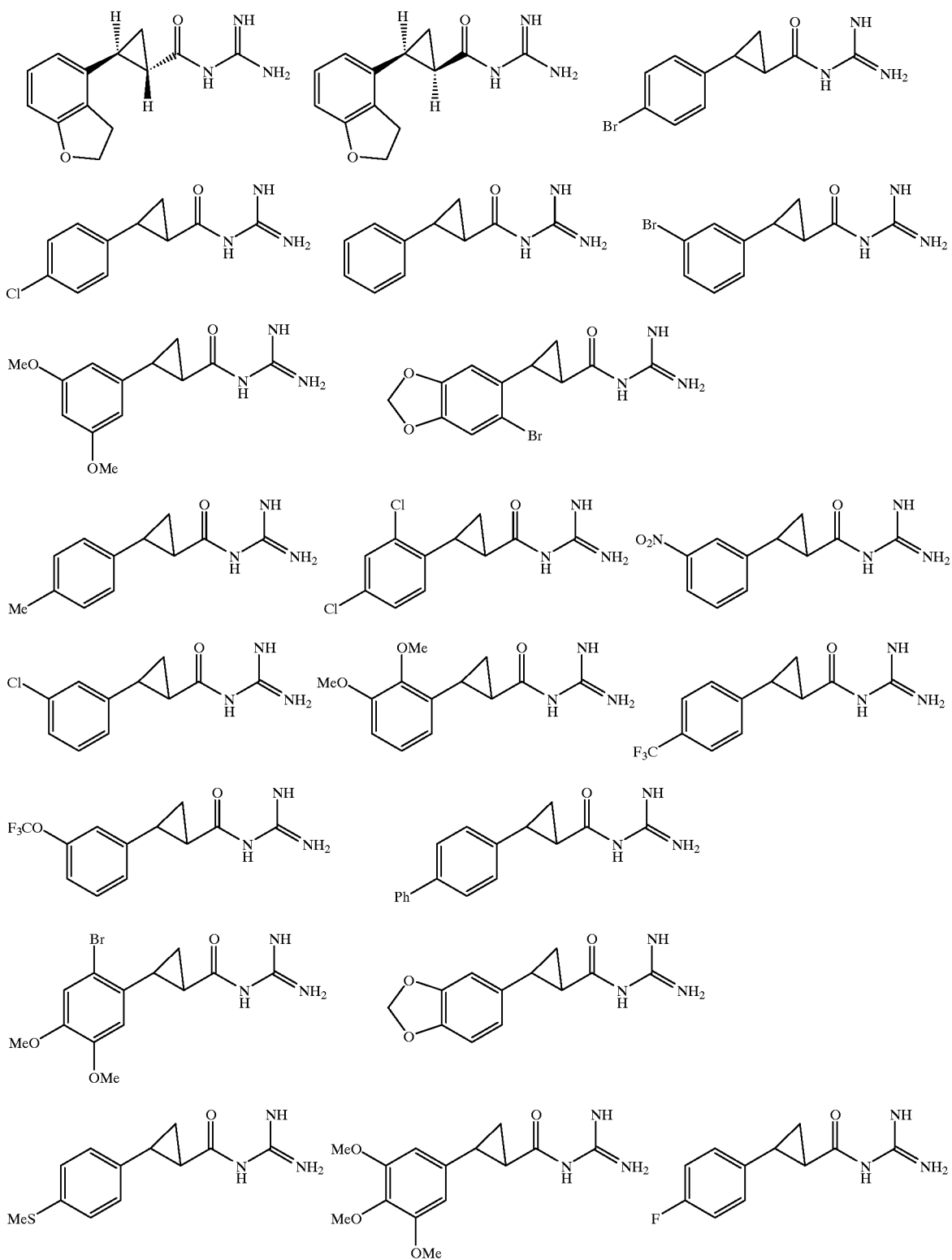

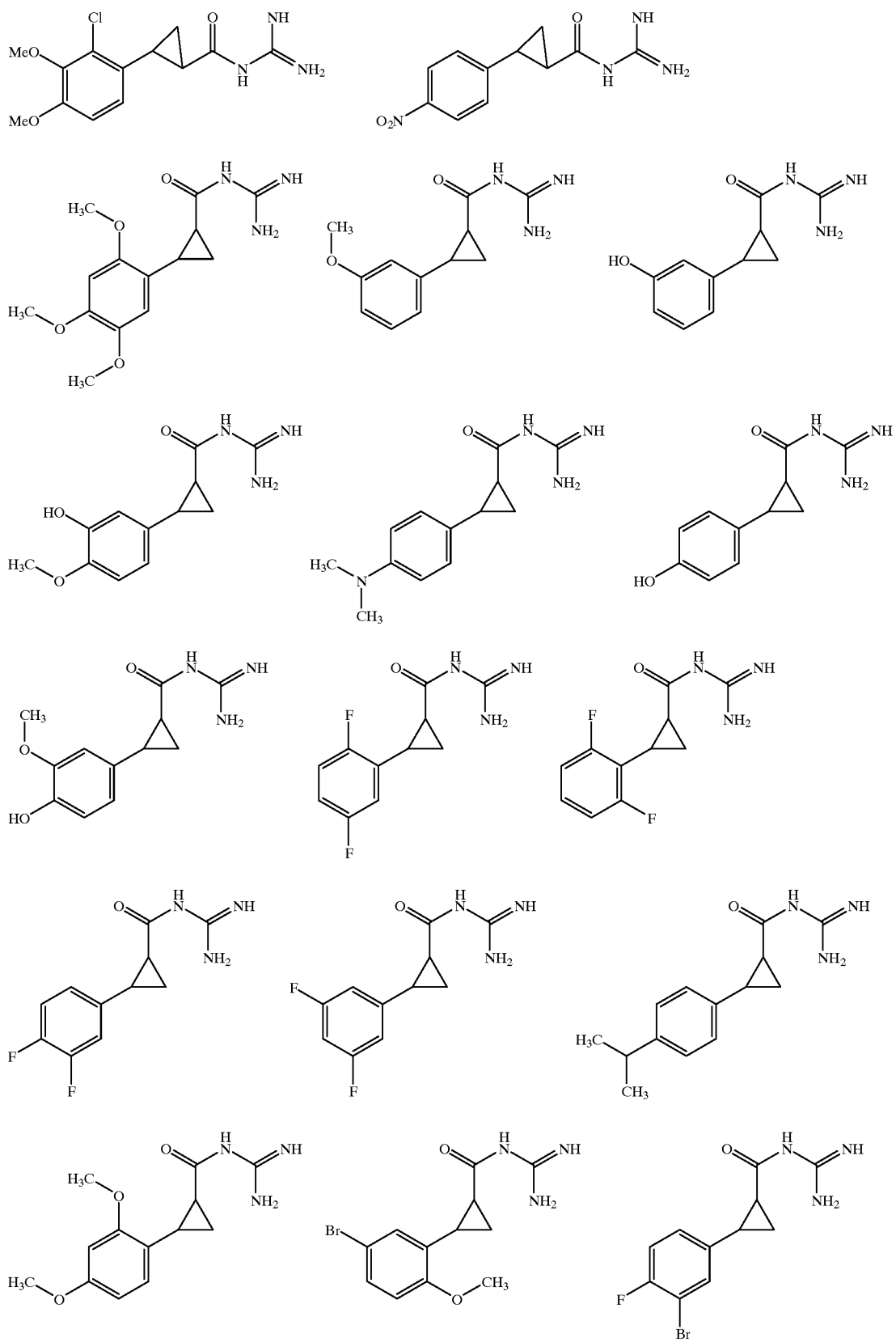

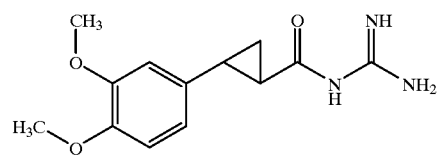
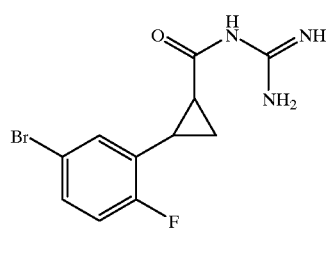
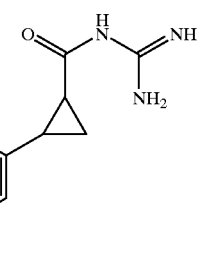
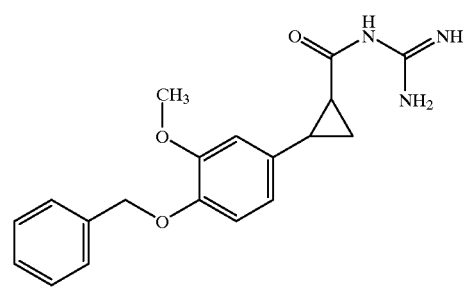
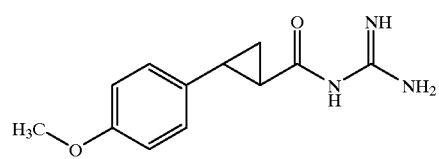
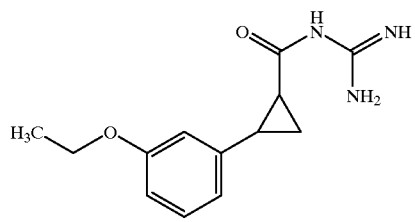
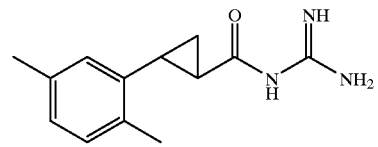
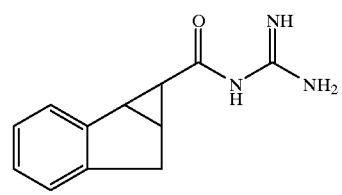
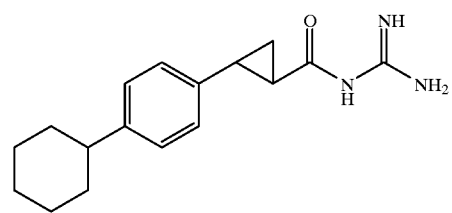
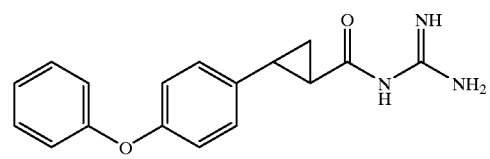
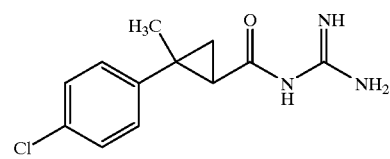
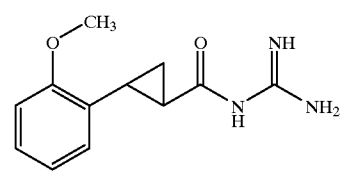
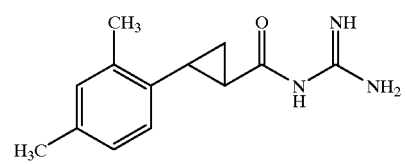
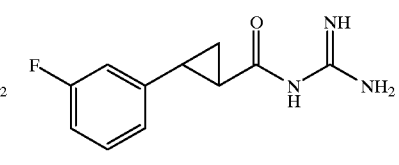
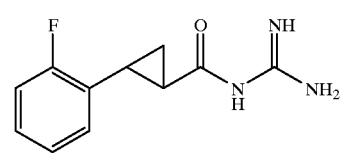
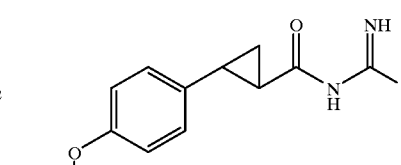
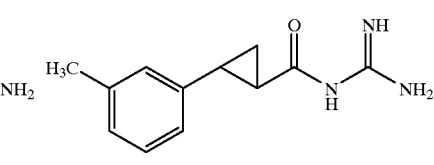
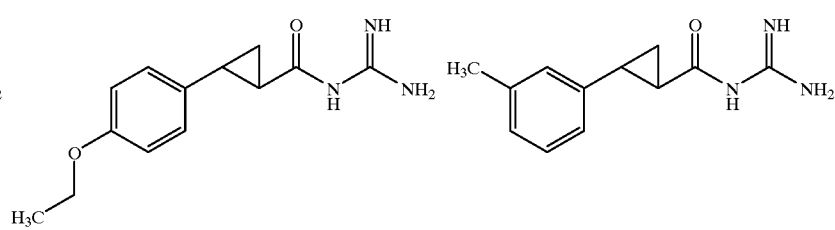

159
160
-continued
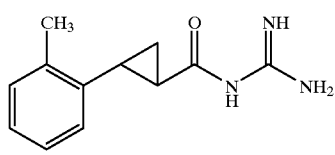
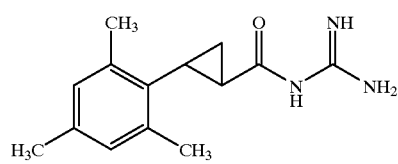
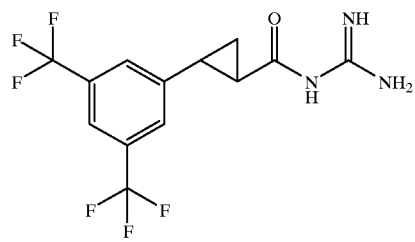
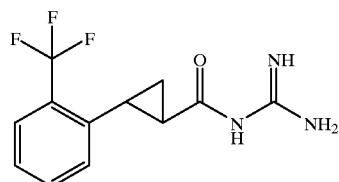
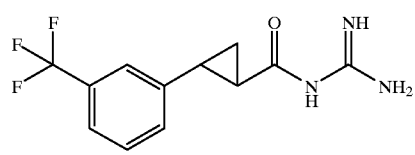
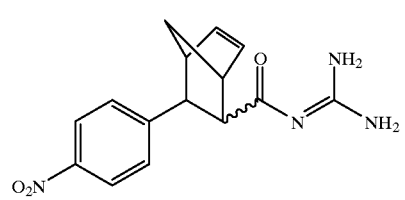
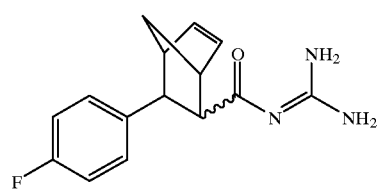
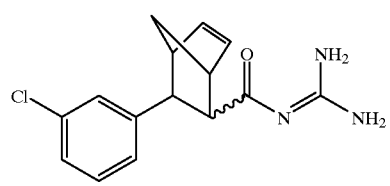
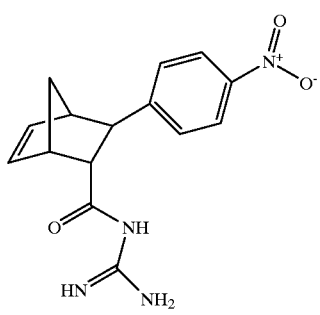
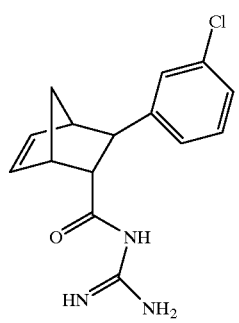
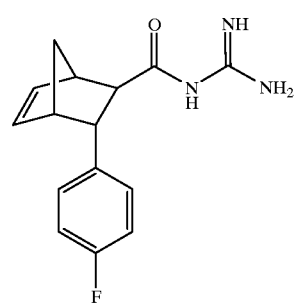
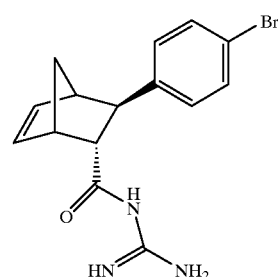
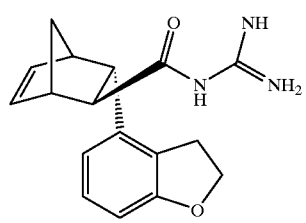
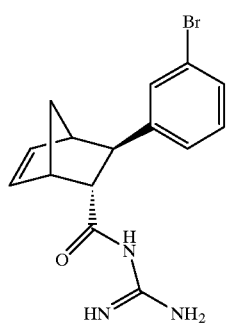
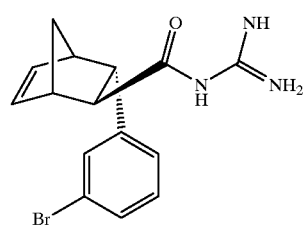

-continued
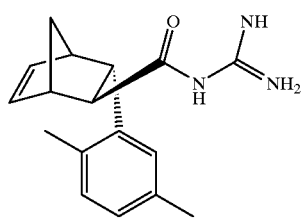
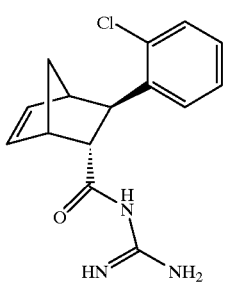
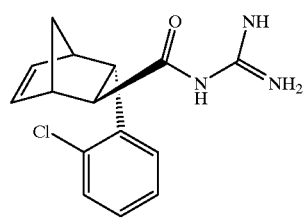
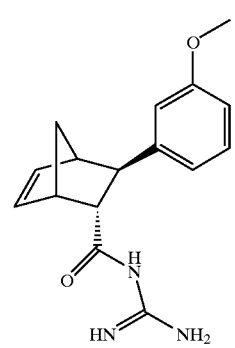
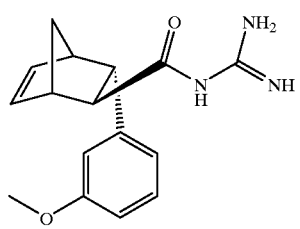
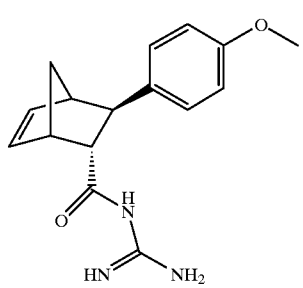
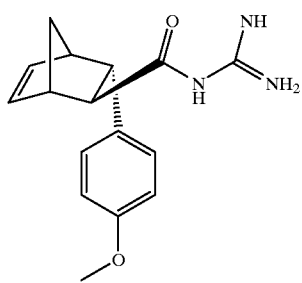
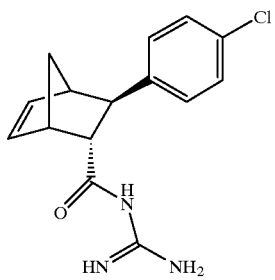
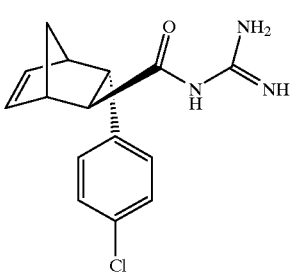
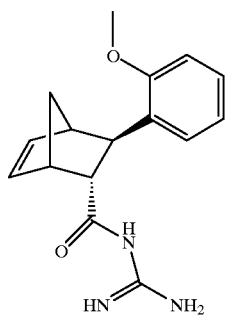
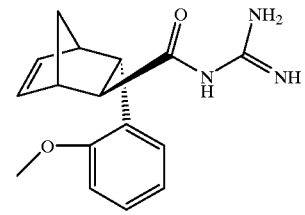
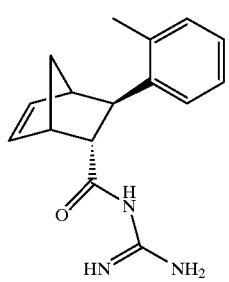
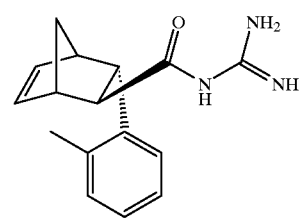
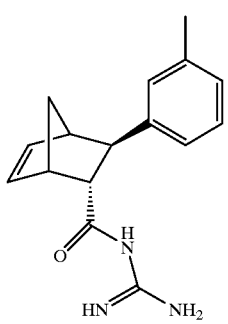
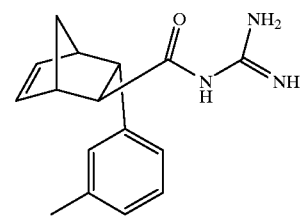
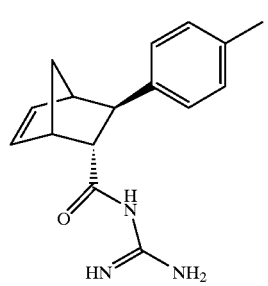
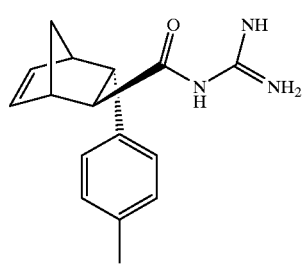

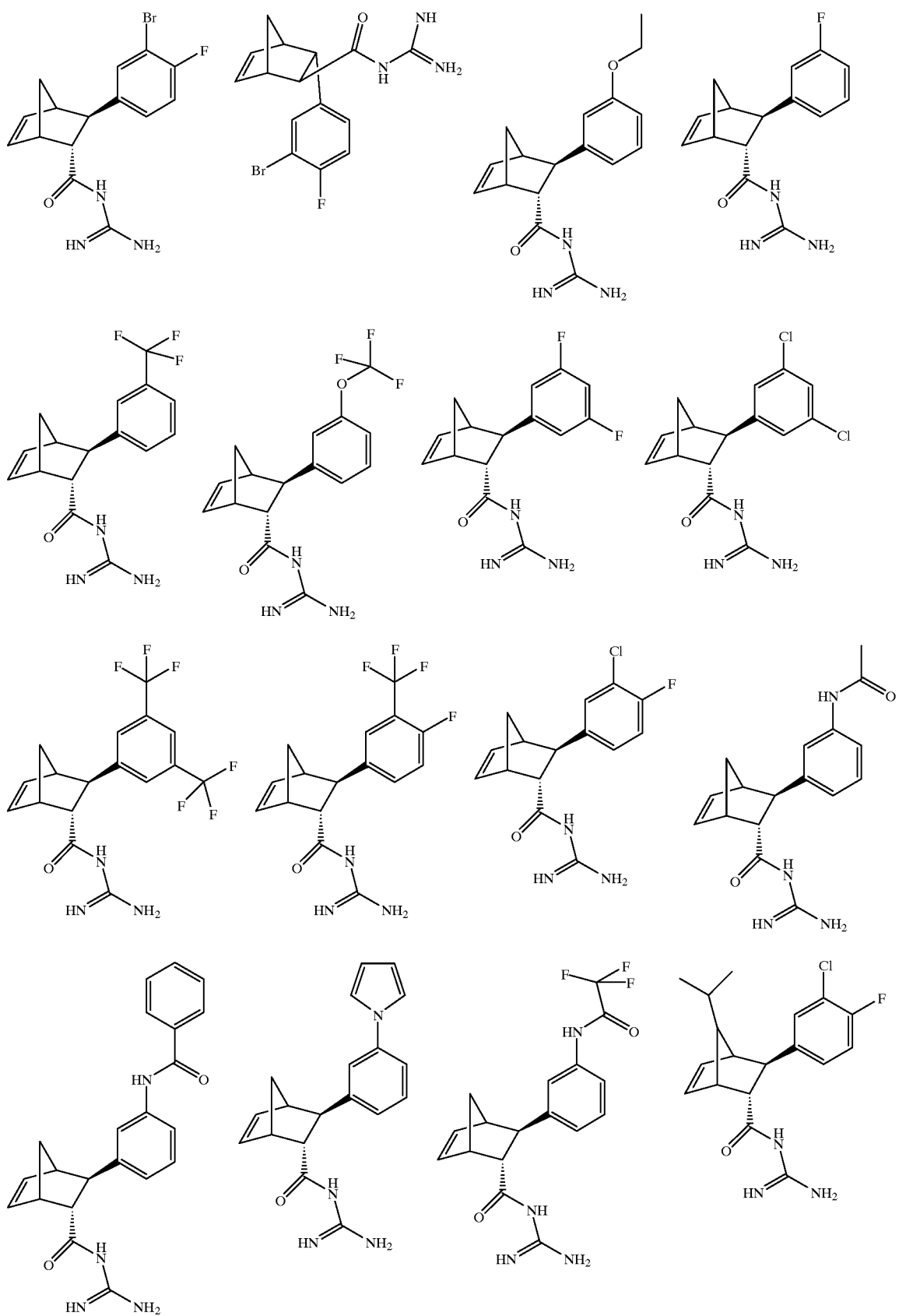

165 166
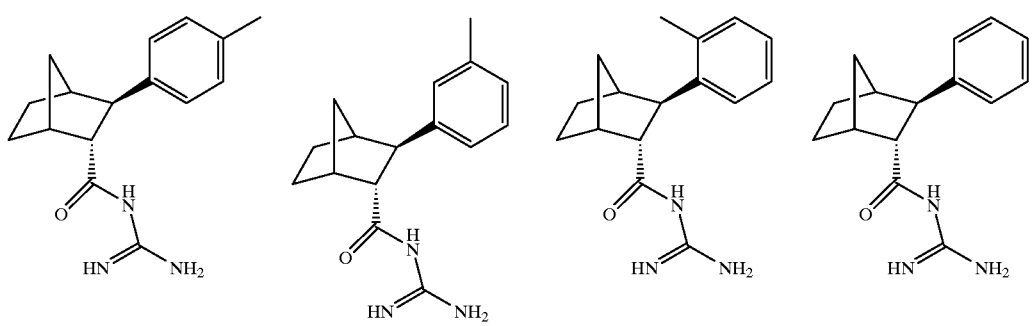
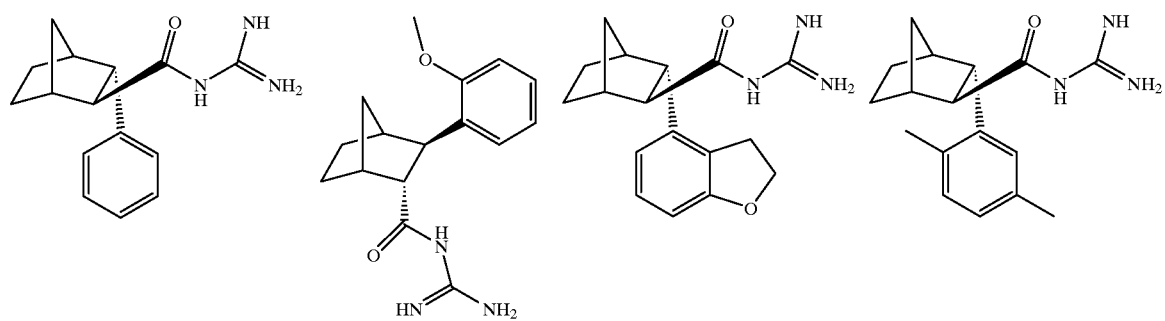
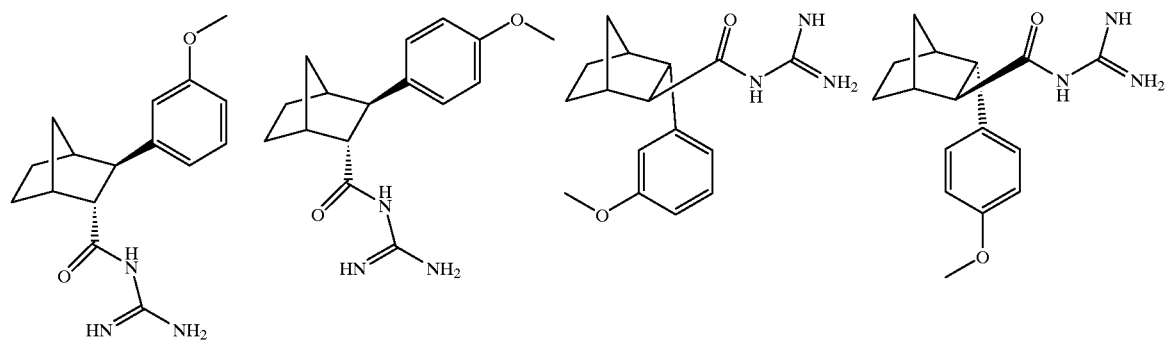
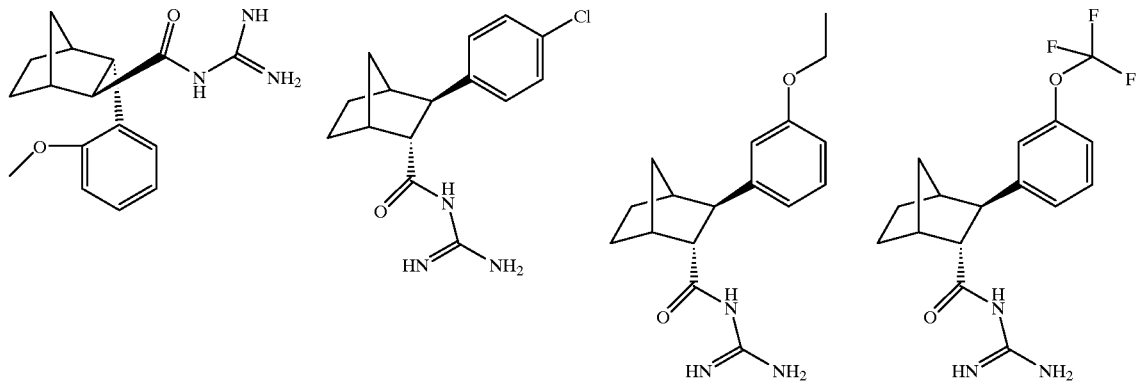

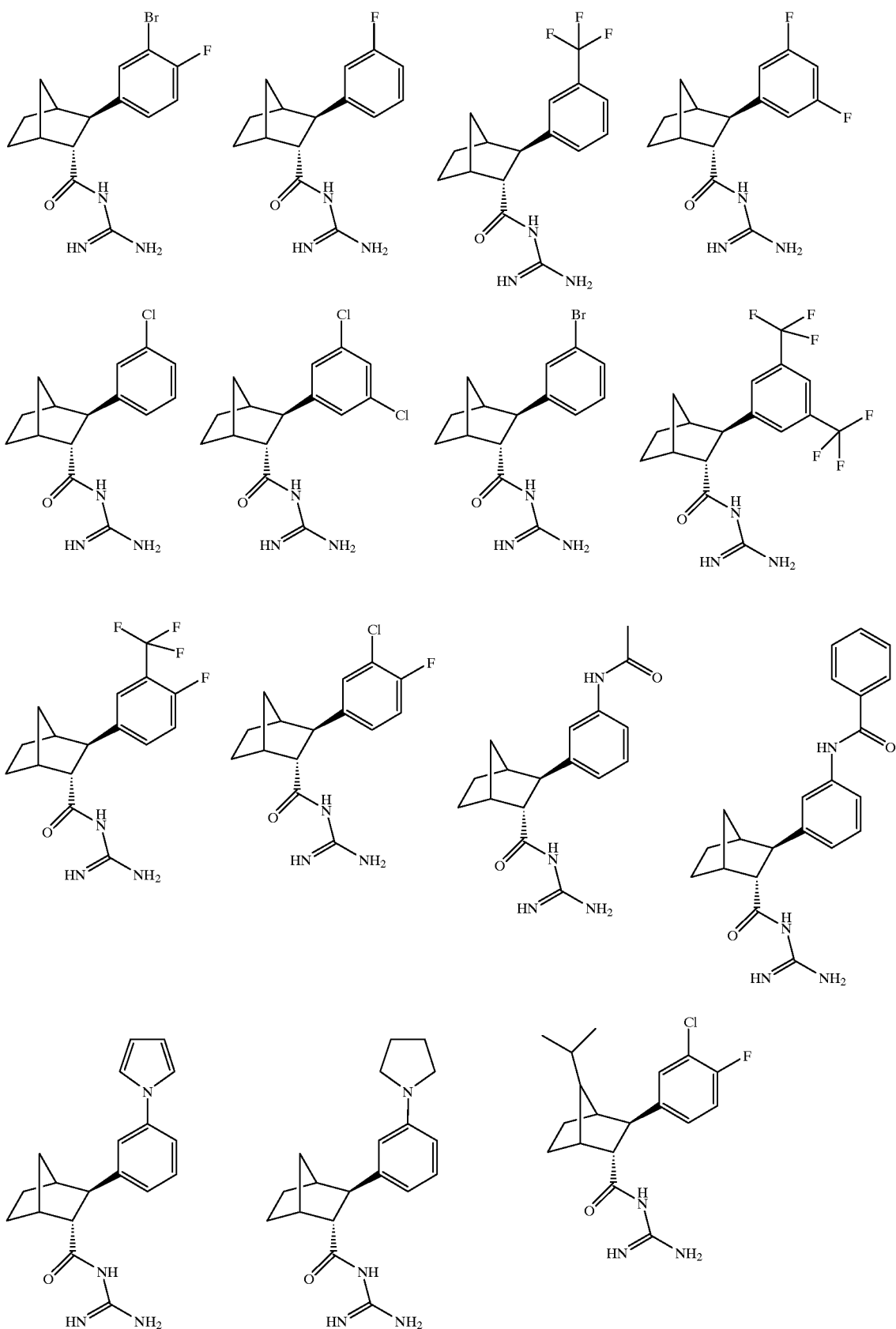

169 170
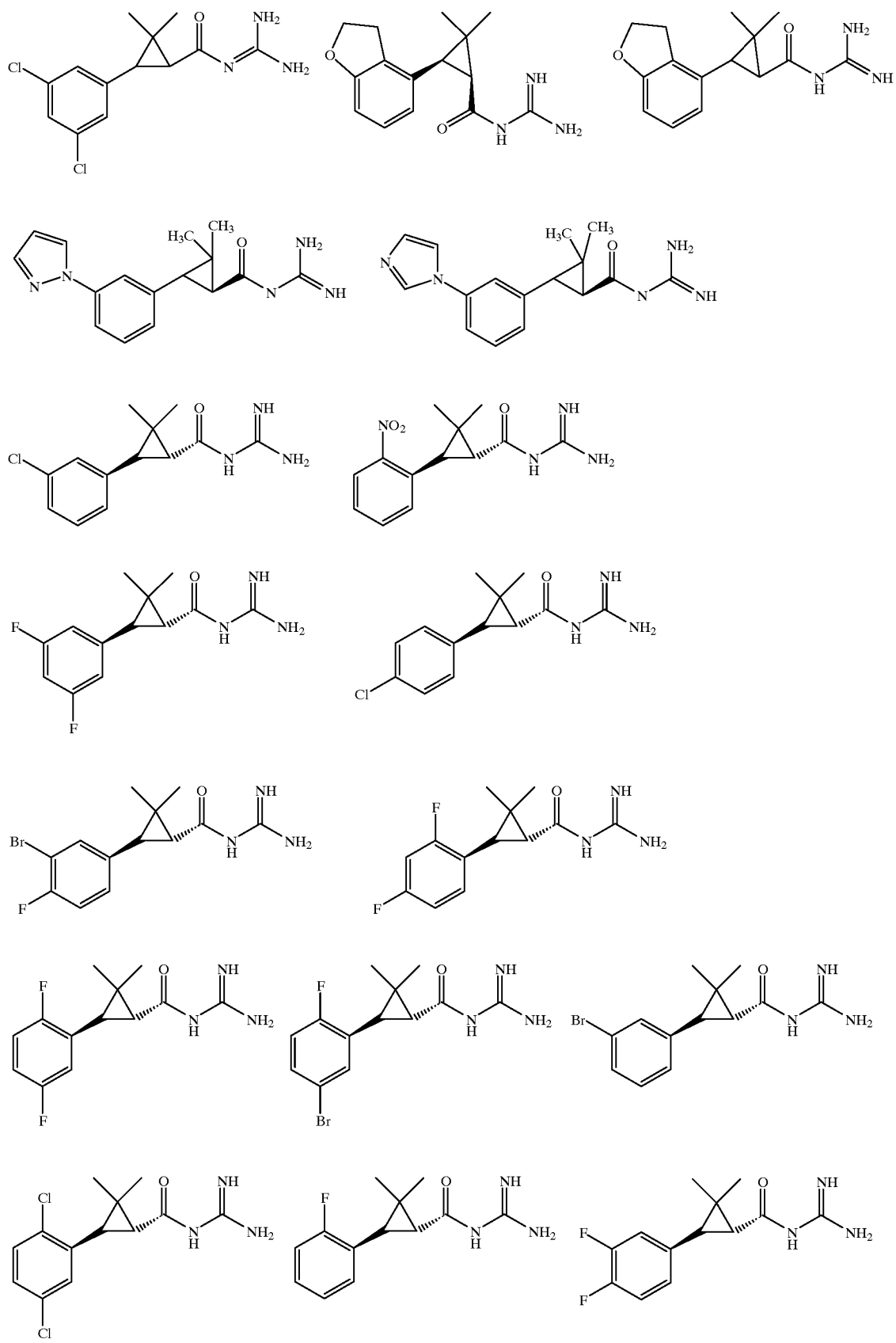

171              -continued           172
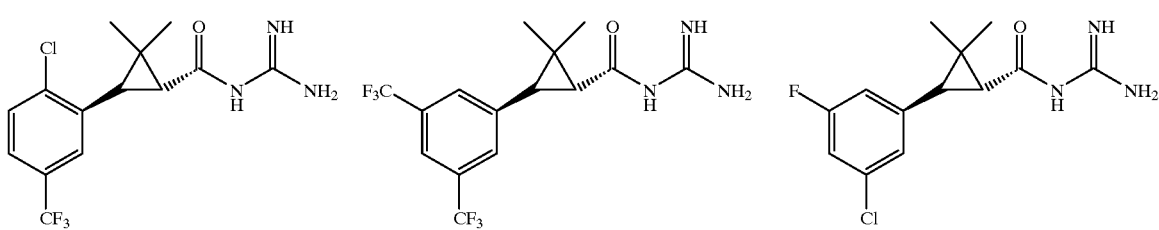
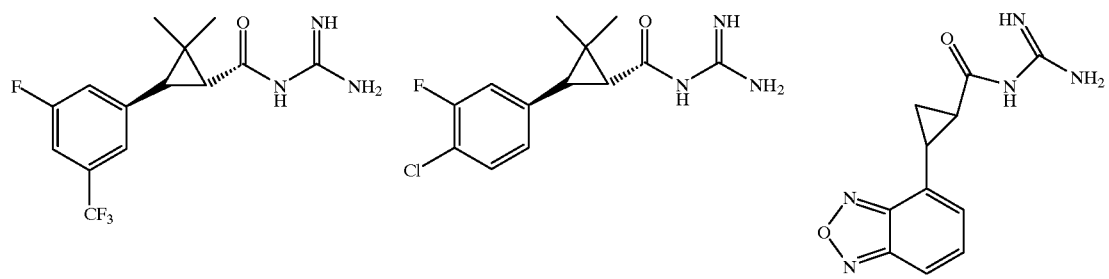
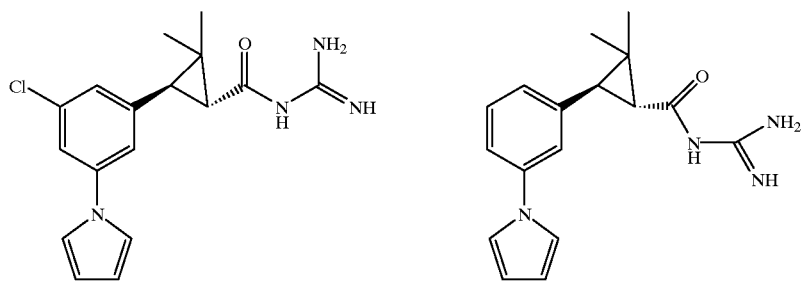
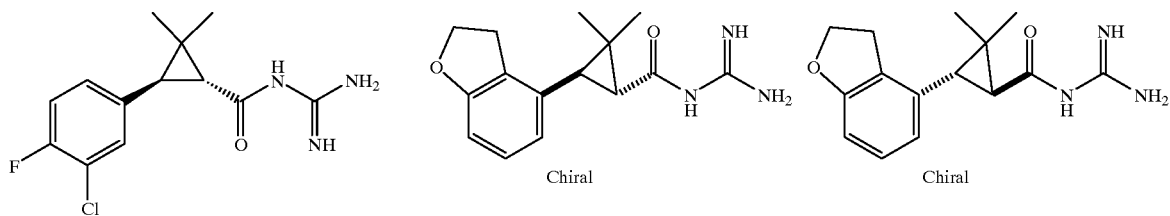
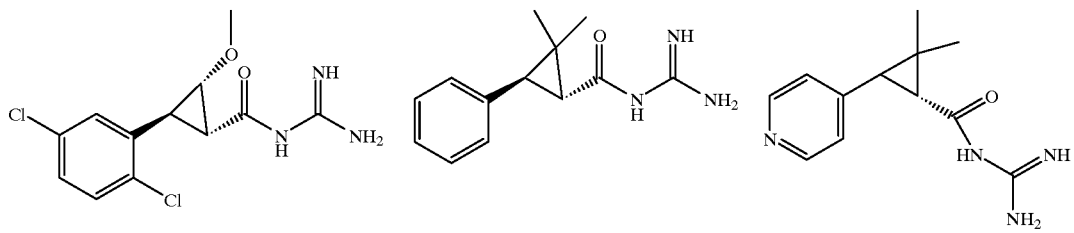
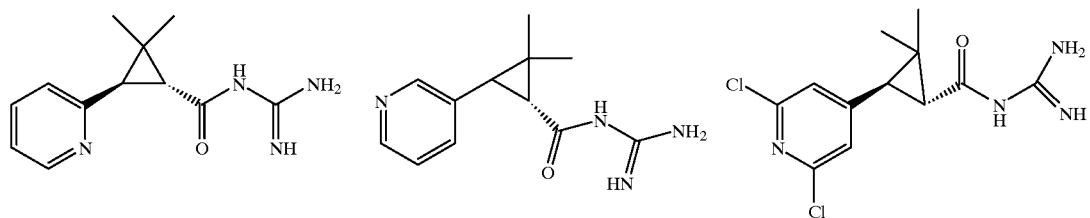

173
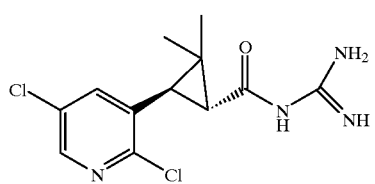
-continued
174
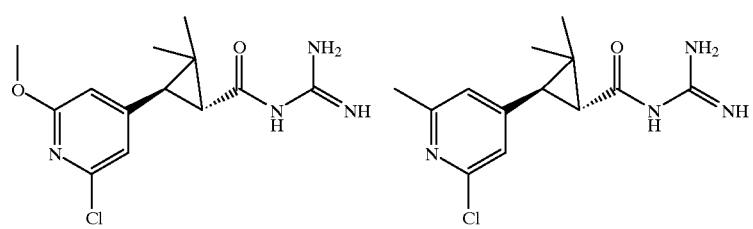
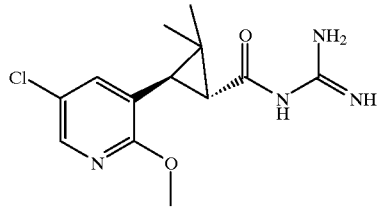
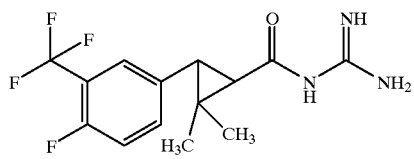
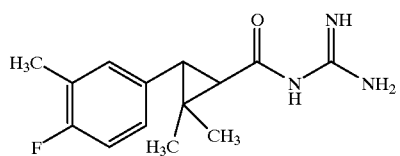
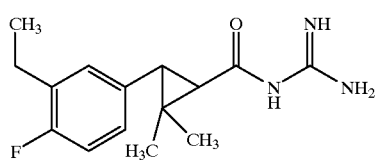
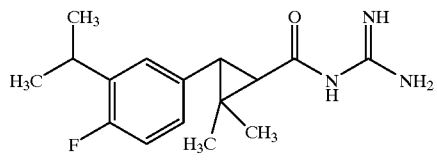
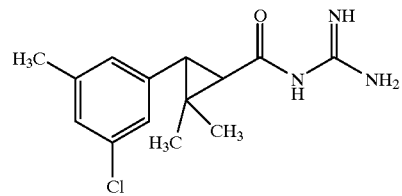
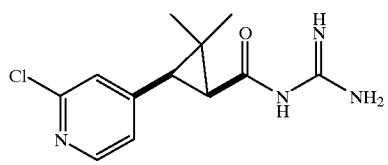
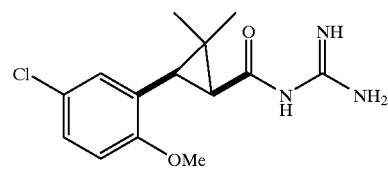
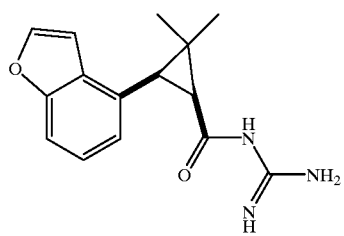
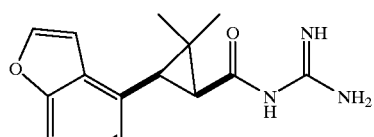

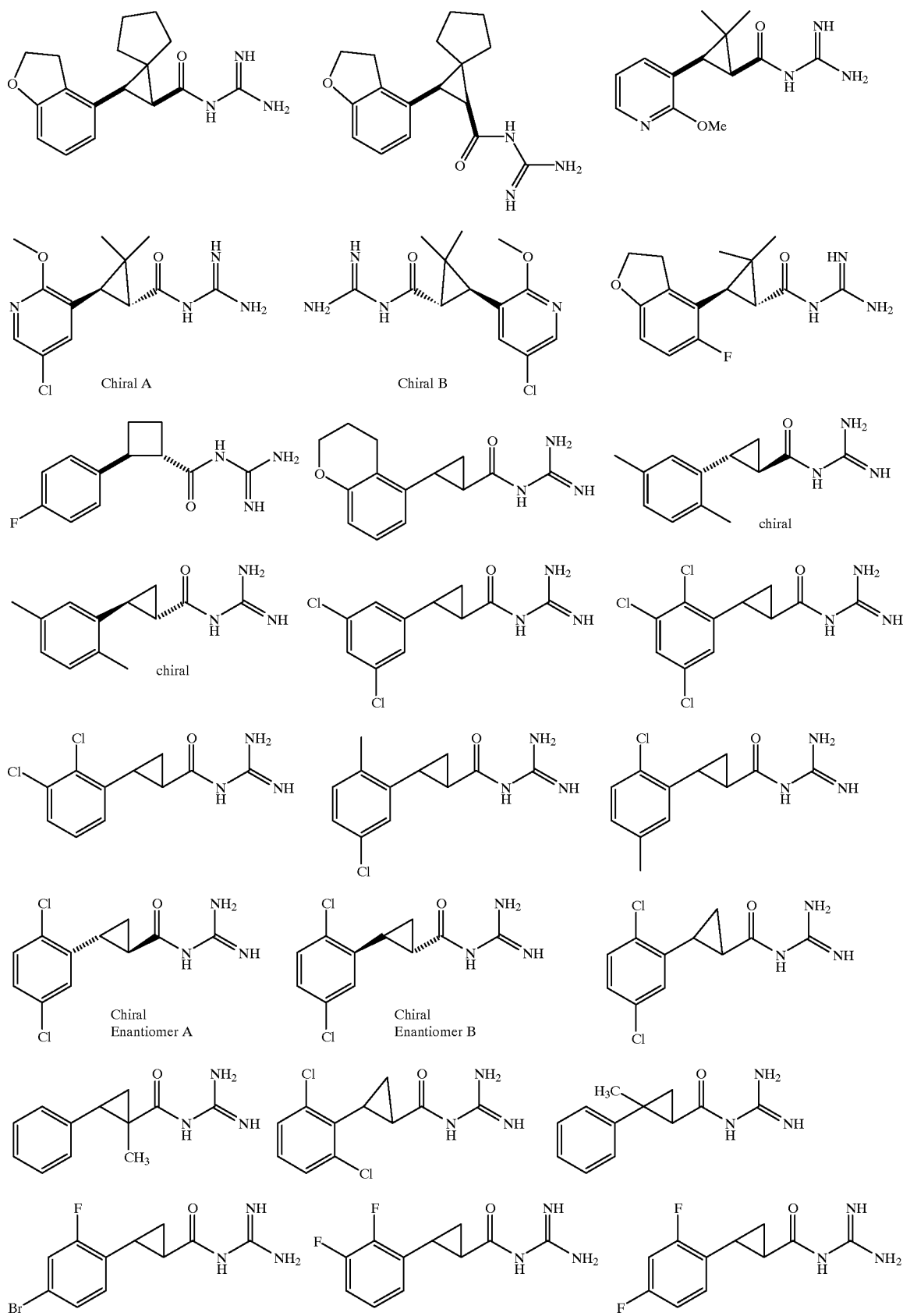

-continued
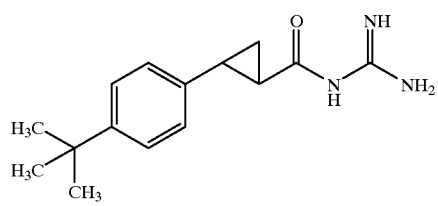
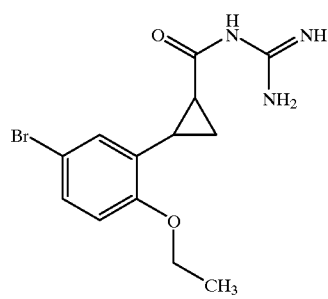
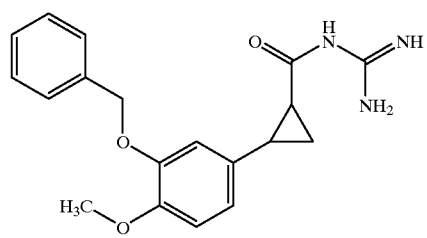
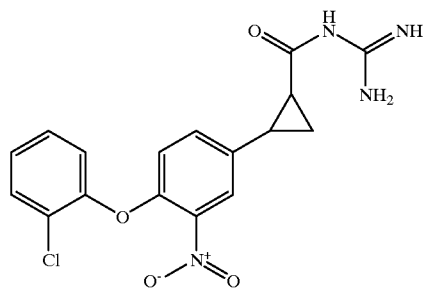
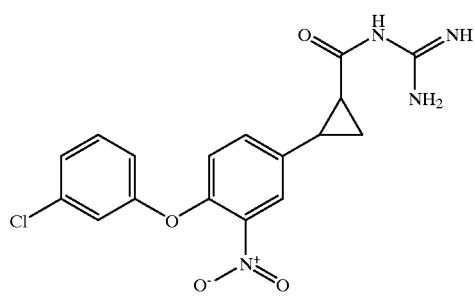
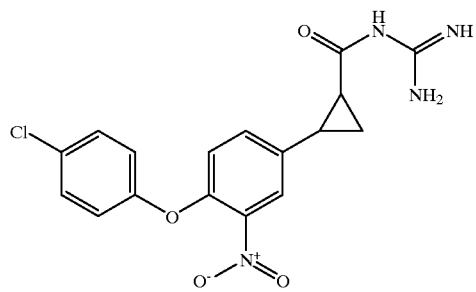
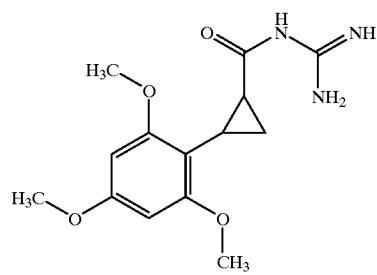
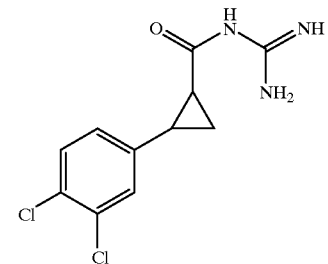
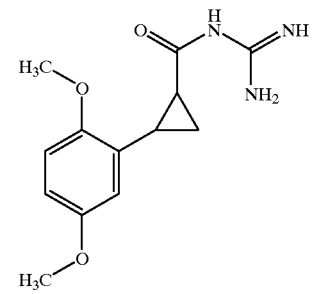
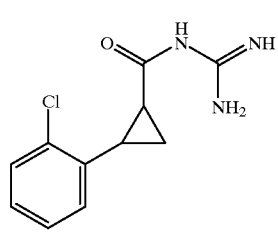
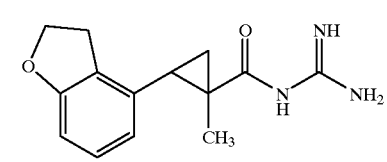
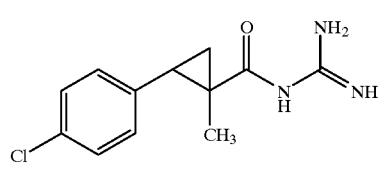
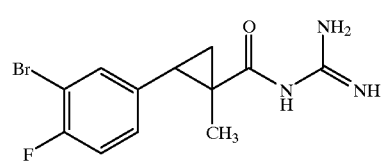
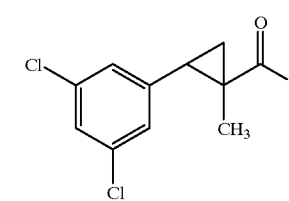
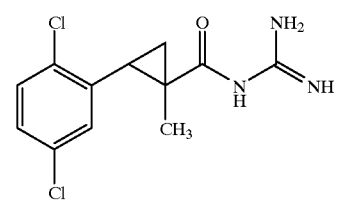

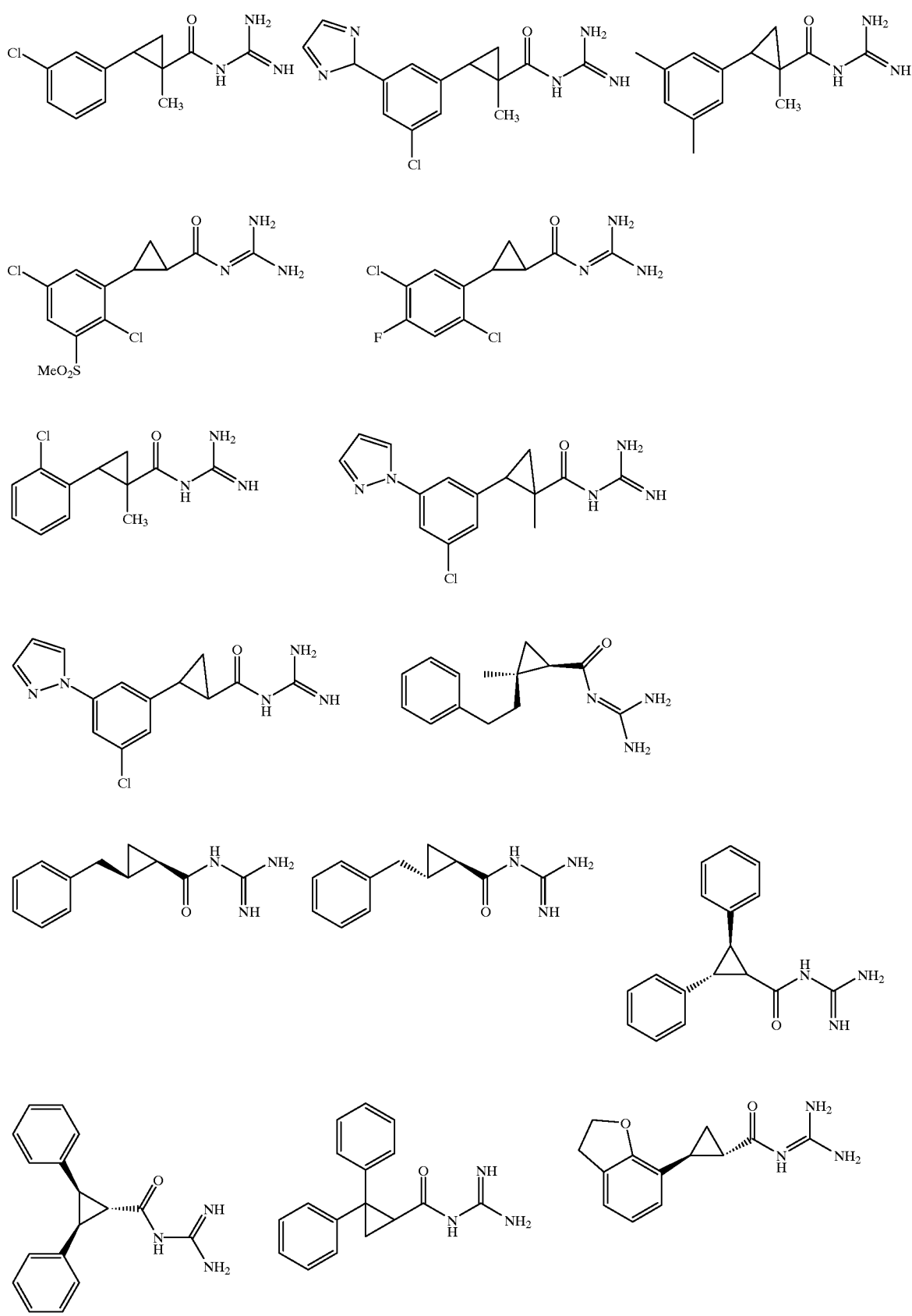

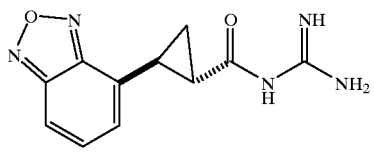 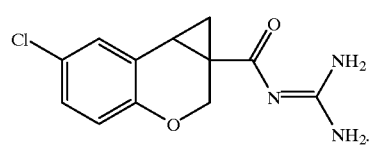

15. The compound as defined in claim 1 having the formula

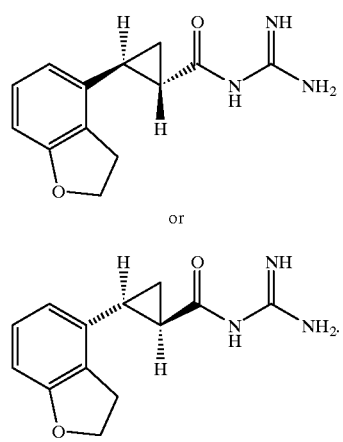

16. A pharmaceutical composition comprising a compound as defined in claim 1 and a pharmaceutically acceptable carrier therefor.

17. A method for preventing or treating a disorder caused by intracellular acidosis during myocardial ischemia, hypertension, angina pectoris, cardiac arrhythmia, reperfusion injury, myocardial necrosis, cardiac dysfunction, LDL-cholesterol, renal disease or heart failure, which comprises administering to a mammalian species in need of prevention or treatment a therapeutically effective amount of a compound as defined in claim 1.

18. A method for preventing or treating myocardial ischemia, which comprises administering to a mammalian species in need of prevention or treatment a therapeutically effective amount of a compound as defined in claim 1.

19. A method for preventing or treating an ischemic condition which comprises administering to a mammalian species in need of prevention or treatment a therapeutically effective amount of an antiischemic agent which is a compound as defined in claim 1.

20. A method of claim 19 wherein the ischemic condition is a peripheral vascular disorder.

21. A method for preventing or treating lower limb ischemia which comprises administering to a mammalian species in need of prevention or treatment a therapeutically effective amount of an antiischemic agent which is a compound as defined in claim 1.

22. The method as defined in claim 20 wherein the peripheral vascular disorder is Raynaud's disease.

23. The compound as defined in claim 1 having the structure

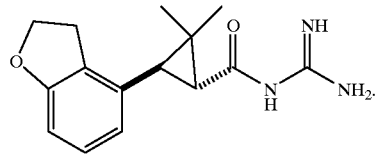

* * * * *